United States Patent [19]
Quan et al.

[11] Patent Number: 5,939,418
[45] Date of Patent: Aug. 17, 1999

[54] ISOXAZOLINE, ISOTHIAZOLINE AND PYRAZOLINE FACTOR XA INHIBITORS

[75] Inventors: Mimi Lifen Quan, Newark, Del.; John Wityak, West Grove; Robert Anthony Galemmo, Jr., Collegeville, both of Pa.; Petrus F. W. Stouten, Wilmington, Del.; James Russell Pruitt, Landenberg, Pa.; Donald J. P. Pinto, Newark, Del.

[73] Assignee: The DuPont Merck Pharmaceutical Company, Wilmington, Del.

[21] Appl. No.: 08/768,908

[22] Filed: Dec. 17, 1996

Related U.S. Application Data

[60] Provisional application No. 60/009,508, Dec. 21, 1995, and provisional application No. 60/030,666, Nov. 12, 1996.

[51] Int. Cl.$^6$ .................. A61K 31/505; A61K 31/42; C07D 413/06
[52] U.S. Cl. ............... 514/256; 514/275; 514/326; 514/340; 514/378; 514/380; 544/333; 546/209; 546/272.1; 548/240; 548/243; 548/244; 548/245
[58] Field of Search ................. 548/240, 243, 548/244, 245; 514/378, 380, 256, 275, 326, 340; 546/209, 272.1; 544/333

[56] References Cited

U.S. PATENT DOCUMENTS

| | | | |
|---|---|---|---|
| 4,454,211 | 6/1984 | Takasu et al. | 430/59 |
| 4,819,057 | 4/1989 | Naito et al. | 357/17 |
| 5,068,241 | 11/1991 | Fuchs et al. | 514/403 |
| 5,070,098 | 12/1991 | Fuchs et al. | 514/359 |
| 5,086,183 | 2/1992 | Fuchs et al. | 548/110 |
| 5,095,029 | 3/1992 | Kleefeld et al. | 514/403 |
| 5,162,542 | 11/1992 | Fuchs et al. | 548/364.4 |
| 5,247,094 | 9/1993 | Fuchs et al. | 548/268.4 |
| 5,380,868 | 1/1995 | Gallenkamp et al. | 548/365.4 |
| 5,525,622 | 6/1996 | Kanellakopulos et al. | 514/403 |

FOREIGN PATENT DOCUMENTS

| | | |
|---|---|---|
| 0053095 | 6/1982 | European Pat. Off. . |
| 0540051 | 5/1993 | European Pat. Off. . |
| 0679644 | 11/1995 | European Pat. Off. . |
| 923739 | 5/1992 | South Africa . |
| WO94/27972 | 12/1994 | WIPO . |
| WO95/14682 | 6/1995 | WIPO . |
| WO95/14683 | 6/1995 | WIPO . |

OTHER PUBLICATIONS

CA 122: 31516 Dihydropyrazole compounds useful as insecticides. Salmon, Sep. 28, 1994.

Tamaki, et al; Matlystatins, New Inhibitors of Type IV Collagenases from Actinomadura atramentaria; J. of Antibiotics; Dec. 1994; pp. 1472–1480 and 1481–1492.

Robeva, et al; Synthetic and endogenous inhibitors of snake venom metalloproteinases; Biomed. Biochim Acta.; Dec. 1991; pp. 769–773.

McCullagh et al; Carboxyalky peptide derivatives; Chemical Abstracts; Jun. 24, 1995; Abstract No. 221199.

Hauptmann, et al; Comparison of the Anticoagulant and Antithrombotic Effects of Synthetic Thrombin and Factor Xa Inhibitors; Throm. Haemostasis; 1990; 63(2); pp. 220–223.

Stuerzebecher et al; Synthetic Inhibitors of Serine Proteinases XXIII. Inhibition of Factor Xa by Diamidines; Throm. Research; 1980; 17; pp. 545–548.

Tidwell, et al; Strategies for Anticoagulation with Synthetic Protease Inhibitors. Xa Inhibitors versus Thrombin Inhibitors; Throm Research; 1980; 19; pp. 339–349.

Stuerzebecher et al; Synthetic Inhibitors of Serine Proteinases Inhibition of Factor Xa by Derivatives of Benzamidine; Throm Research; 1976; 9; pp. 637–646.

Nagahara, et al; Dibasic (Amidinoaryl) propanoic Acid Derivatives as Novel Blood Coagulation Factor Xa Inhibitors; J. Med. Chem.; 1997; 37; pp. 1200–1207.

Hauptmann et al; Anticoagulant potential of synthetic and recombinant inhibitors of factor Xa and thrombin in vitro; Blood Coagulation and Fibrinolysis; 1993; 4; pp. 577–582.

*Primary Examiner*—Joseph McKane
*Attorney, Agent, or Firm*—Don M. Kerr

[57] ABSTRACT

Isoxazolines, isothiazolines and pyrazolines which are inhibitors of Factor Xa, pharmaceutical compositions containing these compounds, and methods of using these compounds as anticoagulant agents for treatment and prevention of thromboembolic disorders. The compounds can be represented by the formula:

(I)

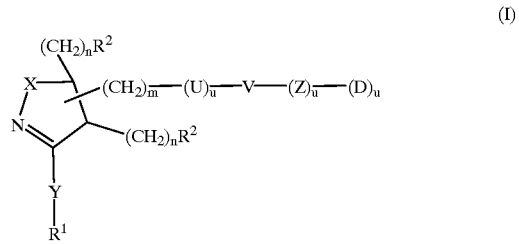

where X is O, S or $NR^{15}$.

12 Claims, No Drawings

ISOXAZOLINE, ISOTHIAZOLINE AND PYRAZOLINE FACTOR XA INHIBITORS

This application claims the benefit of U.S. Provisional Application No. 60/009,508, filed Dec. 21, 1995 and U.S. Provisional Application No. 60/030,666, filed Nov. 12, 1996.

FIELD OF THE INVENTION

This invention relates to isoxazolines, isothiazolines and pyrazolines which are inhibitors of Factor Xa, to pharmaceutical compositions containing these compounds, and to methods of using these compounds as anticoagulant agents for treatment and prevention of thromboembolic disorders.

BACKGROUND OF THE INVENTION

Stuerzebecher et al., *Thrombosis Research*, vol. 9, 637–646 (1976) describes comparative studies of a number of benzamidine derivatives as Factor Xa inhibitors. The most active inhibitors were 3-amidino-phenylaryl derivatives.

Tidwell et al., *Thrombosis Research*, vol. 19, 339–349 (1980) describes Factor Xa inhibitory activity of a series of heterocyclic aromatic mono- and di-amidines.

Stuerzebecher et al., *Thrombosis Research*, vol. 17, 545–548 (1980) describes Factor Xa inhibitory activity of a series of a,a'-bis-(4-amidinobenzyl) cycloalkanones, a,a'-bis-(4-aminobenzylidene)- and a,a'-bis-(3-aminobenzylidene) cycloalkanones with 5 to 8-membered rings, the corresponding non-cyclic derivatives, and derivatives containing only one amidino group.

Hauptmann et al., *Blood Coagulation and Fibrinolysis*, vol. 4, 577–582(1993) and Hauptmann et al., *Thromb. Haemostasis*, vol. 63(2), 220–223(1990) report testing of several synthetic compounds as Factor Xa inhibitors: Na-tosylglycyl-3-amidinophenylalanine methyl ester; 2,7-bis(4-amidinobenzylidene)-cycloheptanone-(1); Na-tosyl-4-amidinophenylalanine piperidide; Na-naphthyl-sulphonylglycyl-4-amidinophenylalanine piperidide; 4-methyl-1-N²-(methyl-1,2,3,4-tethydro-8-quinolinesulphonyl-L-arginyl-2-piperidine carbonic acid; and D-phenylalanyl-L-propyl-L-arginine chloromethyl ketone.

Nagahara et al., J. Med. Chem., vol. 37, 1200–1207(1994) describes several dibasic (amidinoaryl)propanoic acid derivatives as Factor Xa inhibitors.

Daiichi EPA 0 540 051 A1, published May 5, 1993, discloses aromatic amidine derivatives, including amidino naphthylenes, amidino-indoles, amidino-benzimidazoles, and amidino-benzothiophenes, which have Factor Xa inhibitory activity.

DuPont Merck WO 95/14683 and WO 95/14682, published Jun. 1, 1995, disclose isoxazoles and isoxaolines as antagonists of the platelet glycoprotein IIb/IIIa fibrinogen receptor. The isoxazoles and isoxaolines of WO 95/14683 are represented by the formula:

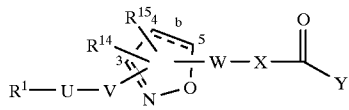

The isoxazolines of WO 95/14682 are represented by the formula:

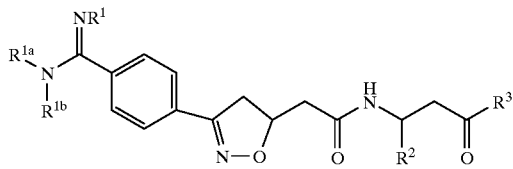

Copending, commonly assigned U.S. patent application Ser. No. 08/449597, filed May 24, 1995, discloses isoxazoline antagonists of the platelet glycoprotein IIb/IIIa fibrinogen receptor having the formula:

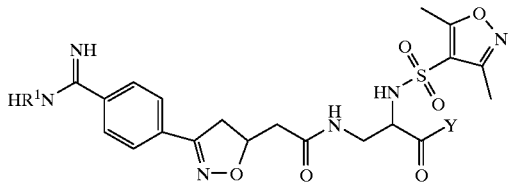

EP 53095 A and other references disclose various di-anilino-pyrazoline as components of photosensitive systems.

EP 438690 and other references disclose various 1-amido-pyrazolines as pesticides, e.g., insecticides, fungicides and acaricides.

To date there have been no isoxazoline, isothiazoline or pyrazoline derivatives described as Factor Xa inhibitors.

SUMMARY OF THE INVENTION

This invention provides novel compounds of Formula

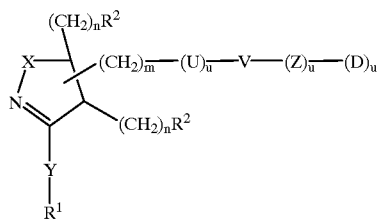

including pharmaceutically acceptable salts and prodrug forms thereof, and all stereoisomeric forms thereof and mixtures of such stereoisomeric forms, wherein:

U when present (i.e., when u=1) is selected from
—CO—NH—$(CH_2)_o$—
—CO—$(CH_2)_o$—
—$SO_2$—NH—$(CH_2)_o$—
—$SO_2$—$(CH_2)_o$—
—$NHSO_2$—$(CH_2)_o$—, provided m≠0
—NHCO—$(CH_2)_o$—, provided m≠0
—NH—$(CH_2)_o$—, provided m≠0
—O—$(CH_2)_o$—, provided m≠0
—S—$(CH_2)_o$—, provided m≠0
—CH=CH—$(CH_2)_o$—

X is O, S, $NR^{15}$

Y is selected from

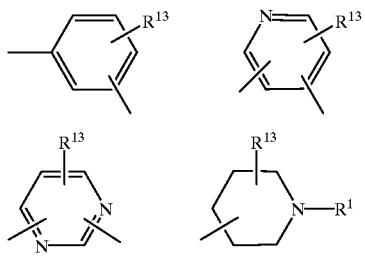

R¹ is selected from
(CH$_2$)$_p$NR$^5$R$^6$
C(NR$^{14}$)NR$^5$R$^6$
NHC(NR$^{14}$)NR$^5$R$^6$
NHC(NR$^{14}$)H
CONR$^5$R$^6$ R² is selected from
H
$C_1$–$C_6$ alkyl
$C_1$–$C_6$ alkoxy
CO$_2$R$^5$
CONHR$^5$
CONHCH$_2$CO$_2$R$^5$
CONH(CH$_2$)$_q$—R$^{10}$
R$^{10}$
CO—R$^5$
COCO$_2$R$^5$
COCONHR$^5$
SO$_n$R$^5$
SO$_2$NHR$^5$
NHR$^7$
CH=CHCO$_2$R$^5$
CH=CHCONHR$^5$
O—(CH$_2$)$_n$—R$^{10}$
SO$_n$—(CH$_2$)$_n$—R$^{10}$
NH—(CH$_2$)$_n$—R$^{10}$ U and R² taken together provide a spiro compound of formula IIa and IIb, or a compound of formula IIIa or IIIb:

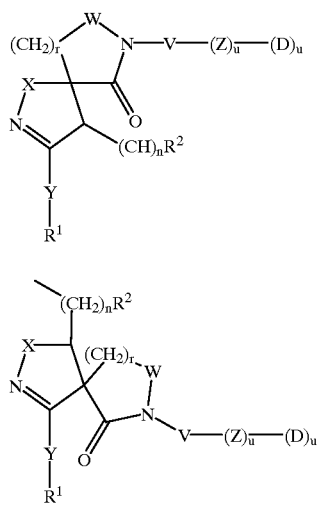

where W=CO, CH$_2$, CHOR$^5$ and r=1–3

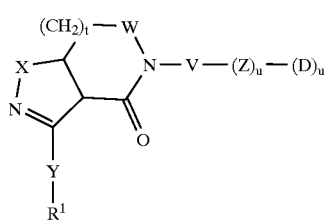

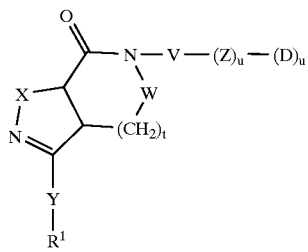

where W=CO, CH$_2$, CHOR$^5$ and t=0–2

R³ is selected from
(CH$_2$)$_s$NR$^5$R$^6$
C(NR$^{14}$)NR$^5$R$^6$
NHC(NR$^{14}$)NR$^5$R$^6$
NHC(NR$^{14}$)H
CONR$^5$R$^6$ V is selected from the following when Z and D are both absent:

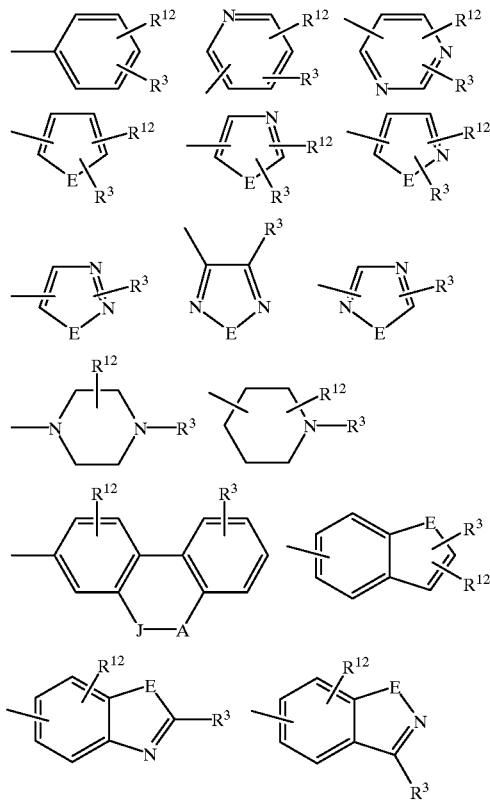

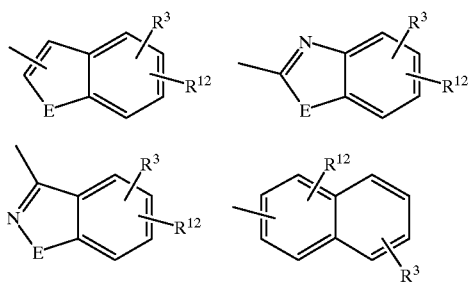
V is selected from the following when Z and/or D are present:
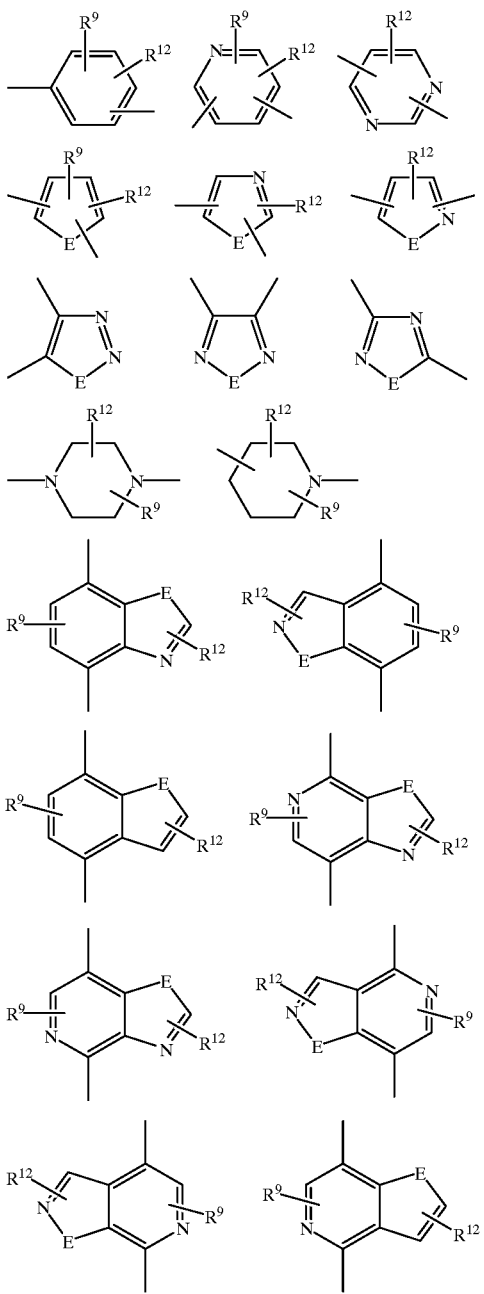
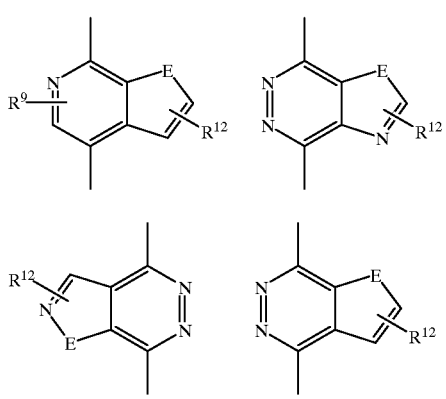
Z when present (i.e., when u=1) is selected from a single bond,
—CO—,
—(CH$_2$)$_t$—,
—SO$_n$—,
—SO$_2$NHR$^4$, provided D is absent
—NH—,
—NR$^7$—,
—O—
D when present (i.e., when u=1) is selected from
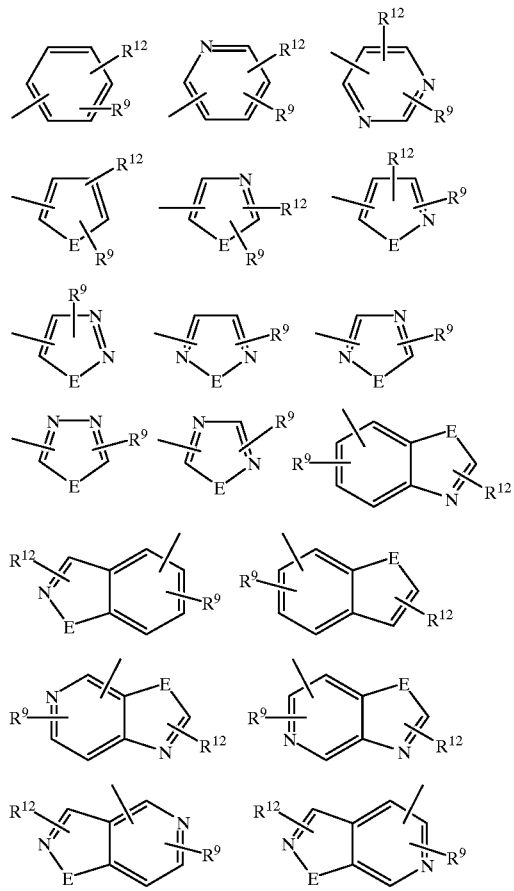

-continued

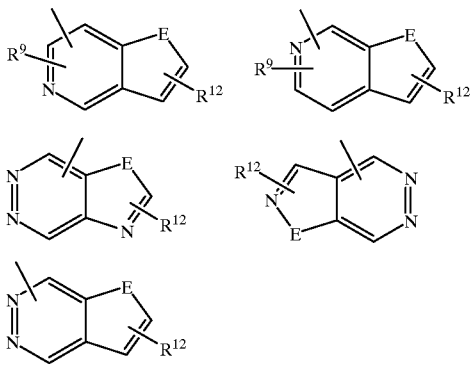

E is selected from N, NR$^5$, O, S;
J is selected from O, NR$^7$;
A is selected from CO, CH$_2$, SO, SO$_2$
R$^4$ is selected from
  H
  C$_1$–C$_6$ alkyl
  (CH$_2$)$_n$-phenyl
  (CH$_2$)$_n$-CONHR$^5$
  (CH$_2$)$_n$-CONHR$^5$CH$_2$CO$_2$R$^5$
R$^5$ and R$^6$ at each appearance are independently
  H
  C$_1$–C$_6$ alkyl
  (CH$_2$)$_n$-phenyl
R$^7$ is selected from
  H
  C$_1$–C$_6$ alkyl
  SO$_2$R$^5$
  COR$^5$
  (CH$_2$)$_r$—R$^{10}$
  (CH$_2$)$_n$-phenyl
R$^8$ is selected from
  H
  C$_1$–C$_6$ alkyl
  halogen
  NO$_2$
  CF$_3$
  OR$^5$
R$^9$ is selected from
  H
  C$_1$–C$_6$ alkyl
  halogen
  NO$_2$
  NHR$^7$
  SO$_2$NHR$^{11}$
  CF$_3$
  OR$^5$
  CO$_2$R$^5$
  CONR$^5$R$^7$
  CN
  (CH$_2$)$_p$NR$^5$R$^6$
  C(NR$^{14}$) NR$^5$R$^6$
  NHC(NR$^{14}$)NR$^5$R$^6$
  NHC(NR$^{14}$)H
  SO$_n$—R$^5$
  SO$_n$—CF$_3$
  imidazole, pyrazole, 1,2,3-triazole, 1,2,4-triazole and tetrazole, each optionally substituted with CF$_3$, halogen, NO$_2$, C$_1$–C$_5$ alkyl, or C$_1$–C$_5$ alkoxy;

R$^{10}$ is selected from

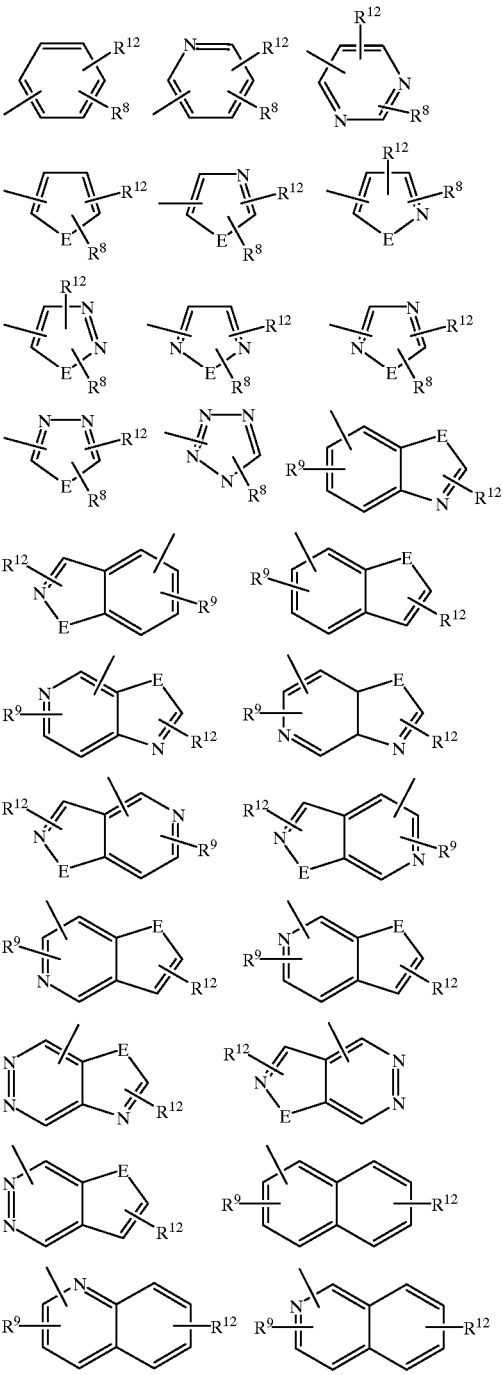

R$^{11}$ is selected from
  H
  C$_1$–C$_6$ alkyl
  (CH$_2$)$_n$-phenyl
  COR$^5$
  CO$_2$R$^5$
R$^{12}$ is selected from
  H
  C$_1$–C$_6$ alkyl
  C$_1$–C$_6$ alkoxy
  halogen
  NO$_2$ NHR$^7$
CN
CF$_3$
SONHR$^{11}$
R$^{13}$ is selected from
H
OH
C$_1$–C$_{10}$ alkyl
C$_1$–C$_{10}$ alkoxy
nitro
halo
CF$_3$
R$^{14}$ is selected from
H
OH
C$_1$–C$_{10}$ alkyl
C$_1$–C$_{10}$ alkoxy
CO$_2$—C$_1$–C$_{10}$ alkyl
CO—C$_1$–C$_{10}$ alkyl
CONH—C$_1$–C$_{10}$ alkyl
CONH—phenyl
CO$_2$(CH$_2$)$_n$-phenyl;
R$^{15}$ is selected from
H
C$_1$–C$_6$ alkyl,
C$_1$–C$_6$ alkoxy
CO$_2$R$^{14}$
CONHR$^{14}$
CONHCH$_2$CO$_2$R$^5$
CONH(CH$_2$)$_q$—R$^{10}$
(CH$_2$)$_n$R$^{10}$
CO—R$^5$
COCO$_2$R$^5$
COCONHR$^5$
SO$_2$NHR$^5$
at each appearance each of the following are independently:
m=0–2
n=0–4, except that in —SO$_n$—, n=0–2;
o=0–2
p=0–1
q=0–4
r=1–2
s=0–2
t=0–2
u=0–1,
provided that, when X is NR$^{15}$, Z and D are both absent,
Y is

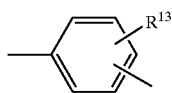

and V is

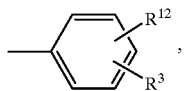, then at least one of R$^1$ and R$^3$ must be
C(NR$^{14}$)NR$^5$R$^6$
NHC(NR$^{14}$)NR$^5$R$^6$ or
NHC(NR$^{14}$)H.

As used in this specification and the claims:
the terms "alkyl" and "alkoxy" mean straight or branched chain alkyl and straight or branched chain alkoxy, each optionally substituted with 1 to 3 substituents independently selected from halo, C$_1$–C$_6$ straight or branched alkoxy, S(O)$_n$-alkyl where alkyl is C$_1$–C$_6$ straight or branched alkyl and n is 0–2, morpholino, C$_1$–C$_6$ alkylacyloxy, NR$^5$R$^7$ where R$^5$ and R$^7$ are as defined in claim 1, CN, NO$_2$, and CF$_3$;
the term "phenyl" means phenyl optionally substituted with 1 to 3 substituents independently selected from halo, C$_1$–C$_6$ straight or branched alkoxy, S(O)$_n$-alkyl where alkyl is C$_1$–C$_6$ straight or branched alkyl and n is 0–2, morpholino, C$_1$–C$_6$ alkylacyloxy, NR$^5$R$^7$ where R$^5$ and R$^7$ are as defined in claim 1, CN, NO$_2$, and CF$_3$;
the terms "halo" and "halogen" mean chloro, fluoro, bromo and iodo.

Many compounds of this invention have one or more asymmetric centers or planes. All chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by asymmetric synthesis, or synthesis from optically active starting materials. All chiral, (enantiomeric and diastereomeric) and racemic forms and all geometric isomeric forms of a structure are intended, unless the specific stereochemistry or isomer form is specifically indicated.

Preferred are those compounds of Formula I wherein, independently or concurrently:
U is present and is selected from
—CO—NH—(CH$_2$)$_o$—
—CO—(CH$_2$)$_o$—
—SO$_2$—NH—(CH$_2$)$_o$—
—SO$_2$—(CH$_2$)$_o$—
—NH—(CH$_2$)$_o$—
—O—(CH$_2$)$_o$—
X is O
Y is selected from

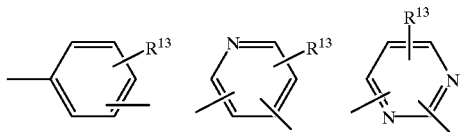

R$^1$ is selected from
C(NR$^{14}$)NR$^5$R$^6$
NHC(NR$^{14}$)NR$^5$R$^6$
R$^2$ is selected from
H
C$_1$–C$_6$ alkyl
C$_1$–C$_6$ alkoxy
CO$_2$R$^5$
CONHR$^5$
CONHCH$_2$CO$_2$R$^5$
CONH(CH$_2$)$_q$—R$^{10}$
R$^{10}$
CO—R$^5$
COCO$_2$R$^5$
COCONHR$^5$ SO$_n$R$^5$
SO$_2$NHR$^5$
NHR$^7$
CH=CHCO$_2$R$^5$
CH=CHCONHR$^5$
O—(CH)$_n$—R$^{10}$
SO$_n$—(CH)$_n$—R$^{10}$
NH—(CH)$_n$—R$^{10}$ V is selected from the following when Z and/or D are present:

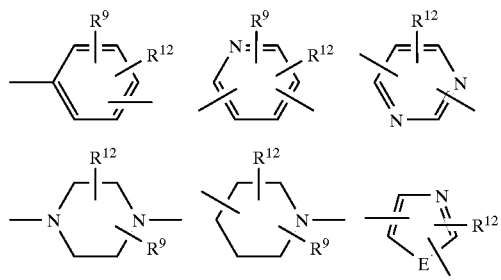

V is selected from the following when Z and D are both absent:

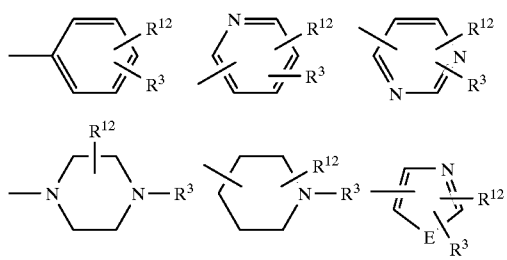

D when present (i.e., when u=1) is selected from

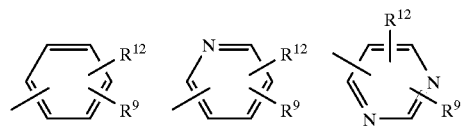

R$^{10}$ is selected from

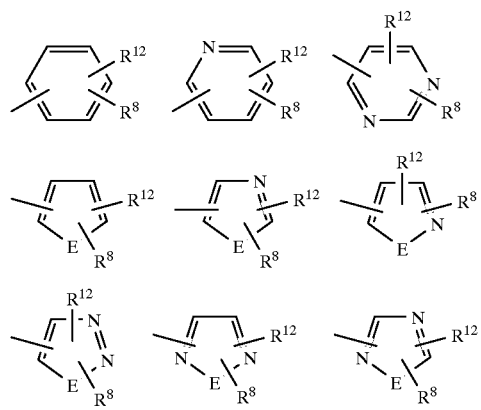

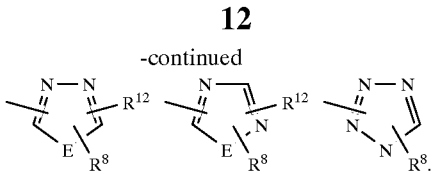

Of the preferred compounds, more preferred are those wherein, independently or concurrently:

U is —CO—NH—(CH$_2$)$_o$—

Y is selected from

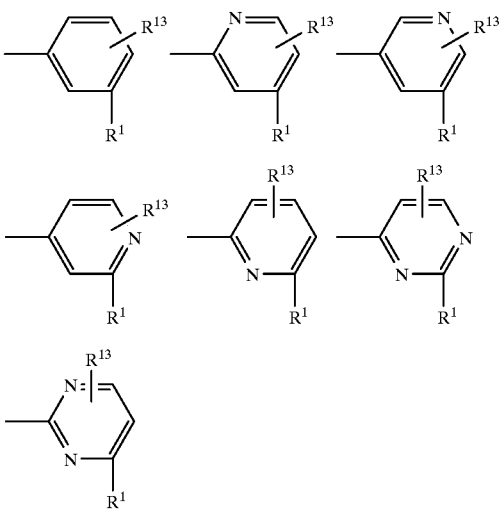

R$^1$ is C(NR$^{14}$)NR$^5$R$^6$

Z is absent or is present and is selected from
—O— and —NR$^7$—.

Of the more preferred compounds, especially preferred are those having the structures of V and VI:

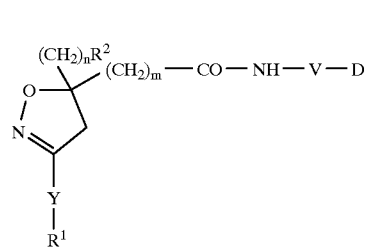
(V)

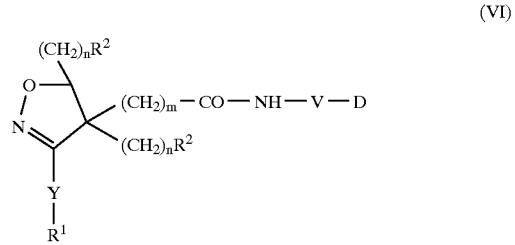
(VI)

wherein

R$^1$ is C(NR$^{14}$)NR$^5$R$^6$ and

D is selected from

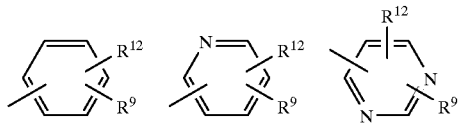

V is selected from the following:

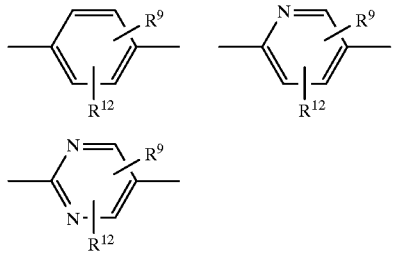

Specific preferred compounds of this invention include the following and pharmaceutically acceptable salt and prodrug forms thereof:

3-(3-Amidinophenyl)-5-[(2-naphthylsulfonyl)amino]methyl-isoxazoline 3-(3-amidinophenyl)-5-[[(2'-aminosulfonyl-[1,1']-biphenyl-4-yl)-methyl]aminocarbonyl]-5-(carbomethoxymethyl)isoxazoline 3-(3-amidinophenyl)-5-[[(2'-aminosulfonyl-[1,1']-biphenyl-4-yl)methyl]aminocarbonyl]-5-(aminocarbonylmethyl)isoxazoline 3-(3-amidinophenyl)-7-(2'-aminosulfonyl-[1,1']-biphenyl-4-yl)methyl[1-oxa-2,7-diazaspiro[4,4]non-2-ene-6,8-diones 3-amidinophenyl 3-(4-amidinophenyl)-5-[(aminocarbonyl)-isoxazolin-5-yl]acetamide 4-amidinophenyl 3-(3-amidinophenyl)-5-[(carbometoxy) isoxazolin-5-yl]acetamide 3-(3-amidinophenyl)-5-[(4-amidinophenyl)aminocarbonyl]isoxazoline 3-(3-amidinophenyl)-5-[(4-amidinophenyl)aminocarbonyl]-5-[(carbomethoxymethyl)aminocarbonylmethyl]isoxazoline 3-(3-amidinophenyl)-5-[(4-amidinophenyl)aminocarbonyl]-5-(carboxymethyl)isoxazoline 3-(4-amidinophenyl)-5-[(3-amidinophenyl)aminocarbonyl]-5-(carbomethoxymethyl)isoxazoline 3-(3-amidinophenyl)-5-[(4-amidinophenyl)methylaminocarbonyl]-5-(carbomethoxymethyl)isoxazoline 3-(3-amidinophenyl)-5-[(4-benzenesulfonylpiperidin-1-yl)carbonyl]-5-(carbomethoxymethyl)isoxazoline 3-(3-amidinophenyl)-5-[[(4-pyrimidin-5-yl)piperidin-1-yl]carbonyl]-5-(carbomethoxymethyl)isoxazoline 3-(3-amidinophenyl)-5-[(4-benzenesulfonylphenyl-1-yl)aminocarbonyl]-5-(carbomethoxymethyl)isoxazoline 3-(3-amidinophenyl)-5-[(4-amidinophenyl)aminocarbonyl]-5-(carbomethoxymethyl)isoxazoline 3-(3-amidinophenyl)-5-[([1,1']-biphenyl-4-yl)aminocarbonyl]-5-(carbomethoxymethyl)isoxazoline 3-(3-amidinophenyl)-5-[([1,1']-biphenyl-4-yl)aminocarbonyl]-5-(carboxymethyl)isoxazoline 3-(3-amidinophenyl)-5-[([1,1']-biphenyl-4-yl)aminocarbonyl]-5-(aminocarbonylmethyl)isoxazoline 3-(3-amidinophenyl)-5-[([1,1']-biphenyl-4-yl)aminocarbonyl]-5-(hydroxymethyl)isoxazoline 3-(3-amidinophenyl)-5-[(2'-aminosulfonyl-3'-n-propyl-[1,1']-biphenyl-4-yl)aminocarbonyl]-5-(carbomethoxymethyl)isoxazoline 3-(3-amidinophenyl)-5-[(2'-t-butylaminosulfonyl-[1,1']-biphenyl-4-yl)aminocarbonyl]-5-(carbomethoxymethyl)isoxazoline 3-(3-amidinophenyl)-5-[(2'-t-butylaminosulfonyl-[1,1']-biphenyl-4-yl)aminocarbonyl]-5-(aminocarbonylmethyl)isoxazoline 3-(3-amidinophenyl)-5-[(4'-amino-[1,1']-biphenyl-4-yl)aminocarbonyl]-5-(carbomethoxymethyl)isoxazoline 3-(3-amidinophenyl)-5-[(2'-trifluoromethyl-[1,1']-biphenyl-4-yl)aminocarbonyl]-5-(carbomethoxymethyl)isoxazoline 3-(3-amidinophenyl)-5-[(2'-aminosulfonyl-3-methyl-[1,1']-biphenyl-4-yl)aminocarbonyl)]-5-(carbomethoxyethyl)isoxazoline 3-(3-amidinophenyl)-5-[(2'-aminosulfonyl-3-methyl-[1,1']-biphenyl-4-yl)aminocarbonyl]-5-(carboxyethyl)isoxazoline 3-(3-amidinophenyl)-5-[(2'-aminosulfonyl-3-methyl-[1,1']-biphenyl-4-yl)aminocarbonyl]-5-(carbomethoxyethylene)isoxazoline 3-(3-amidinophenyl)-5-[[5-(2'-aminosulfonylphenyl-1-yl)pyrimidin-2-yl]aminocarbonyl]-5-(aminocarbonylmethyl)isoxazoline 3-(3-amidinophenyl)-5-[[5-(2'-aminosulfonylphenyl-1-yl)pyrimidin-2-yl]aminocarbonyl]-5-(hydroxyethyl)isoxazoline 3-(3-amidinophenyl)-5-[[5-(2'-aminosulfonylphenyl-1-yl)pyrimidin-2-yl]aminocarbonyl]-5-(methoxyethyl)isoxazoline 3-(3-amidinophenyl)-5-[[5-(2'-aminosulfonylphenyl-1-yl)pyrimidin-2-yl]aminocarbonyl]-5-(methyl)isoxazoline 3-(3-amidinophenyl)-5-[(2'-aminosulfonyl-[1,1']-biphenyl-4-yl)aminocarbonyl]-5-(carbomethoxymethyl)isoxazoline 3-(3-amidinophenyl)-5-[(2'-aminosulfonyl-[1,1']-biphenyl-4-yl)aminocarbonyl]-5-(carboxymethyl)isoxazoline 3-(3-amidinophenyl)-5-[(2'-aminosulfonyl-[1,1']-biphenyl-4-yl)aminocarbonyl]-5-(aminocarbonylmethyl)isoxazoline 3-(3-amidinophenyl)-5-[(2'-aminosulfonyl-[1,1']-biphenyl-4-yl)aminocarbonyl)-5-(hydroxyethyl)isoxazoline 3-(3-amidinophenyl)-5-[(2'-aminosulfonyl-[1,1']-biphenyl-4-yl)aminocarbonyl]-5-(carbomethoxymethylamninocarbonylmethyl)isoxazoline 3-(3-amidinophenyl)-5-[(2'-aminosulfonyl-[1,1']-biphenyl-4-yl)aminocarbonyl]-5-[(imidazole-4-yl)ethylaminocarbonylmethyl]isoxazoline 3-(3-amidinophenyl)-5-[(2'-aminosulfonyl-[1,1']-biphenyl-4-yl)aminocarbonyl]-5-(methoxyethyl)isoxazoline 3-(3-amidinophenyl)-5-[(2'-aminosulfonyl-[1,1']-biphenyl-4-yl)aminocarbonyl]-5-(methyl)isoxazoline 3-(3-amidinophenyl)-5-[(2'-aminosulfonyl-3-methyl-[1,1']-biphenyl-4-yl)aminocarbonyl]-5-(carbomethoxymethyl)isoxazoline 3-(3-amidinophenyl)-5-[(2'-aminosulfonyl-3-methyl-[1,1']-biphenyl-4-yl)aminocarbonyl]-5-(carboxymethyl)isoxazoline 3-(3-amidinophenyl)-5-[(2'-aminosulfonyl-3-methyl-[1,1']-biphenyl-4-yl)aminocarbonyl]-5-(aminocarbonylmethyl)isoxazoline 3-(3-amidinophenyl)-5-[(2'-aminosulfonyl-3-methyl[1,1']-biphenyl-4-yl)aminocarbonyl]-5-(carbomethoxymethylaminocarbonylmethyl)isoxazoline 3-(3-amidinophenyl)-5-[(2'-aminosulfonyl-3-methyl-[1,1']-biphenyl-4-yl)aminocarbonyl]-5-(hydroxyethyl)isoxazoline 3-(3-amidinophenyl)-5-[(2'-aminosulfonyl-3-methyl-[1,1']-biphenyl-4-yl)aminocarbonyl]-5-(methoxyethyl)isoxazoline 3-(3-amidinophenyl)-5-[(2'-aminosulfonyl-3-methyl-[1,1']-biphenyl-4-yl)aminocarbonyl]-5-(methyl)isoxazoline 3-(3-amidinophenyl)-5-[(2'-aminosulfonyl-3-fluoro-[1,1']-biphenyl-4-yl)aminocarbonyl]-5-(carbomethoxymethyl)isoxazoline 3-(3-amidinophenyl)-5-[(2'-aminosulfonyl-3-fluoro-[1,1']-biphenyl-4-yl)aminocarbonyl]-5-(carboxymethyl)isoxazoline 3-(3-amidinophenyl)-5-[(2'-aminosulfonyl-3-fluoro-[1,1']-biphenyl-4-yl)aminocarbonyl]-5-(aminocarbonylmethyl)isoxazoline 3-(3-amidinophenyl)-5-[(2'-aminosulfonyl-3-fluoro-[1,1']-biphenyl-4-yl)aminocarbonyl]-5-(hydroxyethyl)isoxazoline 3-(3-amidinophenyl)-5-[(2'-aminosulfonyl-3-fluoro-[1,1']-biphenyl-4-yl)aminocarbonyl]-5-(methoxyethyl)isoxazoline 3-(3-amidinophenyl)-5-[(2'-aminosulfonyl-3-fluoro-[1,1']-biphenyl-4-yl)aminocarbonyl]-5-(methyl)isoxazoline 3-(3-amidinophenyl)-5-[[2-(2'-aminosulfonylphenyl-1-yl)pyridin-5-yl]aminocarbonyl]-5-(carbomethoxymethyl)isoxazoline 3-(3-amidinophenyl)-5-[[2-(2'-aminosulfonylphenyl-1-yl)pyridin-5-yl]aminocarbonyl]-5-(carboxymethyl)isoxazoline 3-(3-amidinophenyl)-5-[[2-(2'-aminosulfonylphenyl-1-yl)pyridin-5-yl]aminocarbonyl]-5-(aminocarbonylmethyl)isoxazoline 3-(3-amidinophenyl)-5-[[2-(2'-aminosulfonylphenyl-1-yl)pyridin-5-yl]aminocarbonyl]-5-(hydroxyethyl)isoxazoline 3-(3-amidinophenyl)-5-[[2-(2'-aminosulfonylphenyl-1-yl)pyridin-5-yl]aminocarbonyl]-5-(methoxyethyl)isoxazoline 3-(3-amidinophenyl)-5-[[2-(2'-aminosulfonylphenyl-1-yl)pyridin-5-yl]aminocarbonyl]-5-(methyl)isoxazoline 3-(3-amidinophenyl)-5-[[5-(2'-aminosulfonylphenyl-1-yl)pyridin-2-yl]aminocarbonyl]-5-(carbomethoxymethyl)isoxazoline 3-(3-amidinophenyl)-5-[[5-(2'-aminosulfonylphenyl-1-yl)pyridin-2-yl]aminocarbonyl]-5-(carboxymethyl)isoxazoline 3-(3-amidinophenyl)-5-[[5-(2'-aminosulfonylphenyl-1-yl)pyridin-2-yl]aminocarbonyl]-5-(aminocarbonylmethyl)isoxazoline 3-(3-amidinophenyl)-5-[[5-(2'-aminosulfonylphenyl-1-yl)pyridin-2-yl]aminocarbonyl]-5-(hydroxyethyl)isoxazoline 3-(3-amidinophenyl)-5-[[5-(2'-aminosulfonylphenyl-1-yl)pyridin-2-yl]aminocarbonyl]-5-(methoxyethyl)isoxazoline 3-(3-amidinophenyl)-5-[[5-(2'-aminosulfonylphenyl-1-yl)pyridin-2-yl]aminocarbonyl]-5-(methyl)isoxazoline 3-(3-amidinophenyl)-5-[[5-(2'-aminosulfonylphenyl-1-yl)pyrimidin-2-yl]aminocarbonyl]-5-(carbomethoxymethyl)isoxazoline 3-(3-amidinophenyl)-5-[[5-(2'-aminosulfonylphenyl-1-yl)pyrimidin-2-yl]aminocarbonyl]-5-(carboxymethyl)isoxazoline 3-(3-amidinophenyl)-5-[5-(2'-aminosulfonylphenyl-1-yl)pyrimidin-2-yl]aminocarbonyl-5-carbomethoxymethyl-isoxazoline 3-(3-amidinophenyl)-5-[5-(2'-aminosulfonylphenyl-1-yl)pyridin-2-yl]aminocarbonyl-5-carbomethoxymethyl-isoxazoline 3-(3-amidinophenyl)-5-[2'-aminosulfonyl-[1,1']-biphenyl-4-yl]aminocarbonyl-5-(tetrazol-1-yl)methyl-isoxazoline 3-(3-amidinophenyl)-5-[5-(2'-aminosulfonylphenyl-1-yl)pyridin-2-yl]aminocarbonyl-5-(tetrazol-1-yl)methyl-isoxazoline 3-(3-amidinophenyl)-5-[5-(2'-aminosulfonylphenyl-1-yl)pyrimidin-2-yl]aminocarbonyl-5-(tetrazol-1-yl)methyl-isoxazoline 3-(3-amidinophenyl)-5-[2'-trifluoromethyl-[1,1']-biphenyl-4-yl]aminocarbonyl-5-(tetrazol-1-yl)methyl-isoxazoline 3-(3-amidinophenyl)-5-[5-(2'-trifluoromethylphenyl-1-yl)pyridin-2-yl]aminocarbonyl-5-(tetrazol-1-yl)methyl-isoxazoline 3-(3-amidinophenyl)-5-[5-(2'-trifluoromethylphenyl-1-yl)pyrimidin-2-yl]aminocarbonyl-5-(tetrazol-1-yl)methyl-isoxazoline 3-(3-amidinophenyl)-5-[5-(2'-trifluoromethylsulfonylphenyl-1-yl)pyridin-2-yl]aminocarbonyl-5-(tetrazol-1-yl)methyl-isoxazoline 3-(3-amidinophenyl)-5-[5-(2'-trifluoromethylsulfonylphenyl-1-yl)pyrimidin-2-yl]aminocarbonyl-5-(tetrazol-1-yl)methyl-isoxazoline 3-(3-amidinophenyl)-5-[2'-aminosulfonyl-3-flouro-[1,1']-biphenyl-4-yl]aminocarbonyl-5-(tetrazol-1-yl)methyl-isoxazoline 3-(3-amidinophenyl)-5-[2'-aminosulfonyl-3-chloro-[1,1']-biphenyl-4-yl]aminocarbonyl-5-(tetrazol-1-yl)methyl-isoxazoline 3-(3-amidinophenyl)-5-[2'-trifluoromethyl-3-flouro-[1,1']-biphenyl-4-yl]aminocarbonyl-5-(tetrazol-1-yl)methyl-isoxazoline 3-(3-amidinophenyl)-5-[2'-trifluoromethyl-3-chloro-[1,1']-biphenyl-4-yl]aminocarbonyl-5-(tetrazol-1-yl)methyl-isoxazoline 3-(3-amidinophenyl)-5-[5-(2'-aminosulfonylphenyl-1-yl)pyridin-2-yl]aminocarbonyl-5-methoxymethyl-isoxazoline 3-(3-amidinophenyl)-5-[2'-methylaminosulfonyl-[1,1']-biphenyl-4-yl]aminocarbonyl-5-(tetrazol-1-yl)methyl-isoxazoline 3-(3-amidinophenyl)-5-[5-(2'-methylaminosul-
fonylphenyl-1-yl)pyridin-2-yl]aminocarbonyl-5-
(tetrazol-1-yl)methyl-isoxazoline 3-(3-amidinophenyl)-5-[2'-methylsulfonyl-[1,1']-
biphenyl-4-yl]aminocarbonyl-5-(tetrazol-1-yl)methyl-
isoxazoline 3-(3-amidinophenyl)-5-[2'-methylsulfonyl-fluoro-[1,1']-
biphenyl-4-yl]aminocarbonyl-5-(tetrazol-1-yl)methyl-
isoxazoline 3-(3-amidinophenyl)-5-[2'-methylsulfonyl-chloro-[1,1']-
biphenyl-4-yl]aminocarbonyl-5-(tetrazol-1-yl)methyl-
isoxazoline 3-(3-amidinophenyl)-5-[2'-trifluoromethylsulfonyl-[1,1']-
biphenyl-4-yl]aminocarbonyl-5-(tetrazol-1-yl)methyl-
isoxazoline 3-(3-amidinophenyl)-5-[2'-aminosulfonyl-[1,1']-
biphenyl-4-yl]aminocarbonyl-5-(imidazol-1-yl)
methyl-isoxazoline 3-(3-amidinophenyl)-5-[2'-trifluoromethylsulfonyl-3-
fluoro-[1,1']-biphenyl-4-yl]aminocarbonyl-5-(tetrazol-
1-yl)methyl-isoxazoline 3-(3-amidinophenyl)-5-[2'-trifluoromethylsulfonyl-3-
chloro-[1,1']-biphenyl-4-yl]aminocarbonyl-5-(tetrazol-
1-yl)methyl-isoxazoline 3-(3-amidinophenyl)-5-[2'-aminosulfonyl-[1,1']-
biphenyl-4-yl]aminocarbonyl-5-(imidazol-1-yl)
methyl-isoxazoline 3-(3-amidinophenyl)-4-(2'-aminosulfonyl-[1,1']-
biphenyl-4-yl)aminocarbonyl-5-methoxymethyl-
isoxazoline 3-(3-amidinophenyl)-4-(2'-aminosulfonyl-[1,1']-
biphenyl-4-yl)aminocarbonyl-5-trifluoromethyl-
isoxazoline 3-(3-amidinophenyl)-5-(2'-aminosulfonyl-[1,1']-
biphenyl-4-yl)aminocarbonyl-4-methoxymethyl-
isoxazoline

DETAILED DESCRIPTION OF THE INVENTION

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

A convenient method for the synthesis of the isoxazoline compounds of this invention utilizes a dipolar cycloaddition of nitrile oxides with appropriate dipolarophiles to prepare the isoxazoline rings present in compounds of Formula I (for reviews of 1,3-dipolar cycloaddition chemistry, see 1,3-Dipolar Cycloaddition Chemistry (Padwa, ed.), Wiley, New York, 1984; Kanemasa and Tsuge, *Heterocycles* 1990, 30, 719). Scheme 1 shows a general synthesis of 3,5-substituted-isoxazolines. An appropriately substituted hydroxylamine is treated with NCS in DMF according to the method of Liu, et al. (*J. Org. Chem.* 1980, 45, 3916). The resulting hydrox-iminoyl chloride is then dehydrohalogenated in situ using TEA to give a nitrile oxide, which undergoes a 1,3-dipolar cycloaddition to a suitably substituted alkene to afford the isoxazoline. Alternatively, the oxime may be oxidatively chlorinated, dehydrochlorinated and the resulting nitrile oxide trapped by a suitable alkene under phase transfer conditions according to the method of Lee (*Synthesis* 1982, 508). The isoxazoline compounds of the general formula (I) wherein the 4 and 5 positions are substituted can be prepared following the 1,3-dipolar cycloaddition methodology using a suitable 1,2-disubstituted olefin as a dipolarophile. A mixture of regioisomers is formed and the regioisomers can be separated by column chromatography. An example is shown in Scheme 2. Optically active isoxazolines can be obtained by chiral HPLC separation of the two enantiomers, or enzymatic resolution on the regioisomeric esters. It can also be obtained by the use of an appropriate chiral auxilliary on the dipolarophile as described by Olsson (*J. Org. Chem.* 53, 2468, 1988). The synthetic methods described above may also be used for the synthesis of compounds of this invention where Y is pyridyl or pyrimidyl derivatives in formula (I).

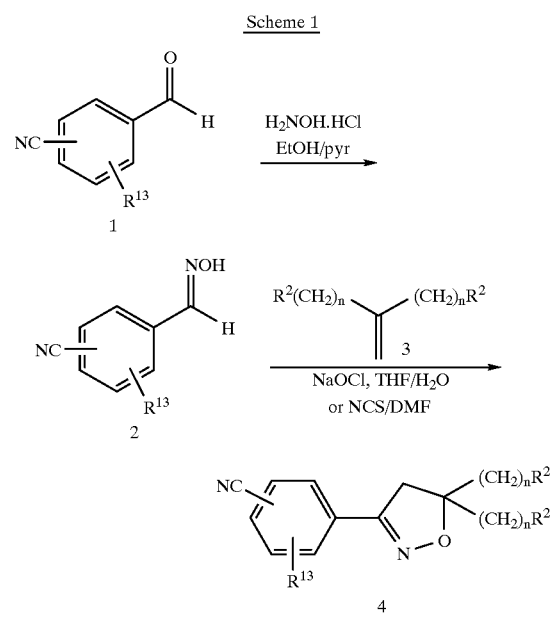

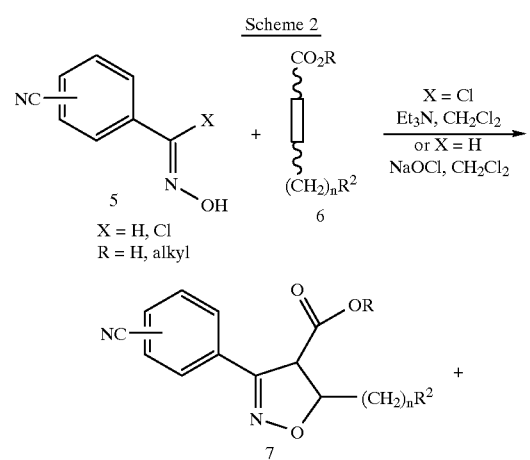

-continued

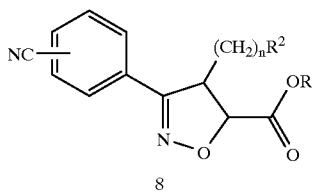

Many isoxazoline compounds of this invention can use commercially available substituted alkenes as starting materials. Compounds with $R^2$ is acid or amide can be prepared and hetreoaromatics with allyl of vinyl bromide. The C-linked aromatic and hetreoaromatic compounds can be synthesized using Zinc and Copper organometallics shown by Knochel (*Tet. Lett.* 31, 4413–4416, 1990), or using palladium-catalyzed coupling of an a-stannyl acrylate to aryl iodides or triflates by Levin (*Tet. Lett.* 34, 6211–6214, 1993). These reactions are exemplified in Scheme 4. The N-linked heteroaromatic compounds can be prepared by alkylation of the hetroaromatics with allyl bromides. An example is shown in Scheme 5. Compounds with $R^2$ is $COCO_2R$ or COCONHR can be prepared by the method discribed by Iwanowicz (*Bioorg. & Med. Chem. Lett.*, 2, 1607–1612, 1992).

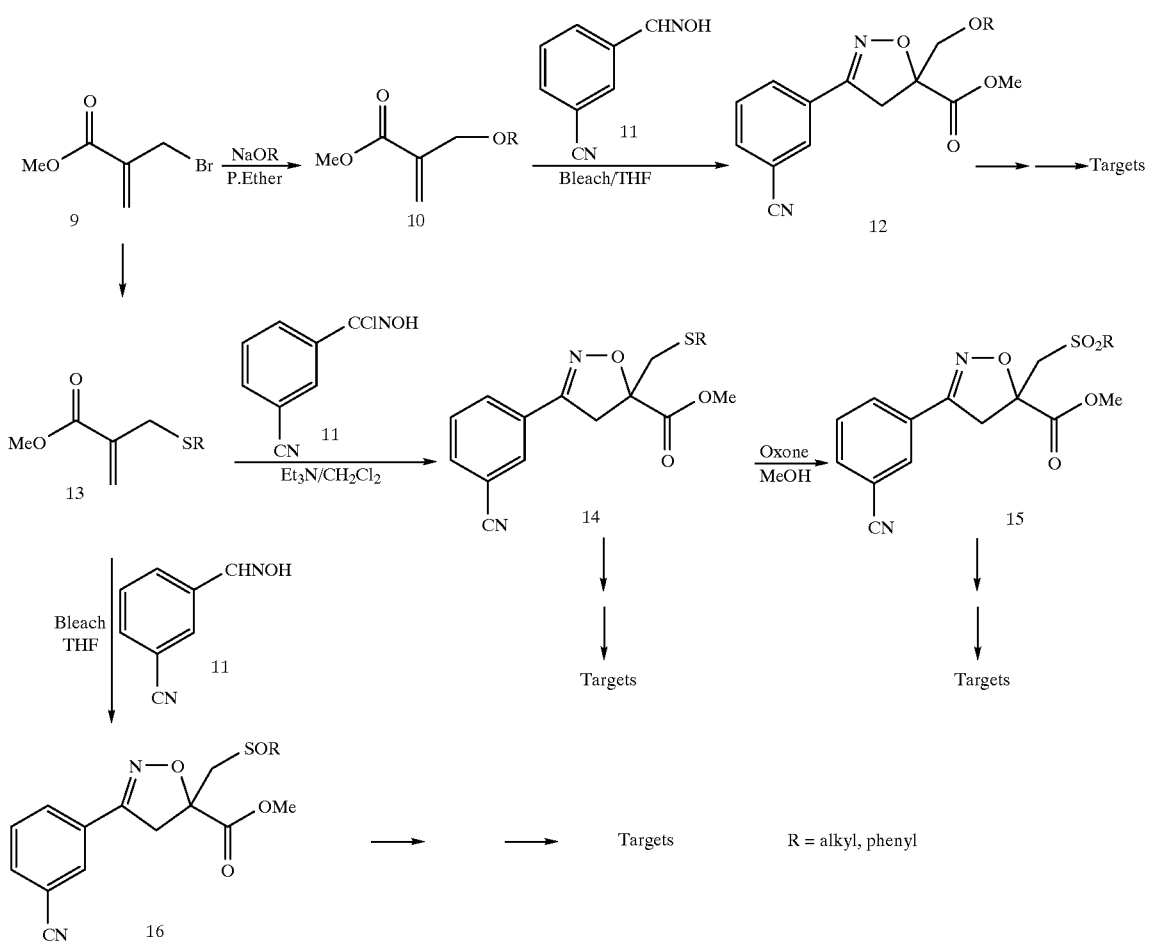

from the commercially available alkene-esters or alkene acids. The transformations of the functional groups can be done either at the alkene stage or after the isoxazoline ring is formed. Compounds with $R^2$ is $O(CH_2)_nR$, $NH(CH_2)_nR$, $S(CH_2)_nR$, where R is $R^5$ or $R^{10}$, can be prepared from substituted allyl bromide. An example is shown in Scheme 3. The sulfoxides and sulfones can be prepared from oxidation of the thio-compounds (Scheme 3). Compounds wh $R^2$ is aromatics and heteroaromatics ($R^{10}$) can be prepared from the reaction of the bromide or iodide of the aromatics

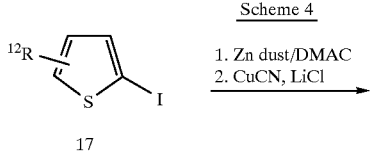

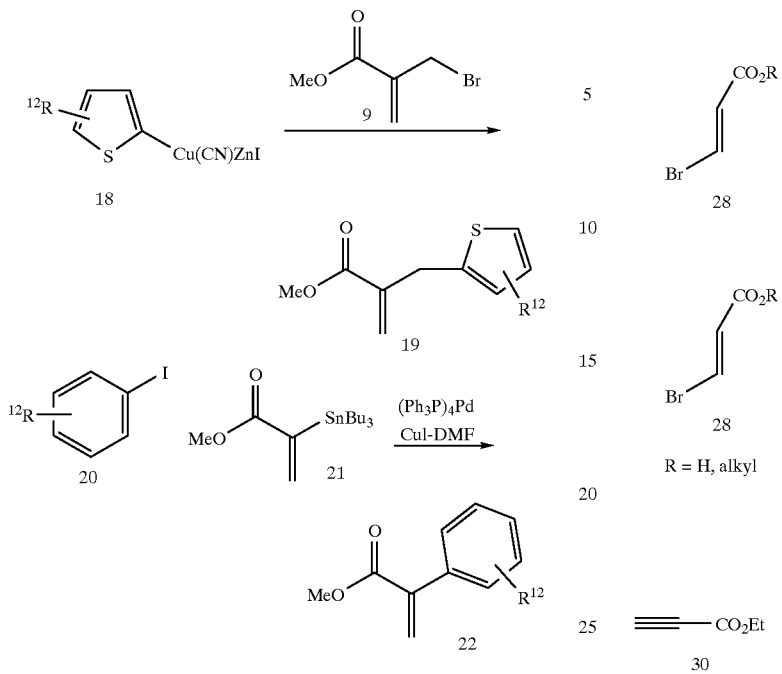

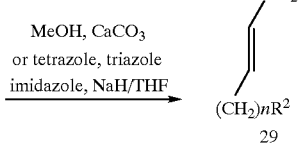

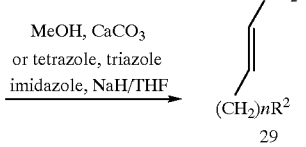

R = H, alkyl

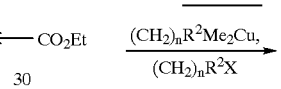

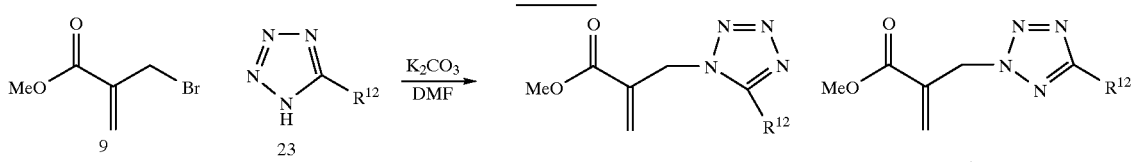

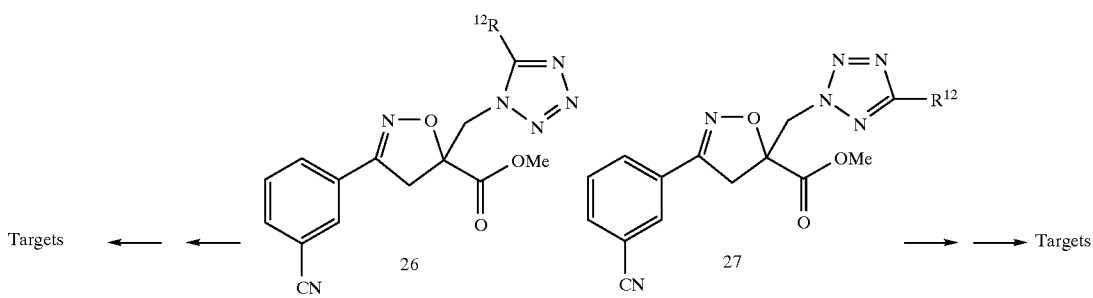

Appropriately substituted crotonate ester can be used as starting material for 4,5-disubstituted isoxazolines. The crotonate esters can be obtained from commertial sources or can be obtained from ethyl-4-bromocrotonate by nucleophilic displacement reactions shown in Scheme 6. Trisubstituted olefins as diplolarophiles can be obtained from ethylpropiolate by the cuprate chemistry (Scheme 7) according to the method described by Deslongchamps (*Synlett*, 660, 1994).

-continued

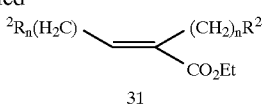

The isothiazoline compounds of this invention of formula (I) can be prepared by cycloaddition reaction of nitrile sulfides with olefins (Howe, *J. Org. Chem.*, 43, 3742, 1978) as shown in Scheme 8. The nitrile sulfide is generated by thermolysis of 5-substituted 1,3,4-oxthiazol-2-one.

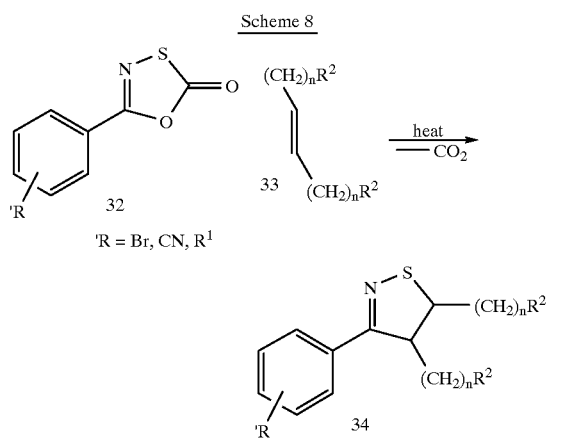

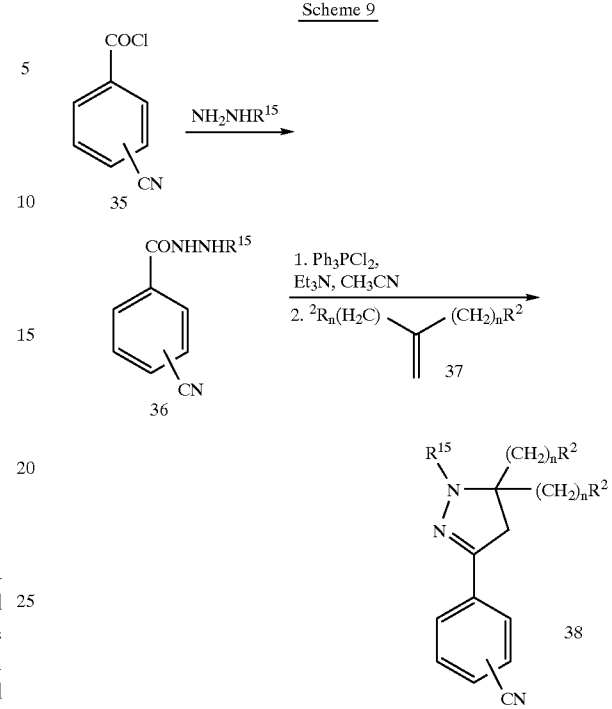

The pyrazoline compounds of this invention of formula (I) cab be prepared by the method described by Wahoff and Zahran (*Synthesis*, 876–879, 1987). An example of the synthesis is shown in Scheme 9. The hydrozine is coupled with the acyl chloride. The N-acylated hydrozine is reacted with dichlorotriphenylphosphorane and triethylamine. The nitrilimine generated in situ undergoes a 1,3-dipolar cycloaddition reaction with a suitable alkene to give the pyrazoline. The pyrazolines may also be prepared from isoxazolines as shown in Scheme 10. The isoxazoline was reacted with molybdenum hexacarbonyl in the conditions described by Baraldi (*Synthesis*, 276, 1987) provides the b-hydroxyketone. Dehydration of the b-hydroxyketone with p-toluenesulfonic acid yields the a,b-unsaturated ketone, which was then treated with hydrazine to afford the desired pyrazoline.

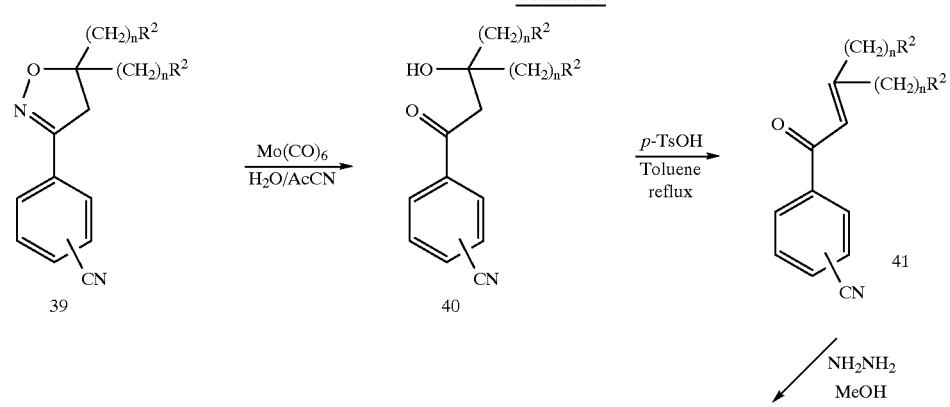

-continued

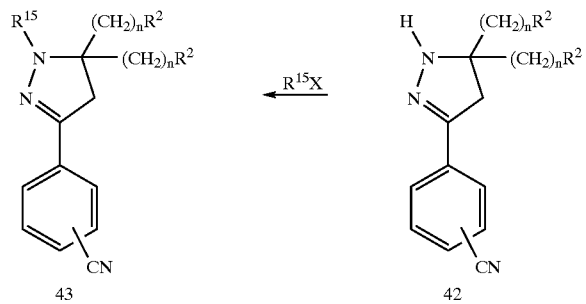

43 ← R¹⁵X — 42

Compounds of this invention where U in formula (I) is CONH may be prepared using substituted acrylates, vinyl acetate, or crotonate as starting materials. The core ring structures can be synthesized as described above and the easter group is then coupled with an appropiate amine using standard conditions for the formation of amide bonds. The nitrile is then converted to the amidine via the imidate or thioimidate under standard conditions. Some of the compounds are prepared following the procedures described in copending commonly-assigned U.S. patent application U.S. Ser. No. 08/337920. An example of these compounds is shown in Scheme 11. The 3-substituted-isoxazoline-5-ylcarboxylic acids or 3-substituted-isoxazoline-5-ylacetic acids can be converted to the corresponding amidines first, followed by protection as the Boc-derivatives or CBZ-derivatives. They were then coupled with appropiate amines as exemplified in Scheme 12. Compounds of this invention where $R^1$ is NHCH($NR^5$) in formula (I) may be prepared from amine derivatives by reaction of the amine with ethyl formimidate and N,N-dimethylpyridine in refluxing ethanol. Compounds of this invention where $R^1$ is NHC($NR^5$)$NR^5R^6$ in formula (I) may be prepared from amine derivatives by reaction of the amine with either formamidine sulfonic acid and N,N-dimethylpyridine in refluxing ethanol (Kim, et al. *Tet. Lett.* 29, 3183, 1988), or Bocprotected pyrazole carboxamidine in DMF (Bernatowicz et al. *Tet. Lett.* 34, 3389, 1993).

Scheme 11

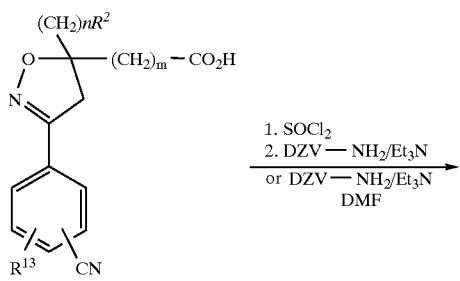

44

1. SOCl₂
2. DZV—NH₂/Et₃N
or DZV—NH₂/Et₃N
DMF

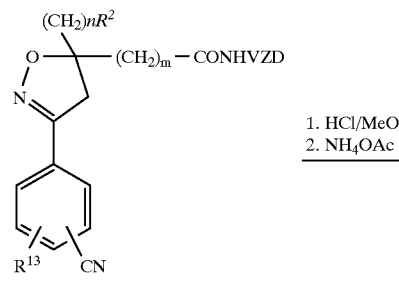

45

1. HCl/MeOH
2. NH₄OAc

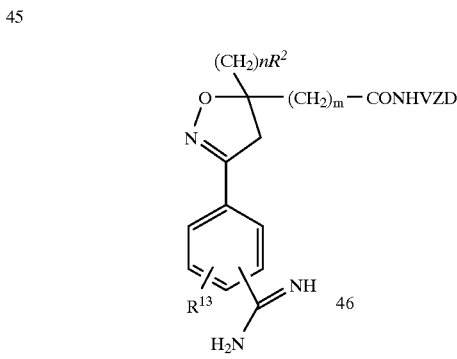

46

Scheme 12

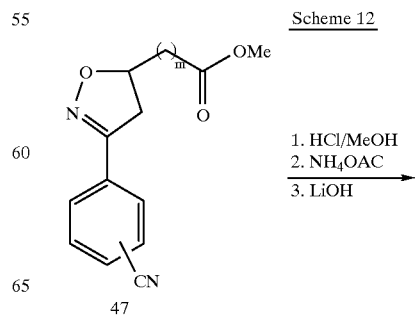

47

1. HCl/MeOH
2. NH₄OAC
3. LiOH

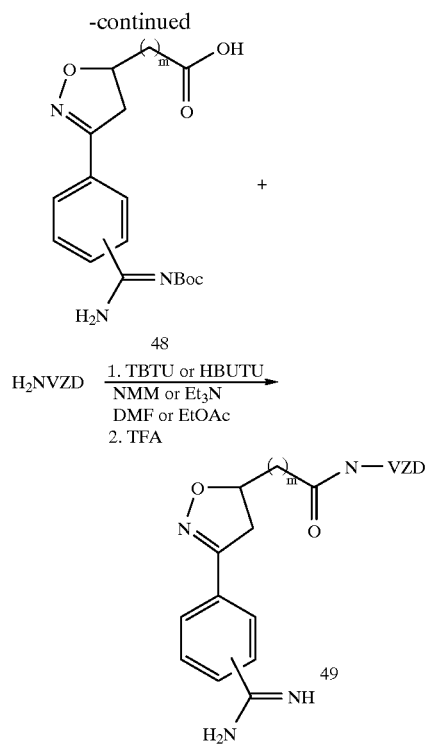

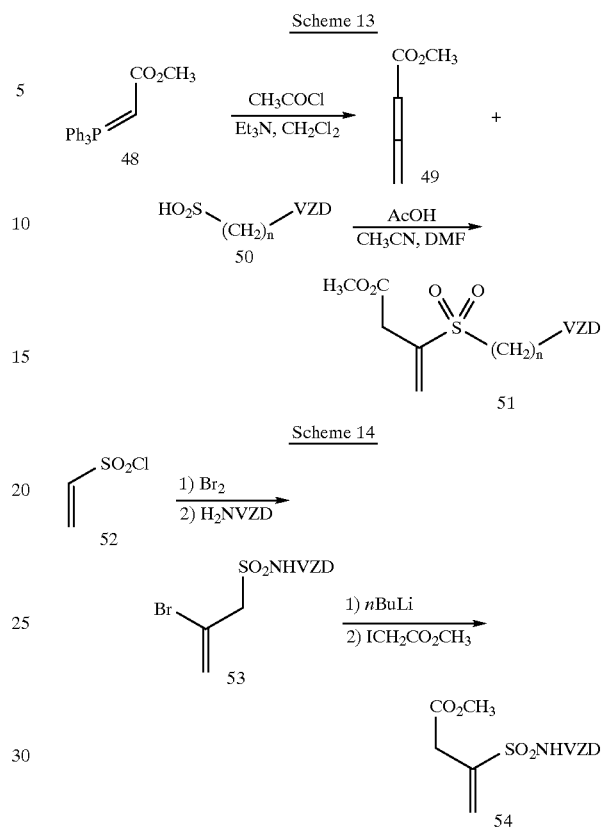

The sulfone derivatives where U is —$SO_2$—$(CH_2)_o$— are prepared as exemplified by the reactions in Scheme 13. Methyl (triphenylphosphoranylidene)-acetate is reacted with acetyl chloride to give the desired allene. A sulfinic acid, prepared by hydrogen peroxide oxidation of the corresponding thiol, is added into the allene to give the desired alkene (Padwa, *J. Org. Chem*, 54, 4232, 1989). This alkene can be used in the previously described cycloaddition reactions. The sulfonamide derviatives where U is —$SO_2$—NH— are prepared as exemplified by the reactions in Scheme 14. Vinyl sulfonyl chloride is brominated, then reacted with an amine (Barnett, *Tet. Lett.*, 651, 1968). Halogen-metal exchange and alkylation with iodoacetate gives the desired substituted vinyl sulfonamide (Stetan, *Chem, Ber.*, 122, 169, 1889) which can be used in the previously described cycloaddition reactions.

Isoxazoline compounds of the general formula I wherein U is thio, sulfonyl, or sulfonamide can also be prepared by the method outlined in scheme 15. The isoxazoline thioxanthate can be converted to the sulfonylchloride by treatement with chlorine in glacial acetic acid. The sulfonylchloride is then coupled with an appropriate amine to provide the desired sulfonamide. Alternatively the thioxanthate can be hydrolysed with sodium hydroxide in ethanol to the thiol followed by traping of the intermediate thiol with an appropriate benzylbromide to afford the thioalkylphenylanalog. Oxidation of the thio-compound with MCPBA or oxone affords the sulfoxide and or sulfone.

Scheme 15

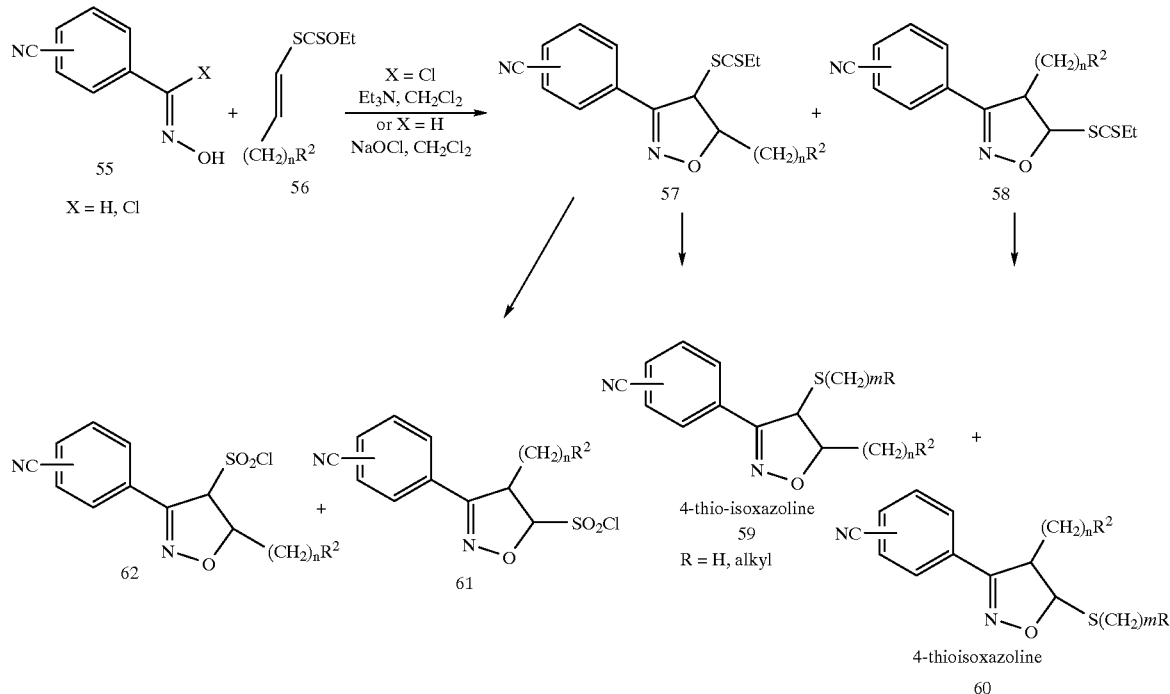

Compounds of this invention where U is alkene, ether, —NHSO$_2$—, ans —NHCO— can be prepared from the same intermediate as shown in Scheme 16. The 5-hydroxymethylisoxazoline is formed by the 1,3-dipolar cycloaddition described above The alcohol can be oxidized to the corresponding aldehyde aand the converted to the alkene-linked compound by Wittig reaction. The alkene-linked compounds can then be reduced to the corresponding alkyl-linked compounds. The alkyl-linked compounds can also be prepared using Zinc and Copper organometallics shown by Knochel (*Tet. Lett.* 31, 4413–4416, 1990, see Scheme 4), The 5-hydroxymethyl group can be converted to the azide, and then reduced to the corresponding amine. This amine intermediate is the converted to compounds with —NHSO$_2$—, and —NHCO— using suitable sulfonyl or acyl chloride. The 5-hydroxymethylisoxazoline can be converted to the ether-linked compound by Mitsunobo reaction. The ether and amine linked compounds can also be prepared by displacement of the allyl bromide shown in Scheme 17.

Scheme 16

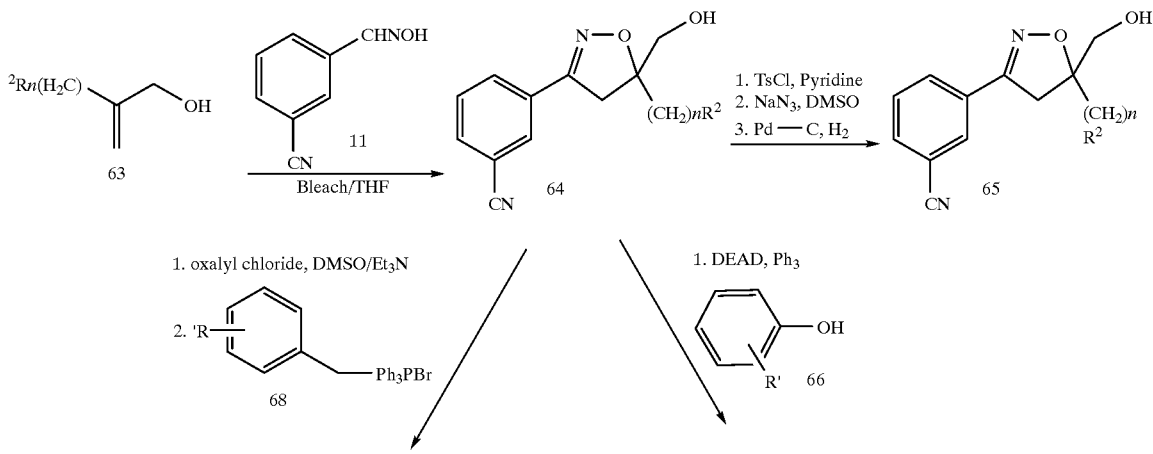

31

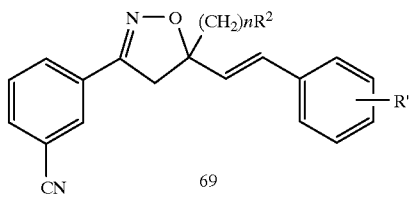
69

32

-continued

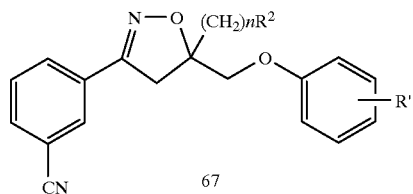
67

R' = Br, ZD

Scheme 17

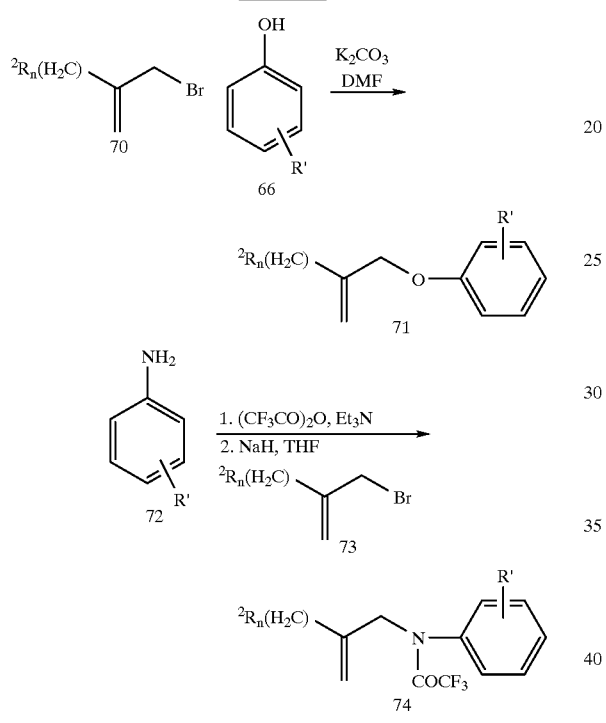

R' = Br, DZ

Scheme 18

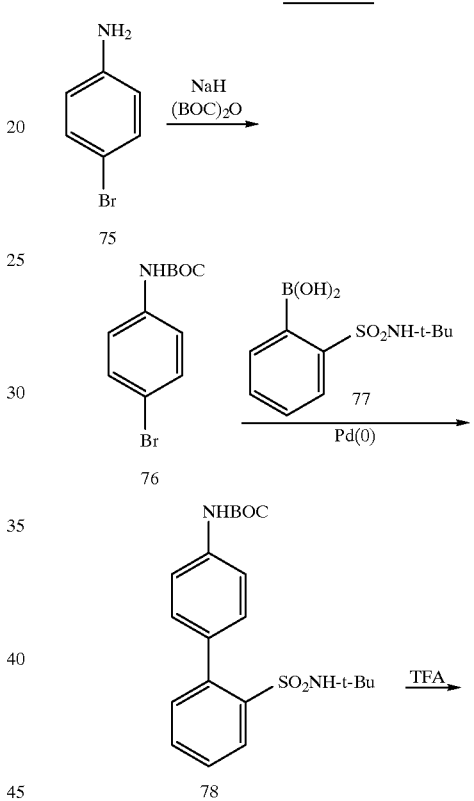

Compounds of this invention where U is —CO— can be prepared by palladium-catalyzed coupling reactions of organozinc reagents with acid chlorides (Jackson, Synlett, 819–820, 1995 and Sato, Chem. Lett., 1135, 1981) or by organimetallics of Zinc and Copper described by Knochel (J. Org. Chem. 53, 5791–5793, 1988).

Compounds of this invention where Z is absent may be prepared as shown by an example in Scheme 18. 4-Bromoaniline is protected as Boc-derivative and the coupled to 2-(t-butylamino)sulfonylphenylboronic acid under Suzuki conditions. 2-(t-Butylamino) sulfonylphenylboronic acid is prepared by the method described by Rivero (Bioorg. Med. Chem. Lett., 189, 1994). Deprotection with TFA provides the aminobiphenyl compound. The aminobiphenyl is the coupled to the core ring structures first as described above. The Bromoaniline can be linked to the core ring structures first as described above, and then undergoes Suzuki reaction to give the desired product.

Compounds of this invention where —Z— is —SO$_2$— are exemplified by the peperidine derivative shown in Scheme 19. Compounds of this invention where —Z— is —NH—, —O—, and —S— can be prepared by the methods described in Scheme 20.

Scheme 19

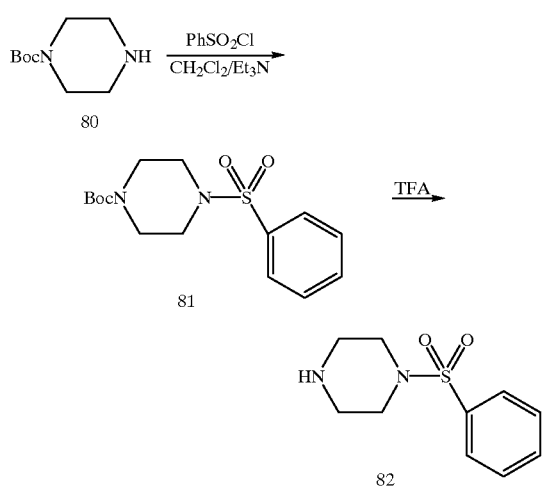

Scheme 20

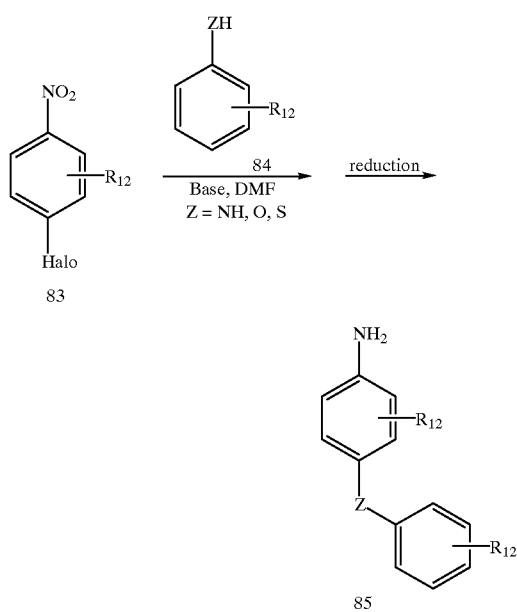

Some of the compounds of this invention may also be prepared as shown in Scheme 21. Itaconic anhydride reacts with appropiate amine to give 3-carboxy-3-butenamide. The benzaldehyde oxime is oxidatively chlorinated and dehydrochlorinated. The resulting nitrile oxide then reacted with 3-carboxy-3-butenamide to yield the 3,5,5-trisubstituted isoxazoline which was then converted to the final benzamidine as described above.

Scheme 21

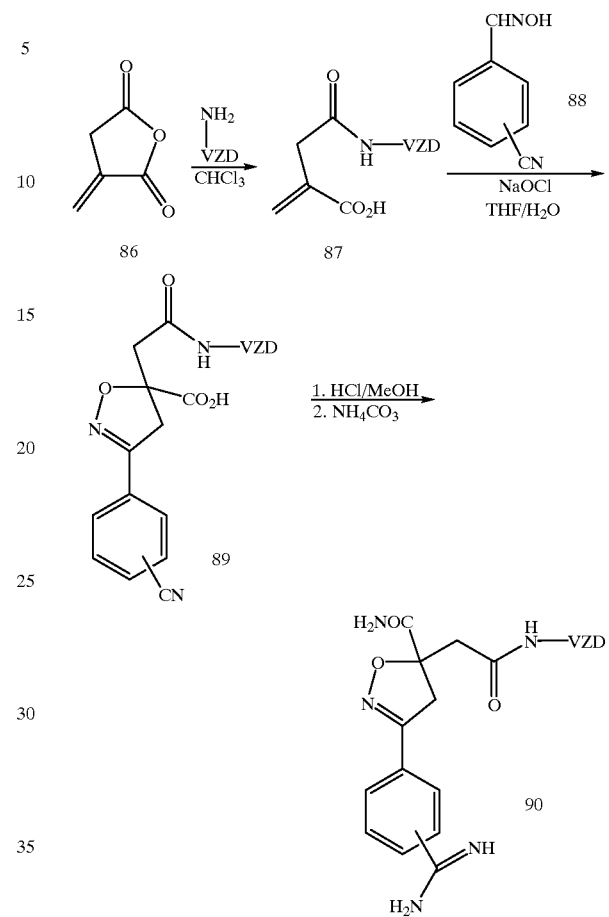

Compounds of this invention where Y is a piperidine derivative in formula (I) may be prepared from piperidine alcohols which are commercially available or prepared by coupling 4-brompyridine and appropiate length acetylenic alcohol followed by reduction. The piperidine alcohol is oxidized to the corresponding aldehyde under standard conditions. The aldehyde is converted to the isoxazoline by the same methods described above. An example of such a convertion is shown in Scheme 22 where n=0–3.

Scheme 22

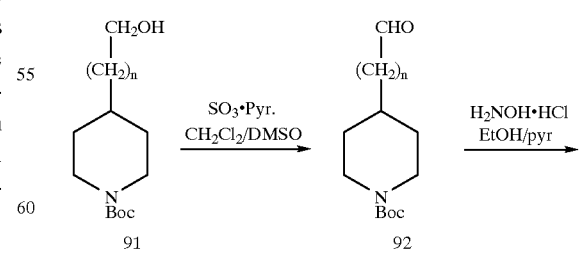

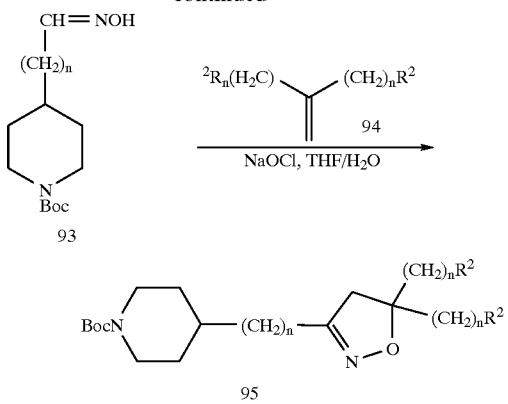

Swern oxidation conditions to generate the corresponding aldehyde, which can cyclized to give the spiro-compound.

Scheme 23

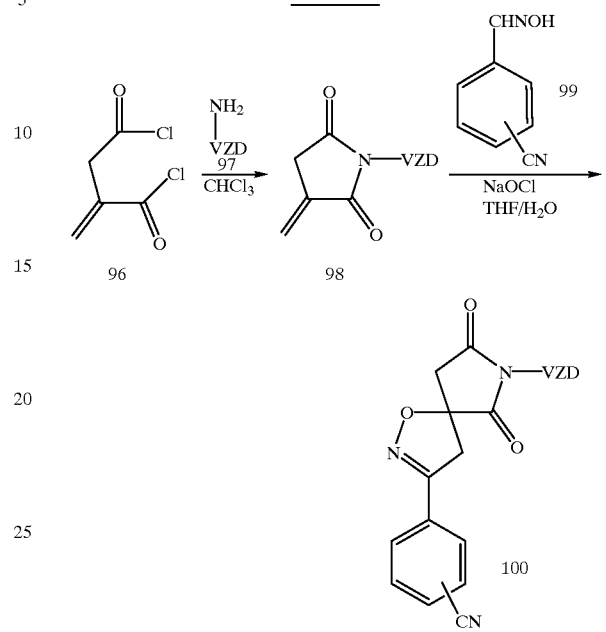

Some of the spiro-compounds of this invention in formula (II) may be prepared as shown in Scheme 23. Itaconyl chloride is reacted with appropiate amine to give the a-methylene-succinimide which then undergos 1,3-dipolar cycloaddition to yield the spiro-isoxazoline. Some of the spiro-compounds of this invention in formula (II) may be prepared from ester or acid intermediates. An example of this transformation is shown in Scheme 23. The ester or acid group in Scheme 24 can be reduced with $LiBH_4$ in THF or other reducing agents to give the alcohol. The alcohol is then cyclized using a mesylate intermediate to afford the desired spiro-compound. The alcohol can also be oxidized under Scheme 24

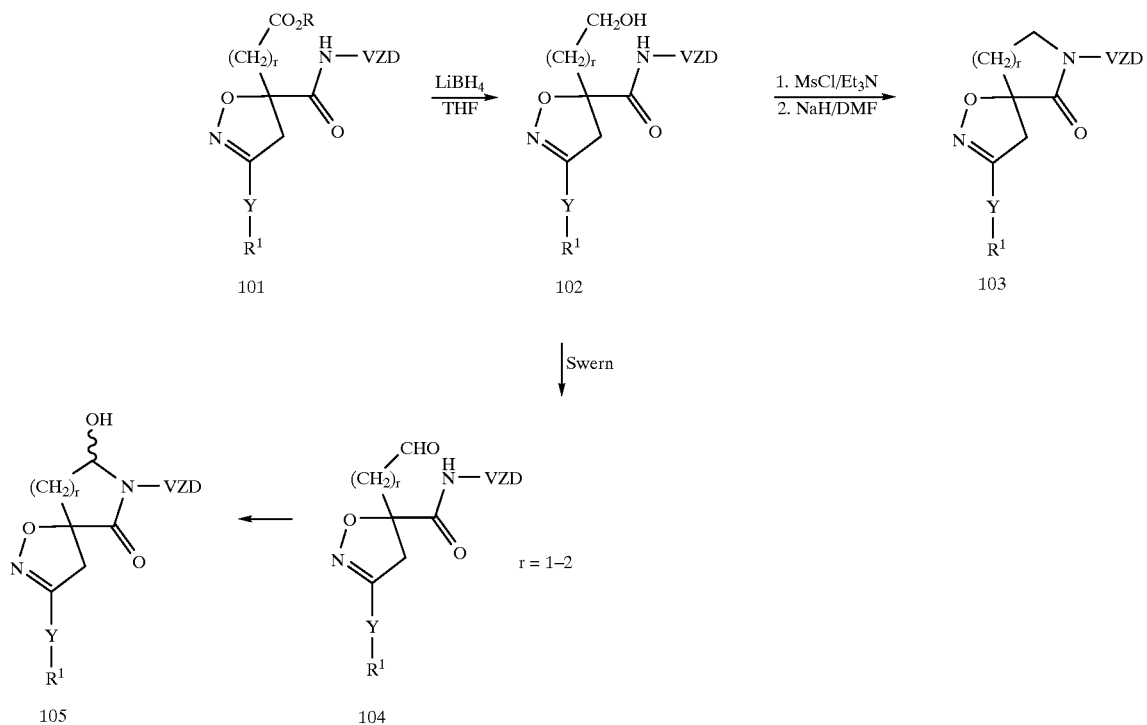

As used herein, the term "compound of formula I" or "compounds of this invention" includes pharmaceutically acceptable salts and prodrug forms of the compounds of formula I.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The compounds of this invention and their preparations can be understood further by the following examples which do not constitute a limitation of the invention. In these examples, unless otherwise indicated, all temperatures are in degrees centigrade and parts and percentages are by weight.

EXAMPLE 1

3-amidinophenyl-5-(4-amidinophenyl) aminocarbonyl-5-carbomethoxymethyl-isoxazoline, Bistrifluoroacetic Acid Salt Part A. Preparation of 3-cyanobenzaldehyde oxime 3-Cyanobenzaldehyde (25.0 g, 0.19 mol) and hydroxyamine hydrochloride (16.6 g, 0.24 mol) were added together with 100 mL of pyridine and 100 mL of ethanol. The mixture was stirred at room temperature under $N_2$ for 12 h. The mixture was concentrated to half of its volume and 200 mL of water was added. A white precipitate formed. It was filtered and dried to afford 25.9 g of the oxime (93%). $^1$HNMR (DMSO): d 7.61 (t, 1H); 7.85 (d, 1H); 7.96 (d, 1H); 8.00 (s, 1H); 8.21 (s, 1H); 11.61 (s, 1H).

Part B. Preparation of 3-(3-cyanophenyl)-5-carbomethoxy methyl-isoxazolin-5-ylcarboxylic acid 3-cyanobenzaldehyde oxime (26.9 g, 0.18 mol) and itaconic acid monomethyl ester (31.8 g, 0.22 mol) were added together with 600 mL of THF. To the above mixture was added bleach (467 mL of 0.67M aqueous solution) dropwise at room temperature. The reaction mixture was then stirred at RT under $N_2$ for 12 h. The THF was removed in vacuo. The aqueous mixture was diluted with aqueous NaOH and then extracted with ethyl acetate. After residual organic solvents were removed from the aqueous mixture, it was acidified with aqueous HCl. A white precipitate formed and it was filtered and dried to give 39.4 g of the desired product (74%). $^1$HNMR (DMSO): d 3.12 (m, 2H); 3.63 (s, 3H); 3.66 (d, 1H); 3.95 (d, 1H); 7.68 (t, 1H); 7.85 (d, 1H); 7.95 (d, 1H); 8.04 (d, 1H); 8.12 (s, 1H).

Part C. Preparation of 3-(3-cyanophenyl)-5-(4-cyanophenyl) aminocarbonyl-5-carbomethoxymethyl-isoxazoline 3-(3-Cyanophenyl)-5-carbomethoxy methyl-isoxazolin-5-ylcarboxylic acid (1.00 g, 3.47 mmol), 4-cyanoaniline (0.41 g, 3.47 mmol), and (2-(1H-benzotriazol-1-yl)-1,1,3,3-tetramethyluronium tetrafluoroborate (TBTU) (1.11 g, 3.47 mmol) were added together with DMF (25 mL) and triethylamine (2 mL). The mixture was stirred at room temperature under $N_2$ for 48 h. The reaction mixture was poured into water and extracted with ethyl acetate. The combined organic solution was washed with brine, dried over $MgSO_4$ and concentrated. It was then purified by chromatography (silica gel, 30–50% EtOAc in hexane) to give 0.33 g of the desired product (24%). MS 406, $(M+NH_4)^+$. $^1$HNMR $(CDCl_3)$: d 3.06 (d, 1H); 3.32 (d, 1H); 3.69 (s, 3H); 3.78 (q, 2H), 7.51–7.62 (m, 3H); 7.71 (d, 2H); 7.70 (s, 1H), 7.85 (d, 1H); 7.92 (s, 1H); 8.81 (s, 1H).

Part D. Preparation of 3-amidinophenyl-5-(4-amidinophenyl)-aminocarbonyl-5-carbomethoxymethyl-isoxazoline, Bistrifluoroacetic Acid Salt 3-(3-Cyanophenyl)-5-(4-cyanophenyl)aminocarbonyl-5-carbomethoxymethyl-isoxazoline (0.63 g, 1.62 mmol) was dissolved in 10 mL of anhydrous methanol and 30 mL of $CHCl_3$. The mixture was cooled in an ice-bath and HCl gas was bubbled-in until the solution was saturated. The reaction mixture was sealed and placed at 0° C. for 12 h. The reaction mixture was concentrated to dryness, and dried under vacuum. The resulting solid was dissolved in 20 mL of anhydrous methanol and ammonium acetate (0.77 g, 10 mmol) was added. The reaction mixture was sealed and stirred at RT for 12 h. The mixture was concentrated and precipitated with ether. The precipitate was filtered and purified by HPLC (C18 reversed phased) eluted with 0.5% TFA in $H_2O/CH_3CN$ to give 0.20 g of the bisbenzamidine TFA salt (20%). MS 423.2, $(M+H)^+$; 212.1, $(M+2H)^{2+}$. $^1$HNMR (DMSO-$d_6$): d 3.20 (m, 2H); 3.58 (s, 3H); 3.70–4.02 (m, 2H); 7.65–8.09 (m, 8H); 9.04 (s, 2H); 9.18 (s, 2H), 9.30 (s, 1H); 9.40 (s, 2H); 10.49 (s, 1H).

EXAMPLE 2

3-(3-Amidinophenyl)-5-[(2-naphthylsulfonyl)amino]methyl-isoxazoline Trifluoroacetic Acid Salt Part A. Preparation of 3-(3-cyanophenyl)-5-hydroxymethylisoxazoline 3-Cyanobenzaldehyde oxime (27.57 g, 0.189 mol) and allyl alcohol (21.95 g, 0.378 mol) were added together with 1000 mL of THF. The reaction mixture was cooled to 0° C. To the above mixture was added bleach (480 mL of 0.67M aqueous solution) dropwise. The reaction mixture was allowed to slowly warm to RT under $N_2$ for 12 h. The THF was removed in vacuo. The aqueous mixture was extracted with ethyl acetate. The combined organic extracts were triturated with diethyl ether. A white precipitate formed and it was filtered and dried to give 20.78 g of the desired product (54%). $^1$HNMR (DMSO-$d_6$): d 3.16–3.56 (m, 5H), 4.74 (m, 1H), 4.98 (t, 3H), 7.62 (t, 1H), 7.86 (dd, 1H), 7.98 (m, 1H).

Part B. Preparation of 3-(3-cyanophenyl)-5-(4-methylphenylsulfonyloxy)methylisoxazoline 3-(3-Cyanophenyl)-5-hydroxymethylisoxazoline (1.0 g, 4.95 mmol) and p-toluenesulfonyl chloride (0.95 g, 4.98 mmol) were dissolved in 5 mL of pyridine and stirred at RT under $N_2$ for 12 h. After diluting with saturated aqueous sodium bicarbonate, the mixture was extracted with ethyl acetate. The combined organic extracted were back-extracted with water, dried with $MgSO_4$, and then the solvent was removed in vacuo to give 1.53 g (87%) of the desired compound as a white solid. $^1$HNMR (DMSO-$d_6$): d 3.15 (dd, 1H), 3.51 (dd, 1H), 4.14 (m, 2H), 4.97 (m, 1H), 7.36 (m, 1H), 7.44 (d, 1H), 7.63 (t, 1H), 7.75 (m, 2H), 7.95 (m, 2H), 8.55 (d, 1H).

Part C. Preparation of 3-(3-cyanophenyl)-5-azidomethyl-isoxazoline 3-(3-Cyanophenyl)-5-(4-methylphenylsulfonyloxy)methylisoxazoline (1.00 g, 2.81 mmol) and sodium azide (0.55 g, 8.42 mmol) are dissolved in 10 mL of DMSO and stirred at RT under $N_2$ for 72 h. After diluting with water, the mixture was extracted with ethyl acetate, dried with $MgSO_4$, and then the solvent was removed in vacuo to give 0.64 g (100%) of the desired compound as a white solid. $^1$HNMR ($CDCl_3$): d 3.24 (dd, 1H), 3.46 (m, 2H), 3.61 (dd, 1H), 5.00 (m, 1H), 7.56 (t, 1H), 7.67 (d, 1H), 7.95 (m, 2H).

Part D. Preparation of 3-(3-cyanophenyl)-5-aminomethyl-isoxazoline 3-(3-Cyanophenyl)-5-azidomethylisoxazoline (0.64 g, 2.81 mmol) and 10% palladium on carbon (0.10 g) are added to 50 mL of ethanol and stirred at RT under $H_2$ for 4 h. The reaction mixture was filtered through celite and then the solvent was removed in vacuo to give 0.57 g (100%) of the desired compound as a white solid. $^1$HNMR ($CDCl_3$): d 2.90 (m, 1H), 3.06 (m, 1H), 3.18 (dd, 1H), 3.36 (dd, 1H), 4.88 (m, 1H), 7.32 (t, 1H), 7.48 (d, 1H), 7.95 (m, 2H).

Part E. Preparation of 3-(3-cyanophenyl)-5-[(2-naphthylsulfonyl)amino]methylisoxazoline 3-(3-Cyanophenyl)-5-aminomethylisoxazoline (0.56 g, 2.81 mmol) was dissolved in 20 mL of DMF and 2-naphthanenesulfonyl chloride (0.68 g, 3.00 mmol) and pyridine (0.48 mL, 6.2 mmol) were added. The reaction mixture was allowed to stir at RT under $N_2$ for 12 h. After diluting with saturated aqueous sodium bicarbonate, the mixture was extracted with ethyl acetate, dried with $MgSO_4$, and then the solvent was removed in vacuo. The crude product mixture was chromatographed on silica gel eluted with ethyl acetate/hexane (1:3) to give 0.30 g (27%) of the desired compound as a white solid. $^1$HNMR (DMSO-$d_6$): d 3.03 (m, 2H), 3.22 (dd, 1H), 3.49 (dd, 1H), 4.81 (m, 1H), 7.65 (m, 3H), 7.83–8.08 (m, 5H), 8.12 (m, 3H).

Part F. Preparation of 3-(3-amidinophenyl)-5-[(2-naphthylsulfonyl)amino]methylisoxazoline Trifluoroacetic Acid Salt 3-(3-Cyanophenyl)-5-[(2-naphthylsulfonyl)amino]methylisoxazoline (0.30 g, 0.77 mmol) was dissolved in 50 mL of MeOH. The reaction mixture was cooled in an ice/salt bath (−5° C.), and HCl gas was bubbled-in for 2 h. The mixture was sealed, allowed to warm to RT, and stirred for 12 h. The solvent was removed in vacuo and the resulting solid was dried and used in the next step.

The imidate formed above was added with ammonium carbonate (0.73 g, 7.6 mmol) to 50 mL of methanol. The mixture was sealed and stirred at RT for 12 h. The crude benzamidine was purified by HPLC (C18 reverse phase) eluted with 0.5% TFA in $H_2O/CH_3CN$ to give 0.03 g of the benzamidine TFA salt (9.5%). MS 409.3, $(M+H)^+$. $^1$HNMR (DMSO-$d_6$): d 3.03 (t, 2H), 3.22–3.58 (m, 2H) 4.82 (m, 1H), 7.67–7.73 (m, 3H), 7.85 (m, 2H), 7.95 (d, 1H), 8.06 (m, 2H), 8.11–8.18 (m, 3H), 9.27 (s, 1H), 9.43 (s, 1H).

EXAMPLE 3

4-amidinophenyl [3-(3-amidinophenyl)-5-Carbomethoxy-isoxazolin-5-yl]acetamide, Bistrifluoroacetic Acid Salt Part A. Preparation of N-4-cyanophenyl 3-carboxy-3-butenamide Itaconic anhydride (0.56 g, 5.0 mmol) and 4-cyanoaniline (0.71 g, 6.0 mmol) were added together with 25 mL of $CHCl_3$. The mixture was stirred at RT under $N_2$ for ½ h. It was then refluxed for 12 h. The mixture was cooled and the solid formed was filtered and dried (1.06 g, 92%). MS 248, $(M+NH_4)^+$.

Part B. Preparation of 4-cyanophenyl [3-(3-cyanophenyl)-5-carboxy-isoxazolin-5-yl]acetamide N-4-cyanophenyl 3-carboxy-3-butenamide (1.06 g, 4.6 mmol) and 3-cyanobenzaldehyde oxime (0.67 g, 4.6 mmol) were dissolved in 50 mL THF. Bleach (12 mL of 0.67M solution) was added dropwise at RT under $N_2$. The mixture was stirred at RT for 12 h. The solvent was removed in vacuo and the residue was dissolved in EtOAc. It was then washed with 0.1N HCl and brine, dried over $MgSO_4$ and concentrated to a solid. The solid was washed with $CH_2Cl_2$ to give 0.81 g off-solid (47%). MS 392, $(M+NH_4)^+$.

Part C. Preparation of 4-amidinophenyl [3-(3-amidinophenyl)-5-Carbometoxy-isoxazolin-5-yl]acetamide, Bistrifluoroacetic Acid Salt 4-cyanophenyl [3-(3-cyanophenyl)-5-carboxy-isoxazolin-5-yl]acetamide (0.30 g, 0.80 mmol) was dissolved in 20 mL of $CHCl_3$ and 10 mL of MeOH. It was cooled in an ice-bath and HCl gas was bubbled-in until the solution was saturated. It was sealed and stirred at RT for 12 h. The solvents were removed in vacuo and the resulting solid was then dried under vacuum. The solid was dissolved in 20 mL of MeOH and ammonium acetate (0.37 g) was added. The reaction mixture was sealed and stirred at RT for 12 h. It was concentrated and then precipitated with ether. The solid was filtered and then purified by HPLC (C18 reversed phased) eluted with 0.5% TFA in $H_2O/CH_3CN$ to give 84 mg of the bisbenzamidine TFA salt (16%). MS 423.2, $(M+H)^+$. $^1$HNMR (DMSO-$d_6$): d 3.72 (s, 3H); 3.60–4.09 (m, 4H); 7.70–8.10 (m, 8H); 8.90 (br.s, 1H); 8.95 (br.s, 1H), 9.20 (d, 2H); 9.40 (s, 1H); 10.68 (s, 1H).

EXAMPLE 4

3-(3-amidinophenyl)-5-[2'-aminosulfonyl-[1,1']-biphenyl-4-yl]aminocarbonyl-5-carbomethoxy methyl-isoxazoline, Trifluoroacetic Acid Salt Part A. Preparation of 2-(t-butylamino) sulfonylphenylboronic acid To a solution of 34.0 g (0.16 mol) of benzene-N-(t-butylsulfonamide in 500 mL of THF under $N_2$ was added 160 mL (0.36 mol) of 2.25M n-butyllithium in hexane over 35 min, keeping the temperature between 0°–2° C. The reaction mixture was allowed to warm to room temperature over 1.5 h, during which time a thick precipitate formed. Triisopropylborate (46 mL, 0.20 mol) was added, keeping the temperature below 35° C. After 1 h, the reaction mixture was cooled, 1N HCl (260 mL) was added, and the mixture was stirred for 30 min. After diluted with 520 mL of water, the mixture was extracted with 3×400 mL of ether. The combined organic extracts were extracted with 3×250 mL of 1N NaOH. The aqueous extracts were acidified to pH 1 with 6N HCl, and then extracted with 3×250 mL of ether. The ether extracts were washed with 250 mL of brine, dried over $MgSO_4$, and the solvents were removed in vacuo to yield 45 g of a thick oil. After addition of Toluene (45 mL), the mixture was agitated for 1h on the rotary evaporator. A small quantity of solid formed, which was used to induce partial solidification of the remaining crude product. Addition toluene (150 mL) was added, and the mixture was reduced to ½ volume in vacuo, keeping the temperature from 0°–10° C. The resulting precipitate was collected and washed with hexane, then dried under vacuum to give 24.6 g (60%) of the title compound as white crystals. m.p. 118°–119° C.

$^1$HNMR ($CDCl_3$): d 1.18 (s, 9H); 5.13 (s, 1H); 6.29 (br s, 2H); 7.53 (m, 2H); 7.82 (d, 1H); 8.00 (d, 1H).

Part B. Preparation of 2'-t-butylaminosulfonyl-4-nitro-[1,1']-biphenyl

A mixture of 4.4 g (0.020 mol) of 1-bromo-4-nitrobenzene and 5.14 g (0.020 mol) of 2-(t-butylamino) sulfonylphenylboronic acid , 1.16 g of tetrakis (triphenylphosphine) palladium(0) (0.001 mol), 0.32 g of tetrabutylammonium bromide (0.001 mol), and 20 mL of 2M aqueous sodium carbonate were refluxed with 180 mL of benzene under $N_2$ for 5.5 h. After cooling the mixture was diluted with methylene chloride and water. the two phases were separated and organic phase was washed with water and brine, dried over $MgSO_4$ and concentrated. The resulting solid was recrystallized from EtOAc/hexane to afford 3.25 g of the desired biphenyl.(49%). $^1$HNMR ($CDCl_3$): d 1.07(s, 9H); 3.60 (br s, 2H); 7.29 (d, 1H); 7.59 (m, 2H); 7.69 (d, 2H); 8.20 (d, 2H); 8.30 (d, 2H).

Part C. Preparation of 1-Bromo-4-t-butoxycarbonylaminobenzene

To a mixture of NaH (4.13, 0.14 mol) in THF was added 4-bromoaniline. The resulting mixture was refluxed under $N_2$ for 1 h. It was then cooled and di-t-butyl dicarbonate (33 g, 0.15 mol) was added. After stirred for ½ h, more NaH (4.13 g, 0.14 mol) was added and the reaction mixture was refluxed under $N_2$ overnight. The reaction mixture was cooled and carefully quenched with water. The mixture was extracted with ether. The combined organic solution was washed with saturated aqueous $NH_4Cl$ and saturated aqueous $NaHCO_3$, dried over $MgSO_4$, and concentrated. It was then purified by chromatography on silica gel eluted with hexane to yield 27.2 g of the desired product (80%). $^1$HNMR ($CDCl_3$): d 1.52 (s, 9H); 6.48 (br s, 1H); 7.27 (d, 2H); 7.40 (d, 2H).

Part D. Preparation of 2'-t-butylaminosulfonyl-4-amino-[1,1']-biphenyl

Method A:

A suspension of 3.00 g (0.009 mol) of 2'-t-butylaminosulfonyl-4-nitro-[1,1']-biphenyl and 0,30 g of 10% Pd/C in 90 mL of methanol was stirred at room temperature under $H_2$ (gas) (1 atm) for ½ h. The solubility of the starting material was very poor in methanol, so 60 mL of ethyl acetate was added and the mixture was stirred for 4 h. The reaction mixture was filtered through celite and the filtrate was concentrated. The crude product was recrystallized from benzene/hexane to give 2.32 g (85%) of the aniline.

$^1$HNMR ($CDCl_3$): d 0.99 (s, 9H); 3.72 (br s, 1H); 3.83 (br s, 2H); 6.76 (d, 1H); 7.27 (d, 1H); 7.33 (d, 2H); 7.43 (t, 1H); 7.53 (t, 1H); 8.14 (d, 1H). MS m/e 305 (M+H)$^+$.

Method B:

A mixture of 12.8 g (0.047 mol) of 1-Bromo-4-t-butoxycarbonylaminobenzene and 12.3 g (0.048 mol) of 2-(t-butylamino)sulfonylphenylboronic acid , 3.0 g of tetrakis(triphenylphosphine) palladium(0) (0.0026 mol), 0.80 g of tetrabutylammonium bromide (0.0024 mol), and 13.8 g (0.10 mol, in 30 ml of water) potassium carbonate were refluxed with 300 mL of toluene under $N_2$ for 6 h. The toluene was removed in vacuo and the residue was dissolved in methylene chloride and water. The two phases were separated and organic phase was washed with water and brine, dried over $MgSO_4$ and concentrated. the crude product was purified by chromatography on silica gel eluted with EtOAc/hexane (1:3) to afford 12.66 g of the desired biphenyl.(67%).

The protected aminobiphenyl compound (2.80 g, 6.9 mmol) was stirred with 10 mL of triflouroacetic acid and 20 mL of methylene chloride at room temperature for 2 h. The solvents were removed in vacuo. The residue was dissolved in methylene chloride and precipitated with hexane to give 1.20 g of the desired product as the TFA salt. $^1$HNMR (DMSO-$d_6$): d 1.01(s, 9H); 6.80 (s, 1H); 7.20–7.68 (m, 8H); 8.03 (d, 1H).

Part E. Preparation of 3-(3-cyanophenyl)-5-N-[2'-t-butylaminosulfonyl-[1,1']-biphenyl-4-yl]aminocarbonyl-5-carbomethoxy methyl-isoxazoline 3-(3-cyanophenyl)-5-carbomethoxy methyl-isoxazolin-5-ylcarboxylic acid (0.50 g, 1.73 mmol) was refluxed with 10 mL of acetonitrile and 0.76 mL (10.4 mmol) of thionyl chloride for 1 h under $N_2$. The solvent was removed in vacuo. Residual thionyl chloride was removed by adding toluene and then evaporating to dryness. The resulting solid was dissolved in 20 mL of THF and 2'-t-butylaminosulfonyl-4-amino-[1,1']-biphenyl, TFA salt (0.60 g, 1.40 mmol) was added followed by triethylamine (1.5 mL, 10.4 mmol). The reaction mixture was stirred at RT and the reaction was completed in less than 30 min. The mixture was diluted with ethyl acetate and the solution was washed with water and brine. It was dried over $MgSO_4$ and concentrated. The crude product mixture was chromatographed on silica gel eluted with methylene chloride/ethyl acetate (9:1) to give 0.57 g of the desired product (71%). MS 575.2, (M+H)$^+$. $^1$HNMR ($CDCl_3$): d 0.95 (s, 9H); 3.03 (d, 1H); 3.27 (d, 1H); 3.60 (d, 1H); 3.66 (s, 3H); 3.78 (d, 1H); 7.19 (d, 1H); 7.39–7.71 (m, 8H); 7.83 (d, 1H); 7.92 (s, 1H); 8.09 (d, 1H); 8.68 (s, 1H).

Part F. Preparation of 3-(3-cyanophenyl)-5-N-[2'-aminosulfonyl-[1,1']-biphenyl-4-yl]aminocarbonyl-5-carbomethoxy methyl-isoxazoline 3-(3-Cyanophenyl)-5-N-[2'-t-butylaminosulfonyl-[1,1']-biphenyl-4-yl]aminocarbonyl-5-carbomethoxy methyl-isoxazoline (1.12 g, 1.95 mmol) was refluxed with 25 ml of trifluoroacetic acid under $N_2$ for ½ h. The TFA was removed in vacuo, the residue was dissolved in methylene chloride and then precipitated with ether to give 1.0 g of white solid (99%). MS 519.2, (M+H)+. $^1$HNMR (CDCl$_3$): d 3.14 (d, 1H); 3.40 (d, 1H); 3.76 (s, 3H); 3.85 (dd, 2H); 4.40 (br s, 2H); 7.35 (d, 1H); 7.48–7.80 (m, 8H); 7.83 (d, 1H); 8.01 (s, 1H); 8.18 (d, 1H); 8.82 (s, 1H).

Part G. Preparation of 3-(3-amidinophenyl)-5-N-[2'-aminosulfonyl-[1,1']-biphenyl-4-yl]aminocarbonyl-5-carbomethoxy methyl-isoxazoline, Trifluoroacetic Acid Salt 3-(3-Cyanophenyl)-5-N-[2'-aminosulfonyl-[1,1']-biphenyl-4-yl]aminocarbonyl-5-carbomethoxy methyl-isoxazoline (1.2 g, 1.93 mmol) was dissolved in 90 mL of CHCl$_3$ and 20 mL of MeOH. The reaction mixture was cooled in an ice-bath, and HCl gas was bubbled-in for 30 min until the solution was saturated. The mixture was sealed and placed at 0° C. for 12 h. The solvents were removed in vacuo and the resulting solid was dried and used in the next step.

The imidate formed above was added with 0.92 g (12.0 mmol) of ammonium acetate and 30 mL of methanol. The mixture was sealed and stirred at RT for 12 h. The crude benzamidine was purified by HPLC (C18 reversed phased) eluted with 0.5% TFA in H$_2$O/CH$_3$CN to give 0.47 g of the benzamidine TFA salt (37%). MS 536.4, (M+H)+. $^1$HNMR (DMSO-d$_6$): d 3.20 (m, 2H); 3.48 (s, 3H); 3.70–4.01(m, 2H); 7.20–7.32 (m, 4H); 7.52 (m, 2H); 7.72 (d, 2H); 7.88 (d, 1H); 7.98 (d, 1H); 8.05 (d, 1H); 8.07 (s, 1H); 9.24 (s, 2H); 9.40 (s, 2H); 10.05 (s, 1H).

EXAMPLE 5 AND EXAMPLE 6

3-(3-amidinophenyl)-5-[[(2'-aminosulfonyl-[1,1']-biphenyl-4-yl)-methyl]aminocarbonyl]-5-(carbomethoxymethyl)isoxazoline, trifluoroacetic acid salt (Ex.5)

3-(3-amidinophenyl)-7-(2'-aminosulfonyl-[1,1']-biphenyl-4-yl)methyl[1-oxa-2,7-diazaspiro[4,4]non-2-ene-6,8-diones, trifluoroacetic acid salt (Ex.6)

Part A. Preparation of 2'-t-butylaminosulfonyl-4-aminomethyl-[1,1']-biphenyl

2'-t-butylaminosulfonyl-4-methyl-[1,1']-biphenyl (prepared by the same method described in Part B of Example 1) (1.57 g, 5.18 mmol) was refluxed with N-bromosuccinamide (0.92 g, 5.18 mmol) and AIBN (0.10 g) in 50 mL of CCl$_4$ for 2 h. The mixture was cooled and the precipitae was filtered-off. The filtrate was concentrated to an off-white solid. The resulting solid was dissovled in 20 mL of DMF and sodium azide (0.67 g, 10.3 mmol) was added. the mixture was heated to 100° C. for 6 h under N$_2$. The reaction mixture was cooled and pourted into water. It was extracted with EtOAc. The combined organic solution was washed with brine and dried over MgSO$_4$. It was the concentrated to a white solid. this solid was the added together with 0.2 g of Pd(OH), 0.5 mL of concentrated HCl, and 100 mL of MeOH. The mixture was placed under balloon H$_2$ for 5 h. The resulting mixture was filtered through celite and washed with MeOH. The filtrate was concentrated and precipitated with Et$_2$O to give 1.32 g of white solid (72%). MS (DCI) 336 (M+NH$_4$)+, 319 (M+H)+.

Part B. Preparation of 3-(3-cyanophenyl)-5-N-[2'-t-butylaminosulfonyl-[1,1']-biphenyl-4-methyl]aminocarbonyl-5-carbomethoxy methyl-isoxazoline This compound was prepared by the same method described in Part G of Example 4 using 2'-t-butylaminosulfonyl-4-aminomethyl-[1,1']-biphenyl and 3-(3-cyanophenyl)-5-carbomethoxy methyl-isoxazolin-5-ylcarboxylic acid as the starting materials. MS (DCI) 606 (M+NH$_4$)+.

Part C. Preparation of 3-(3-amidinophenyl)-5-[[(2'-aminosulfonyl-[1,1']-biphenyl-4-yl)-methyl]aminocarbonyl]-5-(carbomethoxymethyl)isoxazoline, trifluoroacetic acid salt (EX 5) and 3-(3-amidinophenyl)-7-(2'-aminosulfonyl-[1,1']-biphenyl-4-yl)methyl[1-oxa-2,7-diazaspiro[4,4]non-2-ene-6,8-diones,trifluoroacetic acid salt (EX 6).

3-(3-cyanophenyl)-5-N-[2'-t-butylaminosulfonyl-[1,1']-biphenyl-4-methyl]aminocarbonyl-5-carbomethoxy methyl-isoxazoline was subjected to the Pinner—amidine reaction protocol described in Part D of Example 1. The crude product mixture was purified by HPLC (C18 reversed phased) eluted with 0.5% TFA in H$_2$O and CH$_3$CN to give Compounds Ex 5 and Ex 6 as the TFA salts. Ex 5: MS (ESI) 518.4, (M+H)+. Ex 6: MS (ESI) 550.4, (M+H)+.

EXAMPLE 7

3-(3-amidinophenyl)-5-[(4-benzenesulfonylphenyl-1-yl)aminocarbonyl]-5-(carbomethoxymethyl) isoxazoline, trifluoroacetic acid salt Part A: Preparation of 4-aminodiphenylsulphone To a suspension of 4-nitrodiphenylsulphone (1.00 g, 3.80 mmol) and Pd-C (61.6 mg, 5%) in MeOH (50 mL) was added 3N aqueous HCl (1.30 mL, 3.90 mmol). The mixture was placed under H$_2$ at 50 psi for 4 h. It was filtered through celite and washed with MeOH. The filtrate was concentrated and preticipated with ether to give 0.79 g of pale orange solid (77%). MS 234.1, (M+H)+. $^1$HNMR (DMSO-d$_6$): d 6.61 (d, 2H); 6.85 (br. s, 2H); 7.55 (m, 5H), 7.81 (d, 2H).

Part B: Preparation of 3-(3-cyanophenyl)-5-[(4-benzenesulfonylphenyl-1-yl)aminocarbonyl]-5-(carbomethoxymethyl)isoxazoline This compound was prepared by the method described in Part C of Example 1 using 3-(3-cyanophenyl)-5-carbomethoxy methyl-isoxazolin-5-ylcarboxylic acid and 4-aminodiphenylsulphone as starting materails. MS 504.2, (M+H)+. $^1$HNMR (CDCl$_3$): d 3.02–3.34 (m, 2H), 3.69 (s, 3H); 3.78 (m, 2H), 7.48 (t, 3H); 7.52 (t, 1H), 7.75 (d, 3H); 7.90 (m, 6H); 8.78 (br. s, 1H).

Part B: Preparation of 3-(3-amidinophenyl)-5-[(4-benzenesulfonylphenyl-1-yl)aminocarbonyl]-5-(carbomethoxymethyl)isoxazoline, trifluoroacetic acid This compound was prepared as described in Part D of Example 1. MS 521 2, (M+H)+.

EXAMPLE 8

3-(3-amidinophenyl)-5-(2'-aminosulfonyl-[1,1']-biphenyl-4-yl)aminocarbonyl-5-(tetrazol-1-yl) methyl-isoxazoline, Trifluoroacetic Acid Salt Part A. Preparation of 3-(3-cyanophenyl)-5-Carbomethoxy-5-(tetrazol-1-yl)methyl-isoxazoline 1H-Tetrazole(0.89 g, 14.0 mmol) and K$_2$CO$_3$ were added together with 50 mL of DMF. Methyl 2-(bromomethyl) acrylate (2.5 g, 14.0 mmol) was added. The mixture was stirred at room temperature under N$_2$ for 12 h. The mixture was poured into water and extracted with EtOAc. The combined organic solution was washed with brine, dried over MgSO$_4$, and then concentrated to give 1.63 g of methyl 2-(tetrazolemethyl)acrylate. This crude product mixtre was added together with 3-cyanobenzaldehyde oxime prepared as described in Example 1 (1.42 g, 9.69 mmol) and THF (50 mL). To the above mixture was added dropwise bleach (25 mL of 0.67M solution). The resulting mixture was stirred at room temperature under N$_2$ for 3 h. The THF was removed. The mixture was diluted with water and extracted with EtOAc. The combined organic solution was washed with brine, dried over MgSO$_4$, and concentrated. It was purified by chromatography (silica gel, 5–15% EtOAc in CH$_2$Cl$_2$) to give 1.61 g of the desired product and 0.50 g of the regioisomer 3-(3-cyanophenyl)-5-Carbomethoxy-5-(tetrazol-2-yl)methyl-isoxazoline. $^1$HNMR (DMSO-d$_6$): δ 3.78 (s, 3H); 3.80–4.10 (q, 2H); 5.09–5.20 (q, 2H); 7.68 (t, 1H); 7.98 (d, 1H); 8.07 (s, 1H); 9.45 (s, 1H). MS(ES+) 313.1 (M+H)$^+$.

Part B. Preparation of 3-(3-cyanophenyl)-5-Carboxylic acid-5-(tetrazol-1-yl)methyl-isoxazoline 3-(3-Cyanophenyl)-5-Carbomethoxy-5-(tetrazol-1-yl-methyl)-isoxazoline (1.60 g, 5.12 mmol) was added together with 75 mL of THF. LiOH (12 mL of 0.5 M aqueous solution) was added. The mixture was stirred at room temperature under N$_2$ for 1 h. The THF was removed. The mixture was diluted with water and acidified with concentrated HCl. It was extracted with EtOAc. The combined organic solution was washed with brine, dried over MgSO$_4$, and concentrated to a white solid (1.54 g). $^1$HNMR (DMSO-d$_6$): δ 3.70–4.02 (q, 2H); 5.02–5.18 (q, 2H); 7.67 (t, 1H); 7.97 (d, 1H); 8.04 (s, 1H); 9.42 (s, 1H). MS(ES+) 299 (M+H)$^+$.

Part C. Preparation of 3-(3-cyanophenyl)-5-[2'-t-Butylaminosulfonyl-[1,1']-biphenyl-4-yl]aminocarbonyl-5-(tetrazol-1-yl)methyl-isoxazoline 3-(3-Cyanophenyl)-5-Carboxylic acid-5-(tetrazol-1-yl) methyl-isoxazoline (0.55 g, 1.84 mmol) was refluxed with CH$_3$CN (20 mL) and SOCl$_2$ (1.34 mL, 18.4 mmol) under N$_2$ for 1 h. The solvent was removed. Residual SOCl$_2$ was removed by dissolving in toluene and then removing the solvent to dryness. The resulting solid was dissolved in CH$_2$Cl$_2$ (20 mL). 2'-t-Butylaminosulfonyl-4-amino-[1,1']-biphenyl prepared as described in Example 4 (0.28 g, 0.92 mmol) was added followed by Et$_3$N (1.5 mL, 18.4 mmol). The mixture was stirred at room temperature under N$_2$ for ½ h. It was diluted with CH$_2$Cl$_2$ and washed with water and brine. It was dried over MgSO$_4$ and concentrated. The desired product was the purified by chromatography (silica gel, 20% EtOAc in CH$_2$Cl$_2$) to give 0.59 g off-white solid. $^1$HNMR (DMSO-d$_6$): δ 1.01 (s, 9H); 3.90–4.10 (q, 2H); 5.08–5.16 (q, 2H); 6.70 (s, 1H), 7.24–7.38 (m, 3H); 7.50–7.77(m, 5H), 7.98–8,03 (m, 3H); 8.12 (s, 1H); 9.42 (s, 1H). MS(ES$^+$) 585.2 (M+H)$^+$.

Part D. Preparation of 3-(3-amidinophenyl)-5-[2'-aminosulfonyl-[1,1']-biphenyl-4-yl]aminocarbonyl-5-(tetrazol-1-yl)methyl-isoxazoline, Trifluoroacetic Acid Salt 3-(3-Cyanophenyl)-5-[2'-t-Butylaminosulfonyl-[1,1']-biphenyl-4-yl]aminocarbonyl-5-(tetrazol-1-yl)methyl-isoxazoline (0.41 g, 0.70 mmol) was dissolved in anhydrous CHCl$_3$ (20 mL) and anhydrous CH$_3$OH (5 mL). HCl gas was bubbled-in until the solution was saturated (about 15 min). The reaction mixture was sealed and placed in a refrigerator for 12 h. The solvents were removed. The resulting solid was dried under vacuum. The imidate formed above was dissolved in 20 mL of anhydrous CH$_3$OH. Ammonium acetate (0.55 g, 7.0 mmol) was added. The mixture was sealed and stirred at room temperature for 12 h. The solvent was removed. The solid was dissolved in CH$_3$CN/H$_2$O/TFA, and purifed by reversed phase HPLC (C$_{18}$ reversed phase column, 0.5% TFA in H$_2$O/CH$_3$CN) to give the desired TFA salt (0.15 g). $^1$HNMR (DMSO-d$_6$): δ 3.89–4.16 (q, 2H); 5.13–5.31 (q, 2H); 7.22–7.48 (m, 5H), 7.52–7.78(m, 5H), 7.91 (d, 1H); 8.00–8,08 (m, 3H); 9.12 (s, 2H); 9.41 (s, 2H); 9.43 (s, 1H). MS(ES$^+$) 546.3 (M+H)$^+$.

EXAMPLE 9

3-(3-amidinophenyl)-5-(2'-aminosulfonyl-[1,1']-biphenyl-4-yl)oxymethyl-5-ethoxymethyl-isoxazoline, Trifluoroacetic Acid Salt Part A. Preparation of 3-(3-cyanophenyl)-5-ethoxymethyl-5-(4-bromophenoxy)methyl-isoxazoline Sodium hydride (0.74 g of 60% oil dispersion, 18.4 mmol) was washed with Petrolium ether and then suspended in 50 mL of THF. To it was added 4-bromophenol (2.89 g, 16.7 mmol). The mixture was stirred at room temperature for 15 min, and methyl 2-(bromomethyl)acrylate (2.99 g, 16.7 mmol) was added. The mixture was stirred at room temperature under N$_2$ for 12 h. The reaction was quenched with ethanol and the solvents were removed. The resulting material was dissovled in EtOAc and washed with water and brine. It was dried over MgSO$_4$ and concentrated to 3.93 g of methyl 2-[(4-bromophenoxy)methyl]acrylate.

Methyl 2-[(4-bromophenoxy)methyl]acrylate (2.01 g, 7.4 mmol) was dissolved in 50 mL of THF. The mixture was cooled at −78° C. under N$_2$ and DIDAL-H (12.3 mL, 18.5 mmol) was added. The mixture was stirred for 1 h at −78° C. and 1 h at −20° C., and then quenched carefully with ethanol and the solvents were removed. The resulting material was dissovled in EtOAc and washed with water and brine. It was dried over MgSO$_4$ and concentrated. Column chromatography on silica gel (4:1 hexane/EtOAc) gave 0.21 g of corresponding alcohol.

Sodium hydride (0.11 g of 60% oil dispersion, 4.4 mmol) was washed with Petrolium ether and then suspended in 30 mL of THF. The mixture was stirred at room temperature for 15 min, and ethyl iodide (0.62 g, 4.0 mmol) was added. The mixture was refluxed under N$_2$ for 12 h. The reaction was quenched with ethanol and the solvents were removed. The resulting material was dissovled in EtOAc and washed with water and brine. It was dried over MgSO$_4$, concentrated, chromatographed on silica gel (4:1 hexane/EtOAc) to give 0.38 g of 2-[(4-bromophenoxy)methyl]-2-(ethoxymethyl) alkene.

2-[(4-Bromophenoxy)methyl]-2-(ethoxymethyl)alkene (0.38 g, 1.4 mmol) and 3-cyanobenzaldehyde oxime prepared as described in Example 1 (0.21 g, 1.4 mmol) were dissolved in THF (10 mL). Clorox bleach (3.6 mL of 0.67M) was added dropwise. The mixture was stirred at room temperature under N$_2$ for 12 h. It was diluted with EtOAc and washed with brine. The organic mixture was dried over MgSO$_4$, concentrated, and recrystalized from EtOAc/hexane to give 0.48 g of 3-(3-cyanophenyl)-5-ethoxymethyl-5-(4-bromophenoxy)methyl-isoxazoline.

Part B. Preparation of 3-(3-cyanophenyl)-5-[2'-t-Butylaminosulfonyl-[1,1']-biphenyl-4-yl]oxymethyl-5-ethoxymethyl-isoxazoline 3-(3-Cyanophenyl)-5-ethoxymethyl-5-(4-bromophenoxy)methyl-isoxazoline (0.48 g, 1.15 mmol), 2-(t-butylaminosulfonylphenyl) boronic acid prepared as described in Example 4 (0.38 g, 1.49 mmol), tetrabutyl ammonium bromide (0.062 g, 0.054 mmol), sodium carbonate (0.36 g, 3.4 mmol), water (3.0 mL), and benzene (50 mL) were added. Nitrogen gas was bubbled through the mixture for 5 min and tetrakis(triphenylphosphine)palladium was added. The mixture was refluxed under N$_2$ for 12 h. The solvents were removed. The resulting material was dissovled in EtOAc and washed with water and brine. It was dried over MgSO$_4$, concentrated, chromatographed on silica gel (3:1 hexane/EtOAc) to give 0.18 g of the desired product. $^1$HNMR (CDCl$_3$): δ 1.00 (s, 9H); 1.21(t, 3H); 3.43 (m, 2H); 3.73–3.80 (m, 5H); 4.20 (m, 2H); 7.00 (d, 2H); 7.27 (d, 1H); 7.42 (d, 2H); 7.46–7.58 (m, 3H); 7.71 (d, 1H); 7.98 (m, 2H); 8.15 (d, 1H).

Part C. Preparation of 3-(3-amidinophenyl)-5-[2'-aminosulfonyl-[1,1']-biphenyl-4-yl]oxymethyl-5-ethoxymethyl-isoxazoline, trifluoroacetic acid salt.

3-(3-Cyanophenyl)-5-[2'-t-Butylaminosulfonyl-[1,1']-biphenyl-4-yloxymethyl-5-ethoxymethyl-isoxazoline (0.18 g, 0.32 mmol) was dissolved in 50 mL of anhydrous methanol. It was cooled to −20° C. and HCl gas was bubbled in until the solution was saturated. The mixture was sealed and allowed to stand at 0° C. for 12 h. The solvent was removed and the solid was dried under vacuum. The resulting solid was dissolved in 50 mL of anhydrous methanol, and ammonium carbonate (0.15 g, 1.6 mmol) was added. The mixture was stirred for 48 h. The solvent was removed. The solid was purified by by reversed phase HPLC ($C_{18}$ reversed phase column, 0.5% TFA in $H_2O/CH_3CN$) to give 0.13 g of the desired TFA salt (0.15 g). $^1$HNMR (DMSO-$d_6$): δ 1.09 (s, 3H); 3.40–3.58 (m, 4H); 3.68 (q, 2H); 4.17 (q, 2H); 6.93 (d 2H); 7.15 (s, 2H); 7.28(m, 3H), 7.46–7.59(m, 2H), 7.68 (t, 1H); 7.83 (d, 1H); 7.82–8.10 (m, 3H); 9.30 (s, 2H); 9.39 (s, 2H). MS(ES$^+$) 509.4 (M+H)$^+$.

EXAMPLE 10 AND EXAMPLE 11

3-(3-amidinophenyl)-4-(2'-aminosulfonyl-[1,1']-biphenyl-4-yl)aminocarbonyl-5-methyl-isoxazoline, Trifluoroacetic Acid Salt 3-(3-amidinophenyl)-5-(2'-aminosulfonyl-[1,1']-binhenyl-4-yl)aminocarbonyl-4-methyl-isoxazoline, Trifluoroacetic Acid Salt Part A. Preparation of 3-(3-cyanophenyl)-5-Carbomethoxy-4-methyl-isoxazoline and 3-(3-cyanophenyl)-4-Carbomethoxy-5-methyl-isoxazoline To a dichloromethane (100 mL) solution of 3-cyanophenyl-oximinochloride (2.30 g, 13.65 mmol) and methyl crotonate (1.71 g, 17.05 mmol) was added triethylamine (1.39 g, 13.65 mmol) in dichloromethane (5 mL) dropwise over 0.5 h. The reaction mixture was stirred at room temperature for 12 h. It was then concentrated to a viscous oil. Chromatography (silica gel, hexane: ethyl acetate 8:2) afforded the desired 4-methylcarboxylate-isoxazoline (0.82 g, 25% yield) as a colorless oil. $^1$HNMR (CDCl$_3$) δ 1.47 (d, J=9 Hz, 3H), 3.77 (s, 3H), 4.09 (d, J=4.2 Hz, 1H), 5.15 (m, 1H), 7.54 (t, 1H), 7.68 (d, J=7.8 Hz, 2H), 7.94 (d, J=8 Hz, 2H). MS(ESI) 245, (M+H)$^+$. The 5-methylcarboxylate isoxazoline was also obtained (0.53 g, 16% yield) as a colorless oil. $^1$HNMR(CDCl$_3$) δ 1.42 (d, J=8.5 Hz, 3H), 3.81 (s, 3H), 3.96 (m, 1H), 4.83 (d, J=4.5 Hz, 1H), 7.55 (t, 1H), 7.70 (d, J=8.0 Hz, 2H), 7.95 (d, J=7.9 Hz, 2H). MS(ESI) 245, (M+H)$^+$.

Part B. Preparation of 3-(3-cyanophenyl)-4-Carboxylic acid-5-methyl-isoxazoline

The 4-isoxazoline ester was then carefully hydrolyzed (LiOH, 1eq.) in THF:water (4:1, 20 mL) to the carboxylic acid (0.75 g, 97% yield). $^1$HNMR(CDCl$_3$) δ 1.50 (d, J=8 Hz, 3H), 4.07 (d, J=7 Hz, 1H), 5.18, (m, 1H), 7.50 (t, 1H), 7.68 (d, J=8 Hz, 2H), 7.97 (d, J=8 Hz, 2H). MS(ESI) 231 (M+H)$^+$.

Part C. Preparation of 3-(3-cyanophenyl)-4-(2'-t-butylaminosulfonyl-[1,1']-biphenyl-4-yl)aminocarbonyl-5-methyl-isoxazoline Treatment of the acid from Part C with oxalyl chloride (1 eq) in dichloromethane followed by addition of a drop of DMF. Reaction mixture was stirred at room temperature for 1.5 h and then concentrated to a yellow oil. This was then redissolved in dichloromethane followed by treatment with 2'-t-Butylaminosulfonyl-4-amino-[1,1']-biphenyl prepared as described in Example 4 (1 eq) and triethyl amine (3 eq.).

The reaction mixture was stirred at room temperature overnight The reaction mixture was poured into water (100 mL) and then extracted with ethyl acetate (2×100 mL), It was washed with brine (50 mL) and dried (magnesium sulfate). Evaporation of the solvent afforded crude amide which was purified (column chromatography, silica gel $CH_2Cl_2$:MeOH, 9:1) to give 0.35 g (20% yield) colorless oil. $^1$HNMR (CDCl$_3$) δ 1.01 (s, 9H), 1.52 (d, J=6.5 Hz, 3H), 3.70 (s, 1H), 4.18 (d, J=5.4 Hz, 1H), 5.18 (m, 1H), 7.27 (dd, J=3 and 8 Hz, 1H), 7.43–7.54 (m, 7H), 7.68 (d, J=8.5 Hz, 1H), 8.03 (ds, 2H), 8.17 (sd, 2H). MS (DCI–NH$_3$) 534 (M+NH$_4$)$^+$.

Part D. Preparation of 3-(3-amidinophenyl)-4-(2'-aminosulfonyl-[1,1']-biphenyl-4-yl)aminocarbonyl-5-methyl-isoxazoline The nitrile obtained in Part D was then subjected to the Pinner—amidine reaction protocol described previously to afford 0.15 g (colorless crystals) of the desired benzamidine compound after reversed phase HPLC purification. $^1$HNMR (DMSO $d_6$) δ 1.44 (d, J=7.5 Hz, 3H), 4.53 (d, J=6 Hz, 1H), 5.02 (m, 1H), 7.27–7.38 (m, 5H), 7.55–7.63 (m, 3H), 7.70 (t, 1H0, 7.80 (d, J=8.5 Hz, 1H), 7.91 (d, J=8.2 hz, 1H), 8.00 (dd, J=1.8 and 7.9 Hz, 1H), 9.10 (bs, 2H), 9.44 (bs, 2H), 10.30 (s, 1H). MS (ESI) 478.3, (M+H)$^+$.

Part E. Preparation of 3-(3-amidinophenyl)-5-(2'-aminosulfonyl-[1,1']-biphenyl-4-yl)aminocarbonyl-4-methyl-isoxazoline This compound was obtained by the same procedure described above using 3-(3-cyanophenyl)-4-Carbomethoxy-5-methyl-isoxazoline as starting material. $^1$HNMR(DMSO $d_6$) δ 1.38 (d, J=7.7 Hz, 3H), 4.31 (m, 1H), 5.08 (d, J=5.4 Hz, 1H), 7.23–7.38 (m, 5H), 7.55–7.66 (m, 2H), 7.69–7.70 (m, 2H), 7.88 (d, j=8 Hz, 1H), 8.00 (d, j=8 Hz, 1H), 8.10 (ds, 2H), 9.20 (bs, 2H0, 9.40 (bs, 2H), 10.3 (s, 1H). MS(ESI) 478.4, (M+H)$^+$.

EXAMPLE 12

3-(3-amidinophenyl)-5-[(4-(2'-nitronhenoxy))phenyl-1-yl]aminocarbonyl-5-methyl-isoxazoline, Trifluoroacetic Acid Salt Part A. Preparation of 4-(2'-nitrophenoxy)aniline To a stirred DMF (10 mL) solution of p-aminophenol (0.89 g, 8.16 mmol) was added anhydrous potassium carbonate (6.76 g, 48.96 mmol). The reaction mixture was stirred at room temperature for 1 h and then 2-fluoronitrobenzene (1.152 g, 8.16 mmol) aws added. The reddish brown solution was refluxed for 24 h. The reaction mixture was cooled and then quenched with water (200 mL). It was extracted with EtOAc, washed with brine(50 mL), and dried with magnesium sulfate. Evaporation of the solvent provided a crude material which was purified via column chromatography (silica gel 9:1, hexane:ethyl acetate) to a colorless oil 1.10 g (58% yield); $^1$HNMR (CDCl$_3$) δ 3.60 (bs, 2H), 6.65 (d, J=8.2 Hz, 2H), 6.88 (d, J=8.0 Hz, 2H), 7.06 (t, 1H), 7.40 (t, 1H), 7.98 (d, J=8.0 Hz, 1H). MS (DCI–NH$_3$) 248 (M+NH$_4$, 100).

Part B. Preparation of 3-(3-amidinophenyl)-5-[(4-(2'-nitrophenoxy))phenyl-1-yl]aminocarbonyl-5-methyl-isoxazoline 3-(3-Cyanophenyl)-5-carboxylic acid-5-methyl-isoxazoline prepared by the same procedures described above aws coupled to 4-(2-nitrophenoxy)aniline from Part A as previously described. The resulting product was subjected to standard Pinner reaction to give the desired amidine. $^1$HNMR(DMSO $d_6$) δ 7.74 (s, 3H), 3.48 (d, J=19 Hz, 1H), 4.04 (d, J=19 Hz, 1H), 7.04 (dd, J=2.5 and 8 Hz, 3H), 7.33 (t, 1H), 7.64–7.77 (m, 3H), 7.78 (d, J=8.5 Hz, 1H), 7.87 (d, J=7.5 Hz, 1H), 8.03 (t, 3H), 9.20 (bs, 2H), 9.41 (bs, 2H), 10.2(s, 1H). MS(ESI) 460.2, (M+H, 100).

EXAMPLE 13

3-(3-amidinophenyl)-5-(3-[NN-ethyl(pyrid-2-yl-methyl)]aminophenyl-1-yl)aminocarbonyl-5-methyl-isoxazoline, Trifluoroacetic Acid Salt Part A. Preparation of 3-[NN-ethyl(pyrid-2-yl-methyl)] aniline The title compound was prepared in three step sequence via a sequential reductive amination of 3-nitroaniline with 2-pyridine carboxaldehyde and acetaldehyde with sodium cycanoborohydride in methanol, followed by catalytic (Pd/C) hydrogenation in 29% overall yield. $^1$HNMR(CDCl$_3$) δ 1.30 (t, 3H), 3.60 (q, 2H), 4.70 (s, 2H), 6.91 (dd, 1H), 7.05–7.30 (m, 3H), 7.50 (m, 2H), 7.65 (t, 1H), 8.60 (d, 1H). MS(ESI) 258, (M+H, 100).

Part B. Preparation of 3-(3-amidinophenyl)-5-(3-[NN-ethyl(pyrid-2-yl-methyl)]aminophenyl-1-yl)aminocarbonyl-5-methyl-isoxazoline, Trifluoroacetic Acid Salt 3-(3-Cyanophenyl)-5-carboxylic acid-5-methyl-isoxazoline prepared by the same procedures described above was coupled to 3-[NN-ethyl(pyrid-2-yl-methyl)] aniline from Part A as previously described. The resulting product was subjected standard Pinner reaction to give the desired amidine. $^1$HNMR(DMSO d$_6$) δ 1.12 (t, 3H), 1.70 (s, 3H), 3.40 (–3.49(dm, J=19.6 Hz, 3H), 4.00 (d, J=19.6 Hz, 1H), 4.60 (s, 2H), 6.34 (dd, J=2.5 and 8 Hz, 1H), 6.99 (t, 1H), 7.04 (d, J=8.6 Hz, 1H), 7.19 (s, 1H), 7.40 (d, J=8.4 Hz, 1H), 7.36 (m, 1H), 7.70 (t, 1H), 7.80 (m, 2H), 8.05 (ds, 2H), 8.58 (d, J=4.4 Hz, 1H), 9.06 (bs, 2H), 9.40 (bs, 2H), 9.80 (s, 1H). High resolution mass spectrum calcd. for C$_{26}$H$_{29}$N$_6$O$_2$ 457.235199, found 457.233965.

The compounds of Tables 1–6 were prepared by the methods of Examples 1–13. The compounds in Tables 1–6 which have asymmetric centers are racemates except where indicated otherwise by (+) or (–) in the column headed o.r. (for optical rotation) in Table 2.

TABLE 1

I-1

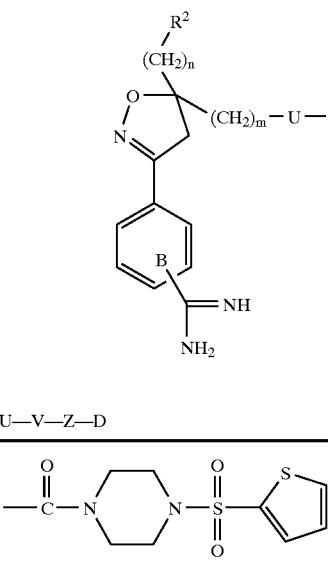

| EX # | B | m | (CH$_2$)$_n$R$^2$ | —U—V—Z—D | MS (M + H)$^+$ |
|---|---|---|---|---|---|
| 14 | p | 1 | H | 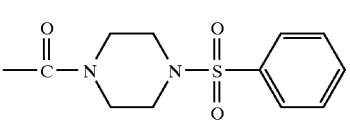 | 462 |
| 15 | p | 1 | H | 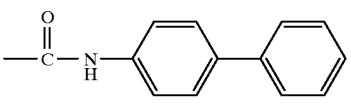 | 456 |
| 16 | p | 1 | H | 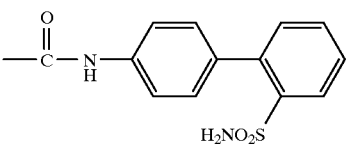 | 399.0 |
| 17 | p | 1 | H | 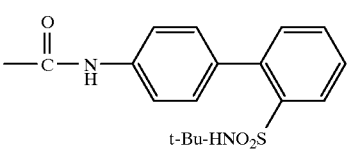 | 478.3 |
| 18 | p | 1 | H | (see below) | 534.3 |

TABLE 1-continued

I-1

| EX # | B | m | $(CH_2)_nR^2$ | —U—V—Z—D | MS $(M + H)^+$ |
|---|---|---|---|---|---|
| 19 | p | 1 | H | (acetamide-CH2-biphenyl with H2NO2S) | 492.0 |
| 20 | p | 1 | H | (acetamide-phenyl-amidine, para) | 365.2 |
| 21 | p | 1 | H | (acetamide-phenyl-amidine, meta) | 365.3 |
| 22 | m | 1 | H | (acetamide-phenyl-amidine, meta) | 365.3 |
| 23 | m | 1 | H | (acetamide-phenyl-amidine, para) | 365.3 |
| 24 | p | 1 | $CONH_2$ | (acetamide-phenyl-amidine, meta) | 408.2 |

TABLE 1-continued
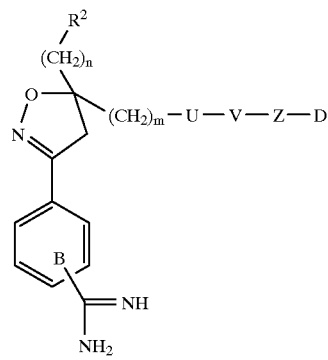
I-1
| EX # | B | m | (CH₂)ₙR² | —U—V—Z—D | MS (M + H)⁺ |
|---|---|---|---|---|---|
| 25 | m | 0 | CH₂CO₂Me | —C(O)—NH—(3-C₆H₄)—C(=NH)NH₂ | 423.3 |
| 26 | m | 0 | CH₂CO₂H | —C(O)—NH—(3-C₆H₄)—C(=NH)NH₂ | 409.2 |
| 27 | m | 0 | H | —C(O)—NH—(4-C₆H₄)—C(=NH)NH₂ | 351.3 |
| 28 | m | 0 | CH₂CONHCH₂CO₂Me | —C(O)—NH—(4-C₆H₄)—C(=NH)NH₂ | 480.5 |
| 29 | m | 0 | CH₂CO₂H | —C(O)—NH—(4-C₆H₄)—C(=NH)NH₂ | 409.3 |
| 30 | p | 0 | CO₂Me | —C(O)—NH—(3-C₆H₄)—C(=NH)NH₂ | 423.3 |
| 31 | m | 0 | CH₂CO₂Me | —C(O)—NH—(4-C₆H₄)—SO₂NH₂ | 460.3 |

TABLE 1-continued
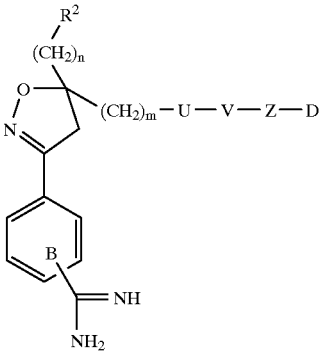
I-1
| EX # | B | m | (CH₂)ₙR² | —U—V—Z—D | MS (M + H)⁺ |
|------|---|---|----------|----------|-------------|
| 32 | m | 0 | CH₂CO₂Me | 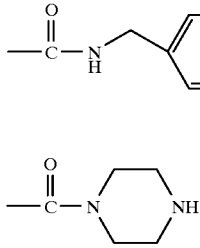 | 219.2 (M + 2H)²⁺ |
| 33 | m | 0 | CH₂CO₂Me | 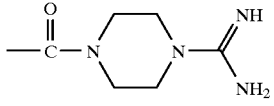 | 374.2 |
| 34 | m | 0 | CH₂CO₂Me | 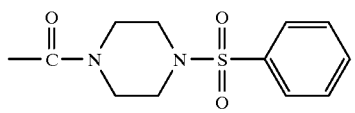 | 416.4 |
| 359 | m | 0 | CH₂CO₂Me | 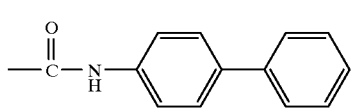 | 514.3 |
| 36 | m | 0 | CH₂CO₂Me | 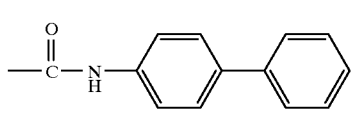 | 457.4 |
| 37 | m | 0 | CH₂CO₂H | 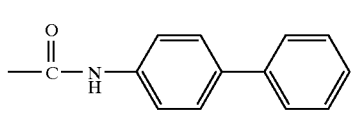 | 443.4 |
| 38 | m | 0 | CH₂CONH₂ | 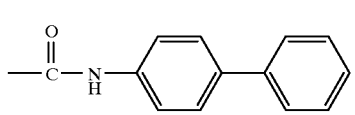 | 442.4 |
| 39 | m | 0 | CH₂CH₂OH | | 429.3 |

TABLE 1-continued

I-1

[Structure: isoxazoline core with R²-(CH₂)ₙ and (CH₂)ₘ—U—V—Z—D substituents at the 5-position, connected at the 3-position to a phenyl ring B bearing a C(=NH)NH₂ amidine group]

| EX # | B | m | (CH₂)ₙR² | —U—V—Z—D | MS (M + H)⁺ |
|------|---|---|----------|-----------|--------------|
| 40 | m | 0 | CH₂CO₂Me | —C(=O)—NH—C₆H₄—C₆H₄—NH₂ | 236.8 (M + 2H)²⁺ |
| 41 | m | 0 | CH₂CONH₂ | —C(=O)—NH—CH₂—C₆H₄—C₆H₄(2-SO₂NH₂) | 535.4 |
| 42 | m | 0 | CH₂CO₂Me | —C(=O)—NH—C₆H₄—C₆H₄(2-SO₂NH-t-Bu) | 592.5 |
| 43 | m | 0 | CH₂CONH₂ | —C(=O)—NH—C₆H₄—C₆H₄(2-SO₂NH-t-Bu) | 577.5 |
| 44 | m | 0 | CH₂CO₂H | —C(=O)—NH—C₆H₄—C₆H₄(2-SO₂NH₂) | 522.4 |
| 45 | m | 0 | CH₂CONH₂ | —C(=O)—NH—C₆H₄—C₆H₄(2-SO₂NH₂) | 521.4 |

TABLE 1-continued

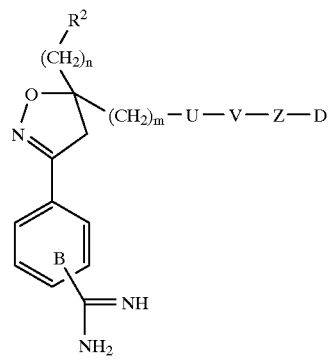

I-1

| EX # | B | m | (CH$_2$)$_n$R$^2$ | —U—V—Z—D | MS (M + H)$^+$ |
|---|---|---|---|---|---|
| 46 | m | 0 | CH$_2$CH$_2$OH | 4'-sulfamoylbiphenyl-4-ylcarbamoyl | 508.2 |
| 47 | m | 0 | CH$_2$CH$_2$OMe | 4'-sulfamoylbiphenyl-4-ylcarbamoyl | |
| 48 | m | 0 | CH$_2$CONHCH$_2$CO$_2$Me | 4'-sulfamoylbiphenyl-4-ylcarbamoyl | 593.3 |
| 49 | m | 0 | CH$_2$CONH(CH$_2$)$_2$-4-imidazole | 4'-sulfamoylbiphenyl-4-ylcarbamoyl | 308.2 (M + 2H)$^{2+}$ |
| 50 | m | 0 | CH$_2$CO$_2$Me | 4'-sulfamoyl-5'-n-Pr-biphenyl-4-ylcarbamoyl | 578.3 |
| 51 | m | 0 | CH$_2$CO$_2$Me | 2'-sulfamoyl-3-Me-biphenyl-4-ylcarbamoyl | 550.3 |

TABLE 1-continued

I-1

[Structure: isoxazoline core with R² on (CH₂)ₙ branch, O-N ring, (CH₂)ₘ—U—V—Z—D substituent, attached to phenyl-B-C(=NH)NH₂]

| EX # | B | m | (CH₂)ₙR² | —U—V—Z—D | MS (M + H)⁺ |
|------|---|---|----------|-----------|-------------|
| 52 | m | 0 | CH₂CO₂H | [2-methyl-4-(2-sulfamoylphenyl)phenyl]amido | 536.5 |
| 53 | m | 0 | CH₂CONH₂ | [2-methyl-4-(2-sulfamoylphenyl)phenyl]amido | 535.3 |
| 54 | m | 0 | CH₂CONHCH₂CO₂Me | [2-methyl-4-(2-sulfamoylphenyl)phenyl]amido | 607.3 |
| 55 | m | 0 | CH₂CO₂Me | [6-(2-sulfamoylphenyl)pyridin-3-yl]amido | 537.2 |
| 56 | m | 0 | CH₂CO₂Me | [5-(2-sulfamoylphenyl)pyridin-2-yl]amido | 537.2 |

TABLE 1-continued

I-1

[Structure: isoxazoline core with R² group, (CH₂)ₙ, (CH₂)ₘ-U-V-Z-D substituent, B-phenyl-amidine]

| EX # | B | m | (CH₂)ₙR² | —U—V—Z—D | MS (M + H)⁺ |
|------|---|---|----------|----------|-------------|
| 57 | m | 0 | CH₂CO₂Me | -C(O)-NH-(pyrimidin-2-yl)-5-(2-H₂NO₂S-phenyl) | 538.2 |
| 58 | m | 0 | CH₂CO₂Me | -C(O)-NH-(3-F-4-(2-H₂NO₂S-phenyl)phenyl) | 554.2 |
| 59 | m | 0 | CH₂CO₂Me | -C(O)-NH-(4-(2-H₂NO₂S-3-Me-phenyl)phenyl) | — |
| 60 | m | 0 | CH₂CO₂Me | -C(O)-NH-(4-(2-F₃C-phenyl)phenyl) | 525.3 |
| 61 | m | 0 | CH=CHCO₂Me | -C(O)-NH-(2-Me-4-(2-H₂NO₂S-phenyl)phenyl) | 562.3 |

TABLE 1-continued
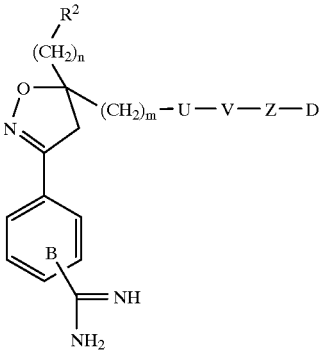
I-1
| EX # | B | m | (CH$_2$)$_n$R$^2$ | —U—V—Z—D | MS (M + H)$^+$ |
|---|---|---|---|---|---|
| 62 | | m | 0 | CH$_2$CH$_2$CO$_2$Me | 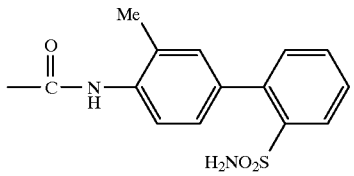 | 564.2 |
| 63 | | m | 0 | CH$_2$CO$_2$Me | 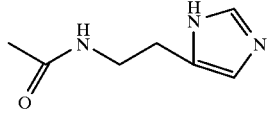 | 226.7 (M + 2H)$^{2+}$ |
| 64 | | m | 0 | CH$_2$CO$_2$Me | 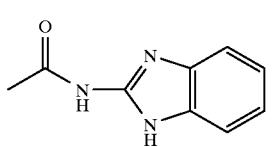 | 200.2 (M + 2H)$^{2+}$ |
| 65 | | m | 0 | CH$_2$CO$_2$Me | 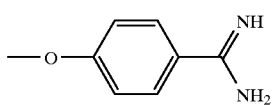 | 211.2 (M + 2H)$^{2+}$ |
| 66 | | m | 1 | H | 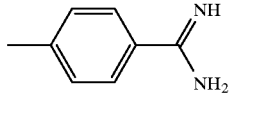 | 169.1 (M + 2H)$^{2+}$ |
| 67 | | m | 2 | H |  | 168.6 (M + 2H)$^{2+}$ |

TABLE 2

I-2

| EX # | o.r. | m | X | Y | (CH₂)ₙR² | R¹² | MS (M + H)⁺ |
|---|---|---|---|---|---|---|---|
| 68 | | 0 | N | N | CH₂CO₂Me | o-SO₂NH₂ | 538.2 |
| 69 | | 0 | CH | N | CH₂CO₂Me | o-SO₂NH₂ | 537.2 |
| 70 | (+) | 0 | N | N | CH₂CO₂Me | o-SO₂NH₂ | 538.2 |
| 71 | (−) | 0 | N | N | CH₂CO₂Me | o-SO₂NH₂ | 538.2 |
| 72 | | 0 | CF | CH | CH₂CO₂Me | o-SO₂NH₂ | 554.2 |
| 73 | | 0 | CF | CH | CH₂CO₂H | o-SO₂NH₂ | 540.2 |
| 74 | | 0 | CH | CH | H | o-SO₂NH₂ | 464.2 |
| 75 | | 0 | CH | N | CH₃ | o-SO₂NH₂ | 479.3 |
| 76 | | 0 | CH | CH | CH₃ | o-SO₂NH₂ | 478.2 |
| 77 | | 0 | CH | N | CH₂OMe | o-SO₂NH₂ | 509.2 |
| 78 | | 0 | N | N | CH₂SEt | o-SO₂NH₂ | 540.3 |
| 79 | | 0 | N | N | CH₂SO₂Et | o-SO₂NH₂ | 572.4 |
| 80 | | 0 | CH | N | CH₂SO₂Et | o-SO₂NH₂ | 571.3 |
| 81 | | 0 | CH | CH | CH₂SO₂Et | o-SO₂NH₂ | 570.4 |
| 8 | | 0 | CH | CH | CH₂-tetrazol-1-yl | o-SO₂NH₂ | 546.3 |
| 82 | | 0 | CH | CH | CH₂-tetrazol-1-yl | o-SO₂NH-t-Bu | 602.3 |
| 83 | | 0 | CH | CH | CH₂-tetrazol-2-yl | o-SO₂NH₂ | 546.5 |
| 84 | | 0 | CH | CH | CH₂-tetrazol-2-yl | o-SO₂NH-t-Bu | 602.6 |
| 85 | | 0 | CH | N | CH₂CO₂H | o-SO₂NH₂ | 523.1 |
| 86 | (−) | 0 | CH | N | CH₂CO₂Me | o-SO₂NH₂ | 537.1 |
| 87 | (+) | 0 | CH | N | CH₂CO₂Me | o-SO₂NH₂ | 537.3 |
| 88 | | 0 | N | N | CH₂OMe | o-SO₂NH₂ | 510.3 |
| 89 | | 0 | N | N | CH₂OEt | o-SO₂NH₂ | 524.3 |
| 90 | | 0 | CH | N | CH₂OEt | o-SO₂NH₂ | 523.3 |
| 91 | | 0 | CH | CH | CH₂CONH₂ | o-SO₂NH₂ | 520.6 |
| 92 | | 0 | CH | CH | CH₂OMe | o-SO₂NH₂ | 508.3 |
| 93 | | 0 | CH | CH | CH₂OEt | o-SO₂NH₂ | 522.3 |
| 94 | (−) | 0 | CH | CH | CH₂OEt | o-SO₂NH₂ | 522.4 |
| 95 | (+) | 0 | CH | CH | CH₂OEt | o-SO₂NH₂ | 522.4 |
| 96 | (+) | 0 | CH | CH | CH₂OEt | o-SO₂NH-t-Bu | 578.5 |
| 97 | | 0 | CH | N | CH₂CO₂H | o-SO₂NH₂ | 524.4 |
| 98 | | 0 | CH | CH | CH₂O-i-Pen | o-SO₂NH₂ | 564.4 |
| 99 | | 0 | CH | CH | CH₂Br | o-SO₂NH₂ | 556.3 |
| 100 | | 0 | CH | CH | CH₂Br | o-SO₂NH-t-Bu | 612.4 |
| 101 | | 0 | CH | CH | CH₂OEt | o-SO₂NHMe | 536.4 |
| 102 | (−) | 0 | CH | N | CH₂OEt | o-SO₂NH₂ | 523.3 |
| 103 | (−) | 0 | CH | N | CH₂OEt | o-SO₂NH-t-Bu | 579.3 |
| 104 | | 0 | CH | CH | CH₂O-n-Pr | o-SO₂NH₂ | 536.4 |
| 105 | | 0 | CH | CH | CH₂O-n-Bu | o-SO₂NH₂ | 550.5 |
| 106 | | 0 | CH | N | CH₂SEt | o-SO₂NH₂ | 539.3 |
| 107 | | 0 | CH | CH | CF₃ | o-SO₂NH-t-Bu | 588.2 |
| 108 | | 0 | CH | CH | CF₃ | o-SO₂NH₂ | 532.3 |
| 109 | (−) | 0 | CH | CH | CH₂-tetrazol-1-yl | o-SO₂NH₂ | 546.4 |
| 110 | (+) | 0 | CH | CH | CH₂-tetrazol-1-yl | o-SO₂NH₂ | 546.2 |
| 111 | (−) | 0 | CCl | CH | CH₂-tetrazol-1-yl | o-SO₂NH₂ | 580.1 |
| 112 | | 0 | CCl | CH | CH₂-tetrazol-1-yl | o-SO₂NH₂ | 580.1 |
| 113 | | 0 | CF | CH | CH₂-tetrazol-1-yl | o-SO₂NH₂ | 564.4 |
| 114 | (−) | 0 | CF | CH | CH₂-tetrazol-1-yl | o-SO₂NH₂ | 564.4 |
| 115 | | 0 | CH | N | CH₂-tetrazol-1-yl | o-SO₂NH-t-Bu | 603.5 |
| 116 | | 0 | CH | N | CH₂-tetrazol-1-yl | o-SO₂NH₂ | 547.4 |
| 117 | (−) | 0 | CH | N | CH₂-tetrazol-1-yl | o-SO₂NH₂ | 547.4 |
| 118 | | 0 | CH | CH | CH₂CH₂OMe | o-SO₂NH₂ | 522.4 |
| 119 | | 0 | CH | CH | CH₂CH₂OMe | o-SO₂NH-t-Bu | 578.5 |
| 120 | (−) | 0 | CH | N | CH₂-tetrazol-1-yl | o-SO₂NH-t-Bu | 603.6 |
| 121 | | 0 | CH | CH | CH₂Ph | o-SO₂NH₂ | 554.3 |
| 122 | | 0 | CH | CH | CH₂O-i-Pr | o-SO₂NH₂ | 536.3 |
| 123 | (−) | 0 | CH | N | CH₂OMe | o-SO₂NH₂ | 509.3 |
| 124 | (−) | 0 | CH | N | CH₂OMe | o-SO₂NH-t-Bu | 565.4 |
| 125 | | 0 | CH | N | CH₂-tetrazol-1-yl | o-SO₂NHMe | 561.6 |
| 126 | (−) | 0 | CH | N | CH₂-tetrazol-1-yl | o-SO₂NHMe | 561.6 |
| 127 | (−) | 0 | CH | CH | CH₂-tetrazol-1-yl | o-SO₂NH-n-Pr | 588.6 |
| 128 | | 0 | CH | CH | CH₂-tetrazol-1-yl | o-SO₂NH-n-Pr | 588.4 |
| 129 | (−) | 0 | CH | CH | CH₂-tetrazol-1-yl | o-SO₂NHMe | 560.4 |
| 130 | | 0 | CH | CH | CH₂I | o-SO₂NH₂ | 604.3 |

TABLE 2-continued

I-2

[Structure: 3-amidinophenyl-substituted isoxazoline with (CH₂)ₙR² and (CH₂)ₘ-CO-NH-pyridyl-phenyl-R¹² substituents]

| EX # | o.r. | m | X | Y | (CH₂)ₙR² | R¹² | MS (M + H)⁺ |
|---|---|---|---|---|---|---|---|
| 131 | | 0 | CH | CH | CH₂-1-(4,5-dichloroimidazole) | o-SO₂NHMe | 612.2 |
| 132 | | 0 | N | N | CH₂-tetrazol-1-yl | o-SO₂NH₂ | 548.4 |
| 133 | | 1 | CH | CH | CO₂Me | o-SO₂NH₂ | 536.3 |
| 134 | | 1 | CH | CH | CO₂Me | o-SO₂NH-t-Bu | 592.4 |
| 135 | | 1 | CH | N | CO₂H | o-SO₂NH₂ | 523.4 |
| 136 | (−) | 1 | N | N | CO₂H | o-SO₂NH₂ | 524.3 |
| 137 | (−) | 1 | CH | N | CO₂H | o-SO₂NH₂ | 523.4 |
| 138 | | 1 | N | N | CO₂H | o-SO₂NH₂ | 524.4 |
| 139 | | 0 | CH | CH | CH₂CO₂Me | o-OMe | 487.3 |
| 140 | | 0 | CH | CH | CH₂CO₂Me | m-OMe | 487.3 |
| 141 | | 0 | CH | CH | CH₂CONH₂ | o-OMe | 472.2 |
| 142 | | 0 | CH | CH | CH₂CONH₂ | m-OMe | 472.2 |
| 143 | | 0 | CH | CH | CH₂CO₂Me | m-CF₃ | 525.2 |
| 144 | | 0 | CH | CH | CH₂CONH₂ | m-CF₃ | 510.2 |
| 145 | | 0 | CH | CH | CH₂CONH₂ | m-SO₂Me | 535.3 |
| 146 | | 0 | CH | CH | CH₂CONH₂ | o-Me | 456.5 |
| 147 | | 0 | CH | CH | CH₂CO₂Me | o-Me | 471.5 |
| 148 | | 0 | CH | CH | CH₂CONH₂ | m-Me | 456.5 |
| 149 | | 0 | CH | CH | CH₂CO₂Me | m-Me | 471.5 |
| 150 | | 0 | CH | CH | CH₂CO₂Me | m-SO₂NH₂ | 536.5 |
| 151 | | 0 | CH | CH | CH₂CONH₂ | o-SO₂NMe₂ | 549.4 |
| 152 | | 0 | CH | CH | CH₂CONH₂ | o-SO₂NHMe | 535.4 |
| 153 | | 0 | CH | CH | CH₂CO₂Me | o-SMe | 503.4 |
| 154 | | 0 | CH | CH | CH₂CO₂Me | o-SO₂Me | 535.4 |
| 155 | | 1 | CH | CH | CO₂Me | o-SO₂Me | 535.4 |
| 156 | | 0 | CH | CH | CH₂CONH₂ | o-CO₂Me | 500.3 |
| 157 | | 0 | CH | CH | CH₂CO₂Me | o-CO₂Me | 515.4 |
| 158 | | 0 | CH | CH | CH₂CONH₂ | o-SOMe | 488.3 |
| 159 | | 0 | CH | CH | CH₂OMe | o-SO₂Me | 507.4 |
| 160 | | 0 | CH | CH | CH₂OMe | o-SO₂Et | 521.4 |
| 161 | | 0 | CH | CH | CH₂OMe | o-SO₂-n-Pr | 535.4 |
| 162 | | 0 | CH | CH | CH₂OMe | o-SO₂-i-Bu | 549.5 |
| 163 | | 0 | CH | CH | CH₂-tetrazol-1-yl | o-SO₂Me | 545.2 |
| 164 | | 0 | CH | CH | CH₂-tetrazol-1-yl | o-SO₂CF₃ | |
| 165 | (−) | 0 | CH | CH | CH₂-tetrazol-1-yl | o-CF₃ | 535.4 |
| 166 | (−) | 0 | N | CH | CH₂-tetrazol-1-yl | o-CF₃ | 536.3 |
| 167 | | 0 | N | N | CH₂-tetrazol-1-yl | o-CF₃ | |
| 168 | | 0 | CCl | CH | CH₂-tetrazol-1-yl | o-CF₃ | |
| 169 | | 0 | CF | CH | CH₂-tetrazol-1-yl | o-CF₃ | |
| 170 | | 0 | CH | CH | CH₂-imidazol-1-yl | o-CF₃ | |
| 171 | | 0 | CH | CH | CH₂-imidazol-1-yl | o-SO₂NH₂ | |

TABLE 3

I-3

| EX # | U | (CH$_2$)$_n$R$^2$ | V—(Z)$_u$—(D)$_u$ | MS (M + H)$^+$ |
|---|---|---|---|---|
| 172 | CONH | CH$_2$OMe | 4'-methyl-4-fluoro-2-sulfamoylbiphenyl | 526.4 |
| 173 | CONH | CH$_3$ | 4'-methyl-2-sulfamoylbiphenyl | 478.3 |
| 174 | CONH | CH$_3$ | 4'-methyl-2-(N,N-bis(methanesulfonyl)amino)biphenyl | 570.3 |
| 175 | CONH | CH$_3$ | 4-(pyridin-2-yl)phenyl | 400.3 |
| 176 | CONH | CH$_3$ | 4-(pyridin-3-yl)phenyl | 400.2 |
| 177 | CONH | CH$_3$ | 4-(3-nitropyridin-2-yl)phenyl | 445.4 |
| 178 | CONH | CH$_3$ | 4-(neopentyloxy)phenyl | 409.3 |
| 179 | CONH | CH$_3$ | 4-(N-neopentylsulfamoyl)phenyl | 472.4 |

TABLE 3-continued

I-3

[Structure: 3-amidinophenyl-isoxazoline with (CH$_2$)$_n$R$^2$ and U—V—(Z)$_u$—(D)$_u$ substituents at 5-position]

| EX # | U | (CH$_2$)$_n$R$^2$ | V—(Z)$_u$—(D)$_u$ | MS (M + H)$^+$ |
|---|---|---|---|---|
| 180 | CONH | CH$_3$ | 4-phenoxyphenyl | 415.3 |
| 181 | CONH | CH$_3$ | 4-(pyridin-3-yloxy)phenyl | 416.4 |
| 182 | CONH | CH$_3$ | 4-(3-aminophenoxy)phenyl | 430.3 |
| 183 | CONH | CH$_3$ | 4-(2-aminophenoxy)phenyl | 430.3 |
| 184 | CONH | CH$_3$ | 4-[2-(N-methylsulfamoyl)phenoxy]phenyl | 508.4 |
| 12 | CONH | CH$_3$ | 4-(2-nitrophenoxy)phenyl | 462.2 |
| 185 | CONH | CH$_2$OCH$_3$ | 4-[2-(methoxycarbonylthio)phenoxy]phenyl | 523.3 |

TABLE 3-continued
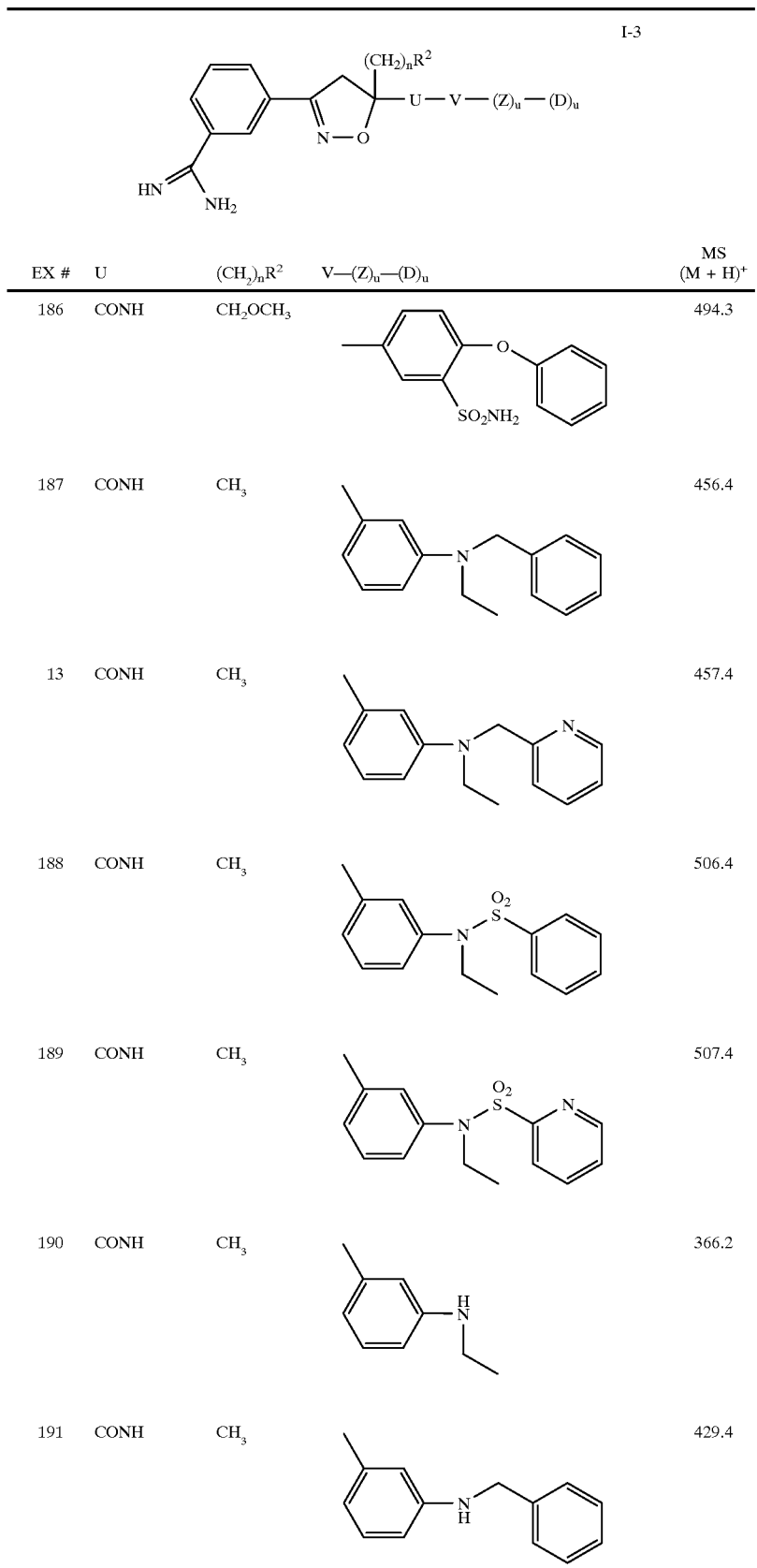
| EX # | U | $(CH_2)_nR^2$ | V—$(Z)_u$—$(D)_u$ | MS $(M + H)^+$ |
|---|---|---|---|---|
| 186 | CONH | $CH_2OCH_3$ | 5-methyl-2-phenoxy-phenyl with $SO_2NH_2$ | 494.3 |
| 187 | CONH | $CH_3$ | 3-methylphenyl-N(ethyl)-CH_2-phenyl | 456.4 |
| 13 | CONH | $CH_3$ | 3-methylphenyl-N(ethyl)-CH_2-pyridyl | 457.4 |
| 188 | CONH | $CH_3$ | 3-methylphenyl-N(ethyl)-SO_2-phenyl | 506.4 |
| 189 | CONH | $CH_3$ | 3-methylphenyl-N(ethyl)-SO_2-pyridyl | 507.4 |
| 190 | CONH | $CH_3$ | 3-methylphenyl-NH-ethyl | 366.2 |
| 191 | CONH | $CH_3$ | 3-methylphenyl-NH-CH_2-phenyl | 429.4 |

TABLE 3-continued

I-3

[Structure: 3-(amidinophenyl)-isoxazoline with 5-substituents (CH₂)ₙR² and U—V—(Z)ᵤ—(D)ᵤ]

| EX # | U | (CH₂)ₙR² | V—(Z)ᵤ—(D)ᵤ | MS (M + H)⁺ |
|------|------|----------|-------------|-------------|
| 192 | CONH | CH₂CO₂Me | 3'-methyl-biphenyl-3-SO₂NH₂ | 536.2 |
| 193 | CONH | CH₂CO₂Me | 5-methyl-2-(2-sulfamoylphenyl)pyridine | 537.2 |
| 194 | CONH | CH₂CO₂Me | methyl-6H-benzo[c]chromen-6-one | 499.1 |
| 195 | CONH | CH₂OEt | 5-methyl-2-(2-sulfamoylphenyl)thiophene | 528.3 |
| 196 | CONH | CH₂OEt | 5-methyl-2-(2-(SO₂NH-t-Bu)phenyl)thiophene | 584.4 |
| 197 | CH₂ | CH₂OEt | 4'-methyl-biphenyl-2-SO₂NH₂ | 493.2 |
| 198 | CH₂O | H | 4'-methyl-biphenyl-2-SO₂NH₂ | 451.2 |

TABLE 3-continued
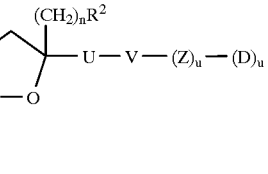
I-3
| EX # | U | $(CH_2)_nR^2$ | V—$(Z)_u$—$(D)_u$ | MS $(M + H)^+$ |
|---|---|---|---|---|
| 9 | $CH_2O$ | $CH_2OEt$ | 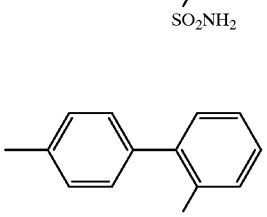 | 509.2 |
| 199 | $CH_2CH_2O$ | H | | 465.4 |
| 200 | $CH_2NH$ | H | 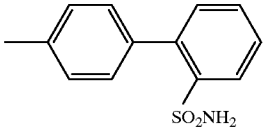 | 450.3 |
| 201 | $CH_2NCOCF_3$ | H | 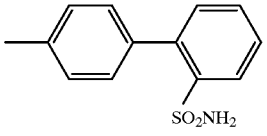 | 563.3 |
| 202 | $CH_2CO$ | H | 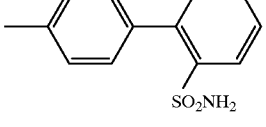 | 463.3 |

TABLE 4

I-4

| EX# | R | A | B | MS (M + H)+ |
|---|---|---|---|---|
| 10 | H | 4-AcNH-C6H4-(2-SO2NH2-C6H4)- | CH3 | 478.3 |
| 203 | H | 4-AcNH-C6H4-(2-SO2NH2-C6H4)- | CH3OCH2 | 508.4 |
| 204 | H | 4-AcNH-C6H4-(2-SO2NH2-C6H4)- | tetrazole-1-yl-CH2— | 546.4 |
| 205 | H | 4-AcNH-C6H4-(2-SO2NH2-C6H4)- | CF3 | 532.3 |
| 206 | H | 4-AcNH-C6H4-(2-SO2NH2-C6H4)- | Si(Et)2Me | 564.4 |
| 207 | 4-CH2OCH3 | 4-AcNH-C6H4-(2-SO2NH2-C6H4)- | CH3 | 522.3 |
| 11 | H | CH3 | 4-AcNH-C6H4-(2-SO2NH2-C6H4)- | 478.3 |
| 208 | H | CH3OCH2 | 4-AcNH-C6H4-(2-SO2NH2-C6H4)- | 508.4 |

TABLE 4-continued

I-4

[Structure: phenyl-amidine group attached to isoxazoline ring with substituents A, R, B]

| EX# | R | A | B | MS (M + H)+ |
|-----|---|---|---|-------------|
| 209 | H | CF$_3$ | [4'-acetamido-biphenyl-2-sulfonamide] | 532.3 |
| 210 | 5-OCH$_2$OCH$_3$ | CH$_3$ | [4'-acetamido-biphenyl-2-sulfonamide] | 522.3 |

TABLE 5

| EX# | Structures | MS (M + H)+ |
|-----|------------|-------------|
| 211 | [spiro isoxazoline-pyrrolidinone with OMe substituent, N-biphenyl] | 441.3 |
| 212 | [spiro isoxazoline-pyrrolidinedione with N-(4'-sulfamoylbiphenyl)] | 504.3 |
| 213 | [spiro isoxazoline-pyrrolidinedione with N-(4'-sulfamoylbiphenyl)] | 504.3 |

TABLE 5-continued

| EX# | Structures | MS (M + H)+ |
|---|---|---|
| 214 | 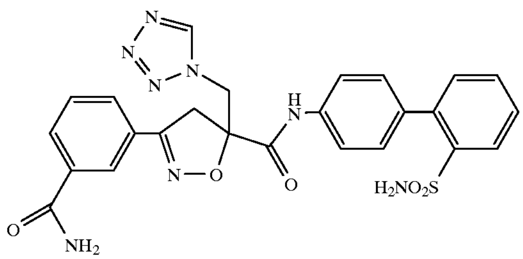 | |
| 215 | 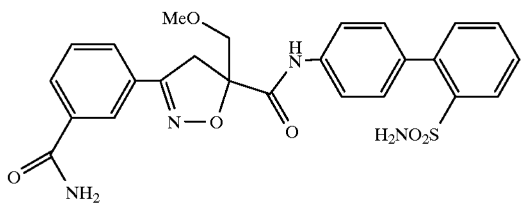 | |
| 216 | 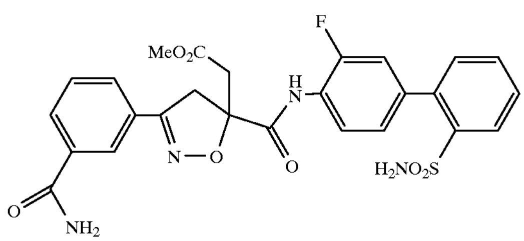 | |
| 217 | 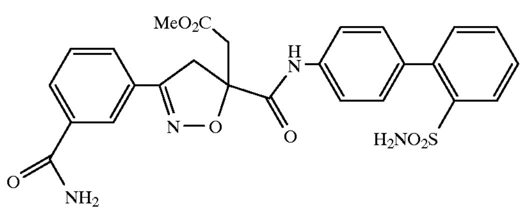 | |
| 218 | 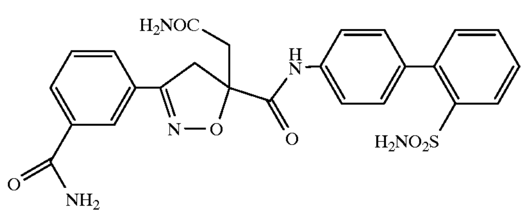 | |

TABLE 6

I-6

| EX# | P1 | R | X | MP(° C.) | MS(M + H)+ |
|---|---|---|---|---|---|
| 219 | 3-amidino-4-fluorophenyl | —CH₃ | CH | 140 | 496.3 |
| 220 | 3-amidino-4-methoxyphenyl | —CH₃ | CH | 240 | 508.3 (69%) |
| 221 | 3-amidino-4-hydroxyphenyl | —CH₃ | CH | 235 | 494.3 |
| 222 | 3-amidino-4-fluorophenyl | CH₂OCH₃ | N | 81 | 528.4 |
| 223 | 3-amidino-4-fluorophenyl | CH₂OCH₃ | CH | 175 | 526.4 |
| 224 | 3-amidino-4-fluorophenyl | CH₂OCH₃ | CH | 215 | 526.3 |
| 225 | 3-amidino-4-methoxyphenyl | —CH₃ | CH | 245 | 508.4 |

TABLE 6-continued

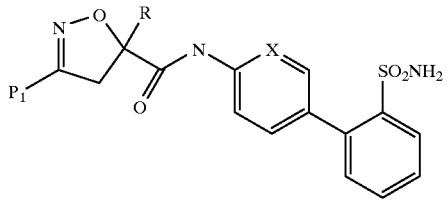

I-6

| EX# | P1 | R | X | MP(° C.) | MS(M + H)+ |
|---|---|---|---|---|---|
| 226 | ![P1 structure with NH, H2N, OH] | —CH₃ | CH | 238 | 494.2 |
| 227 | ![P1 structure with H2N] | —CH₃ | CH | 207 | 451.4 |

Tables 7–15 identify additional representative compounds of this invention which can be prepared by the methods described above.

The divalent radicals V in the compounds of Tables 7–11 have the following structures 1, 4-phenylene 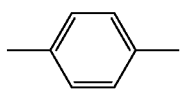

pyridin-2, 5-diyl 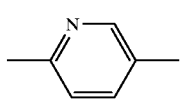

pyrimidin-2, 5-diyl 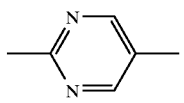

2-fluoro-1, 4-phenylene 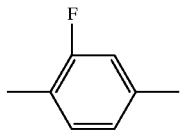

2-chloro-1, 4-phenylene 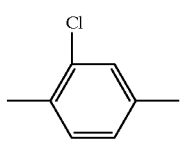

-continued 2-methyl-1, 4-phenylene 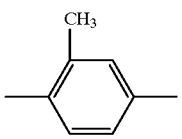

2, 5-thiophene

The pyridin-2,5-diyl and pyrimidin-2,5-diyl radicals are bonded to the $(Z)_u$-D moiety at the 5 position. The 2-substituted-1,4-phenylene radicals are bonded to the $(Z)_u$-D moiety at the 4 position.

The compounds of Tables 7-11 have the structures indicated by the formula "a" under each table heading. The corresponding compounds having the structures of formula "b" under each table heading can be obtained by substituting the appropriate starting material, as illustrated in Examples 10 and 11.

TABLE 7

*a*

*b*

| Part | Cpd | R | (CH$_2$)$_n$R$^2$ | V | (Z)$_u$—D |
|---|---|---|---|---|---|
| A1 | 1 | CH$_2$OCH$_3$ | CH$_2$OMe | 1-4-phenylene | 2-aminosulfonylphenyl |
|  | 2 | CH$_2$OCH$_3$ | CH$_2$OEt | 1-4-phenylene | 2-aminosulfonylphenyl |
|  | 3 | CH$_2$OCH$_3$ | CH$_2$O-n-Pr | 1-4-phenylene | 2-aminosulfonylphenyl |
|  | 4 | CH$_2$OCH$_3$ | CH$_2$O-i-Pr | 1-4-phenylene | 2-aminosulfonylphenyl |
|  | 5 | CH$_2$OCH$_3$ | CH$_2$O-n-Bu | 1-4-phenylene | 2-aminosulfonylphenyl |
|  | 6 | CH$_2$OCH$_3$ | CH$_2$O-i-Bu | 1-4-phenylene | 2-aminosulfonylphenyl |
|  | 7 | CH$_2$OCH$_3$ | CH$_2$Ph | 1-4-phenylene | 2-aminosulfonylphenyl |
|  | 8 | CH$_2$OCH$_3$ | CH$_2$-pyrazol-1-yl | 1-4-phenylene | 2-aminosulfonylphenyl |
|  | 9 | CH$_2$OCH$_3$ | CH$_2$-imidazol-1-yl | 1-4-phenylene | 2-aminosulfonylphenyl |
|  | 10 | CH$_2$OCH$_3$ | CH$_2$-tetrazol-1-yl | 1-4-phenylene | 2-aminosulfonylphenyl |
|  | 11 | CH$_2$OCH$_3$ | CH$_2$-tetrazol-2-yl | 1-4-phenylene | 2-aminosulfonylphenyl |
|  | 12 | CH$_2$OCH$_3$ | CH$_2$-triazol-1-yl | 1-4-phenylene | 2-aminosulfonylphenyl |
|  | 13 | CH$_2$OCH$_3$ | CH$_2$SEt | 1-4-phenylene | 2-aminosulfonylphenyl |
|  | 14 | CH$_2$OCH$_3$ | CH$_2$SO$_2$Et | 1-4-phenylene | 2-aminosulfonylphenyl |
|  | 15 | CH$_2$OCH$_3$ | CF$_3$ | 1-4-phenylene | 2-aminosulfonylphenyl |
|  | 16 | CH$_2$OCH$_3$ | CH$_3$ | 1-4-phenylene | 2-aminosulfonylphenyl |
|  | 17 | CH$_2$OCH$_3$ | H | 1-4-phenylene | 2-aminosulfonylphenyl |
| A2 | 1 | CH$_2$OCH$_3$ | CH$_2$OMe | pyridin-2,5-diyl | 2-aminosulfonylphenyl |
|  | 2 | CH$_2$OCH$_3$ | CH$_2$OEt | pyridin-2,5-diyl | 2-aminosulfonylphenyl |
|  | 3 | CH$_2$OCH$_3$ | CH$_2$O-n-Pr | pyridin-2,5-diyl | 2-aminosulfonylphenyl |
|  | 4 | CH$_2$OCH$_3$ | CH$_2$O-i-Pr | pyridin-2,5-diyl | 2-aminosulfonylphenyl |
|  | 5 | CH$_2$OCH$_3$ | CH$_2$O-n-Bu | pyridin-2,5-diyl | 2-aminosulfonylphenyl |
|  | 6 | CH$_2$OCH$_3$ | CH$_2$O-i-Bu | pyridin-2,5-diyl | 2-aminosulfonylphenyl |
|  | 7 | CH$_2$OCH$_3$ | CH$_2$Ph | pyridin-2,5-diyl | 2-aminosulfonylphenyl |
|  | 8 | CH$_2$OCH$_3$ | CH$_2$-pyrazol-1-yl | pyridin-2,5-diyl | 2-aminosulfonylphenyl |
|  | 9 | CH$_2$OCH$_3$ | CH$_2$-imidazol-1-yl | pyridin-2,5-diyl | 2-aminosulfonylphenyl |
|  | 10 | CH$_2$OCH$_3$ | CH$_2$-tetrazol-1-yl | pyridin-2,5-diyl | 2-aminosulfonylphenyl |
|  | 11 | CH$_2$OCH$_3$ | CH$_2$-tetrazol-2-yl | pyridin-2,5-diyl | 2-aminosulfonylphenyl |
|  | 12 | CH$_2$OCH$_3$ | CH$_2$-triazol-1-yl | pyridin-2,5-diyl | 2-aminosulfonylphenyl |
|  | 13 | CH$_2$OCH$_3$ | CH$_2$SEt | pyridin-2,5-diyl | 2-aminosulfonylphenyl |
|  | 14 | CH$_2$OCH$_3$ | CH$_2$SO$_2$Et | pyridin-2,5-diyl | 2-aminosulfonylphenyl |
|  | 15 | CH$_2$OCH$_3$ | CF$_3$ | pyridin-2,5-diyl | 2-aminosulfonylphenyl |
|  | 16 | CH$_2$OCH$_3$ | CH$_3$ | pyridin-2,5-diyl | 2-aminosulfonylphenyl |
|  | 17 | CH$_2$OCH$_3$ | H | pyridin-2,5-diyl | 2-aminosulfonylphenyl |
| A3 | 1 | CH$_2$OCH$_3$ | CH$_2$OMe | pyrimidin-2,5-diyl | 2-aminosulfonylphenyl |
|  | 2 | CH$_2$OCH$_3$ | CH$_2$OEt | pyrimidin-2,5-diyl | 2-aminosulfonylphenyl |
|  | 3 | CH$_2$OCH$_3$ | CH$_2$O-n-Pr | pyrimidin-2,5-diyl | 2-aminosulfonylphenyl |
|  | 4 | CH$_2$OCH$_3$ | CH$_2$O-i-Pr | pyrimidin-2,5-diyl | 2-aminosulfonylphenyl |
|  | 5 | CH$_2$OCH$_3$ | CH$_2$O-n-Bu | pyrimidin-2,5-diyl | 2-aminosulfonylphenyl |
|  | 6 | CH$_2$OCH$_3$ | CH$_2$O-i-Bu | pyrimidin-2,5-diyl | 2-aminosulfonylphenyl |
|  | 7 | CH$_2$OCH$_3$ | CH$_2$Ph | pyrimidin-2,5-diyl | 2-aminosulfonylphenyl |
|  | 8 | CH$_2$OCH$_3$ | CH$_2$-pyrazol-1-yl | pyrimidin-2,5-diyl | 2-aminosulfonylphenyl |
|  | 9 | CH$_2$OCH$_3$ | CH$_2$-imidazol-1-yl | pyrimidin-2,5-diyl | 2-aminosulfonylphenyl |
|  | 10 | CH$_2$OCH$_3$ | CH$_2$-tetrazol-1-yl | pyrimidin-2,5-diyl | 2-aminosulfonylphenyl |
|  | 11 | CH$_2$OCH$_3$ | CH$_2$-tetrazol-2-yl | pyrimidin-2,5-diyl | 2-aminosulfonylphenyl |
|  | 12 | CH$_2$OCH$_3$ | CH$_2$-triazol-1-yl | pyrimidin-2,5-diyl | 2-aminosulfonylphenyl |
|  | 13 | CH$_2$OCH$_3$ | CH$_2$SEt | pyrimidin-2,5-diyl | 2-aminosulfonylphenyl |
|  | 14 | CH$_2$OCH$_3$ | CH$_2$SO$_2$Et | pyrimidin-2,5-diyl | 2-aminosulfonylphenyl |
|  | 15 | CH$_2$OCH$_3$ | CF$_3$ | pyrimidin-2,5-diyl | 2-aminosulfonylphenyl |
|  | 16 | CH$_2$OCH$_3$ | CH$_3$ | pyrimidin-2,5-diyl | 2-aminosulfonylphenyl |
|  | 17 | CH$_2$OCH$_3$ | H | pyrimidin-2,5-diyl | 2-aminosulfonylphenyl |

TABLE 7-continued a: 3-[3-(amidino)phenyl]-isoxazoline-5-carboxamide structure with R, (CH₂)ₙR² at 5-position, C(O)NH-V-(Z)ᵤ-D b: regioisomer with R and C(O)NH-V-(Z)ᵤ-D at 4-position and (CH₂)ₙR² at 5-position

| Part | Cpd | R | (CH₂)₂R² | V | (Z)ᵤ—D |
|---|---|---|---|---|---|
| A4 | 1 | CH₂OCH₃ | CH₂OMe | 2-fluoro-1,4-phenylene | 2-aminosulfonylphenyl |
|  | 2 | CH₂OCH₃ | CH₂OEt | 2-fluoro-1,4-phenylene | 2-aminosulfonylphenyl |
|  | 3 | CH₂OCH₃ | CH₂O-n-Pr | 2-fluoro-1,4-phenylene | 2-aminosulfonylphenyl |
|  | 4 | CH₂OCH₃ | CH₂O-i-Pr | 2-fluoro-1,4-phenylene | 2-aminosulfonylphenyl |
|  | 5 | CH₂OCH₃ | CH₂O-n-Bu | 2-fluoro-1,4-phenylene | 2-aminosulfonylphenyl |
|  | 6 | CH₂OCH₃ | CH₂O-i-Bu | 2-fluoro-1,4-phenylene | 2-aminosulfonylphenyl |
|  | 7 | CH₂OCH₃ | CH₂Ph | 2-fluoro-1,4-phenylene | 2-aminosulfonylphenyl |
|  | 8 | CH₂OCH₃ | CH₂-pyrazol-1-yl | 2-fluoro-1,4-phenylene | 2-aminosulfonylphenyl |
|  | 9 | CH₂OCH₃ | CH₂-imidazol-1-yl | 2-fluoro-1,4-phenylene | 2-aminosulfonylphenyl |
|  | 10 | CH₂OCH₃ | CH₂-tetrazol-1-yl | 2-fluoro-1,4-phenylene | 2-aminosulfonylphenyl |
|  | 11 | CH₂OCH₃ | CH₂-tetrazol-2-yl | 2-fluoro-1,4-phenylene | 2-aminosulfonylphenyl |
|  | 12 | CH₂OCH₃ | CH₂-triazol-1-yl | 2-fluoro-1,4-phenylene | 2-aminosulfonylphenyl |
|  | 13 | CH₂OCH₃ | CH₂SEt | 2-fluoro-1,4-phenylene | 2-aminosulfonylphenyl |
|  | 14 | CH₂OCH₃ | CH₂SO₂Et | 2-fluoro-1,4-phenylene | 2-aminosulfonylphenyl |
|  | 15 | CH₂OCH₃ | CF₃ | 2-fluoro-1,4-phenylene | 2-aminosulfonylphenyl |
|  | 16 | CH₂OCH₃ | CH₃ | 2-fluoro-1,4-phenylene | 2-aminosulfonylphenyl |
|  | 17 | CH₂OCH₃ | H | 2-fluoro-1,4-phenylene | 2-aminosulfonylphenyl |
| A5 | 1 | CH₂OCH₃ | CH₂OMe | 2-chloro-1,4-phenylene | 2-aminosulfonylphenyl |
|  | 2 | CH₂OCH₃ | CH₂OEt | 2-chloro-1,4-phenylene | 2-aminosulfonylphenyl |
|  | 3 | CH₂OCH₃ | CH₂O-n-Pr | 2-chloro-1,4-phenylene | 2-aminosulfonylphenyl |
|  | 4 | CH₂OCH₃ | CH₂O-i-Pr | 2-chloro-1,4-phenylene | 2-aminosulfonylphenyl |
|  | 5 | CH₂OCH₃ | CH₂O-n-Bu | 2-chloro-1,4-phenylene | 2-aminosulfonylphenyl |
|  | 6 | CH₂OCH₃ | CH₂O-i-Bu | 2-chloro-1,4-phenylene | 2-aminosulfonylphenyl |
|  | 7 | CH₂OCH₃ | CH₂Ph | 2-chloro-1,4-phenylene | 2-aminosulfonylphenyl |
|  | 8 | CH₂OCH₃ | CH₂-pyrazol-1-yl | 2-chloro-1,4-phenylene | 2-aminosulfonylphenyl |
|  | 9 | CH₂OCH₃ | CH₂-imidazol-1-yl | 2-chloro-1,4-phenylene | 2-aminosulfonylphenyl |
|  | 10 | CH₂OCH₃ | CH₂-tetrazol-1-yl | 2-chloro-1,4-phenylene | 2-aminosulfonylphenyl |
|  | 11 | CH₂OCH₃ | CH₂-tetrazol-2-yl | 2-chloro-1,4-phenylene | 2-aminosulfonylphenyl |
|  | 12 | CH₂OCH₃ | CH₂-triazol-1-yl | 2-chloro-1,4-phenylene | 2-aminosulfonylphenyl |
|  | 13 | CH₂OCH₃ | CH₂SEt | 2-chloro-1,4-phenylene | 2-aminosulfonylphenyl |
|  | 14 | CH₂OCH₃ | CH₂SO₂Et | 2-chloro-1,4-phenylene | 2-aminosulfonylphenyl |
|  | 15 | CH₂OCH₃ | CF₃ | 2-chloro-1,4-phenylene | 2-aminosulfonylphenyl |
|  | 16 | CH₂OCH₃ | CH₃ | 2-chloro-1,4-phenylene | 2-aminosulfonylphenyl |
|  | 17 | CH₂OCH₃ | H | 2-chloro-1,4-phenylene | 2-aminosulfonylphenyl |
| B1 | 1 | CH₃ | CH₂OMe | 1,4-phenylene | 2-aminosulfonylphenyl |
|  | 2 | CH₃ | CH₂OEt | 1,4-phenylene | 2-aminosulfonylphenyl |
|  | 3 | CH₃ | CH₂O-n-Pr | 1,4-phenylene | 2-aminosulfonylphenyl |
|  | 4 | CH₃ | CH₂O-i-Pr | 1,4-phenylene | 2-aminosulfonylphenyl |
|  | 5 | CH₃ | CH₂O-n-Bu | 1,4-phenylene | 2-aminosulfonylphenyl |
|  | 6 | CH₃ | CH₂O-i-Bu | 1,4-phenylene | 2-aminosulfonylphenyl |
|  | 7 | CH₃ | CH₂Ph | 1,4-phenylene | 2-aminosulfonylphenyl |
|  | 8 | CH₃ | CH₂-pyrazol-1-yl | 1,4-phenylene | 2-aminosulfonylphenyl |
|  | 9 | CH₃ | CH₂-pyrazol-1-yl | 1,4-phenylene | 2-aminosulfonylphenyl |
|  | 10 | CH₃ | CH₂-pyrazol-1-yl | 1,4-phenylene | 2-aminosulfonylphenyl |
|  | 11 | CH₃ | CH₂-pyrazol-1-yl | 1,4-phenylene | 2-aminosulfonylphenyl |
|  | 12 | CH₃ | CH₂-pyrazol-1-yl | 1,4-phenylene | 2-aminosulfonylphenyl |
|  | 13 | CH₃ | CH₂SEt | 1,4-phenylene | 2-aminosulfonylphenyl |
|  | 14 | CH₃ | CH₂SO₂Et | 1,4-phenylene | 2-aminosulfonylphenyl |
|  | 15 | CH₃ | CF₃ | 1,4-phenylene | 2-aminosulfonylphenyl |
|  | 16 | CH₃ | CH₃ | 1,4-phenylene | 2-aminosulfonylphenyl |
|  | 17 | CH₃ | H | 1,4-phenylene | 2-aminosulfonylphenyl |

TABLE 7-continued a b

| Part | Cpd | R | (CH$_2$)$_2$R$^2$ | V | (Z)$_u$—D |
|---|---|---|---|---|---|
| B2 | 1 | CH$_3$ | CH$_2$OMe | pyridin-2,5-diyl | 2-aminosulfonylphenyl |
|  | 2 | CH$_3$ | CH$_2$OEt | pyridin-2,5-diyl | 2-aminosulfonylphenyl |
|  | 3 | CH$_3$ | CH$_2$O-n-Pr | pyridin-2,5-diyl | 2-aminosulfonylphenyl |
|  | 4 | CH$_3$ | CH$_2$O-i-Pr | pyridin-2,5-diyl | 2-aminosulfonylphenyl |
|  | 5 | CH$_3$ | CH$_2$O-n-Bu | pyridin-2,5-diyl | 2-aminosulfonylphenyl |
|  | 6 | CH$_3$ | CH$_2$O-i-Bu | pyridin-2,5-diyl | 2-aminosulfonylphenyl |
|  | 7 | CH$_3$ | CH$_2$Ph | pyridin-2,5-diyl | 2-aminosulfonylphenyl |
|  | 8 | CH$_3$ | CH$_2$-pyrazol-1-yl | pyridin-2,5-diyl | 2-aminosulfonylphenyl |
|  | 9 | CH$_3$ | CH$_2$-imidazol-1-yl | pyridin-2,5-diyl | 2-aminosulfonylphenyl |
|  | 10 | CH$_3$ | CH$_2$-tetrazol-1-yl | pyridin-2,5-diyl | 2-aminosulfonylphenyl |
|  | 11 | CH$_3$ | CH$_2$-tetrazol-2-yl | pyridin-2,5-diyl | 2-aminosulfonylphenyl |
|  | 12 | CH$_3$ | CH$_2$-triazol-1-yl | pyridin-2,5-diyl | 2-aminosulfonylphenyl |
|  | 13 | CH$_3$ | CH$_2$SEt | pyridin-2,5-diyl | 2-aminosulfonylphenyl |
|  | 14 | CH$_3$ | CH$_2$SO$_2$Et | pyridin-2,5-diyl | 2-aminosulfonylphenyl |
|  | 15 | CH$_3$ | CF$_3$ | pyridin-2,5-diyl | 2-aminosulfonylphenyl |
|  | 16 | CH$_3$ | CH$_3$ | pyridin-2,5-diyl | 2-aminosulfonylphenyl |
|  | 17 | CH$_3$ | H | pyridin-2,5-diyl | 2-aminosulfonylphenyl |
| B3 | 1 | CH$_3$ | CH$_2$OMe | pyrimidin-2,5-diyl | 2-aminosulfonylphenyl |
|  | 2 | CH$_3$ | CH$_2$OEt | pyrimidin-2,5-diyl | 2-aminosulfonylphenyl |
|  | 3 | CH$_3$ | CH$_2$O-n-Pr | pyrimidin-2,5-diyl | 2-aminosulfonylphenyl |
|  | 4 | CH$_3$ | CH$_2$O-i-Pr | pyrimidin-2,5-diyl | 2-aminosulfonylphenyl |
|  | 5 | CH$_3$ | CH$_2$O-n-Bu | pyrimidin-2,5-diyl | 2-aminosulfonylphenyl |
|  | 6 | CH$_3$ | CH$_2$O-i-Bu | pyrimidin-2,5-diyl | 2-aminosulfonylphenyl |
|  | 7 | CH$_3$ | CH$_2$Ph | pyrimidin-2,5-diyl | 2-aminosulfonylphenyl |
|  | 8 | CH$_3$ | CH$_2$-pyrazol-1-yl | pyrimidin-2,5-diyl | 2-aminosulfonylphenyl |
|  | 9 | CH$_3$ | CH$_2$-imidazol-1-yl | pyrimidin-2,5-diyl | 2-aminosulfonylphenyl |
|  | 10 | CH$_3$ | CH$_2$-tetrazol-1-yl | pyrimidin-2,5-diyl | 2-aminosulfonylphenyl |
|  | 11 | CH$_3$ | CH$_2$-tetrazol-2-yl | pyrimidin-2,5-diyl | 2-aminosulfonylphenyl |
|  | 12 | CH$_3$ | CH$_2$-triazol-1-yl | pyrimidin-2,5-diyl | 2-aminosulfonylphenyl |
|  | 13 | CH$_3$ | CH$_2$SEt | pyrimidin-2,5-diyl | 2-aminosulfonylphenyl |
|  | 14 | CH$_3$ | CH$_2$SO$_2$Et | pyrimidin-2,5-diyl | 2-aminosulfonylphenyl |
|  | 15 | CH$_3$ | CF$_3$ | pyrimidin-2,5-diyl | 2-aminosulfonylphenyl |
|  | 16 | CH$_3$ | CH$_3$ | pyrimidin-2,5-diyl | 2-aminosulfonylphenyl |
|  | 17 | CH$_3$ | H | pyrimidin-2,5-diyl | 2-aminosulfonylphenyl |
| B4 | 1 | CH$_3$ | CH$_2$OMe | 2-fluoro-1,4-phenylene | 2-aminosulfonylphenyl |
|  | 2 | CH$_3$ | CH$_2$OEt | 2-fluoro-1,4-phenylene | 2-aminosulfonylphenyl |
|  | 3 | CH$_3$ | CH$_2$O-n-Pr | 2-fluoro-1,4-phenylene | 2-aminosulfonylphenyl |
|  | 4 | CH$_3$ | CH$_2$O-i-Pr | 2-fluoro-1,4-phenylene | 2-aminosulfonylphenyl |
|  | 5 | CH$_3$ | CH$_2$O-n-Bu | 2-fluoro-1,4-phenylene | 2-aminosulfonylphenyl |
|  | 6 | CH$_3$ | CH$_2$O-i-Bu | 2-fluoro-1,4-phenylene | 2-aminosulfonylphenyl |
|  | 7 | CH$_3$ | CH$_2$Ph | 2-fluoro-1,4-phenylene | 2-aminosulfonylphenyl |
|  | 8 | CH$_3$ | CH$_2$-pyrazol-1-yl | 2-fluoro-1,4-phenylene | 2-aminosulfonylphenyl |
|  | 9 | CH$_3$ | CH$_2$-imidazol-1-yl | 2-fluoro-1,4-phenylene | 2-aminosulfonylphenyl |
|  | 10 | CH$_3$ | CH$_2$-tetrazol-1-yl | 2-fluoro-1,4-phenylene | 2-aminosulfonylphenyl |
|  | 11 | CH$_3$ | CH$_2$-tetrazol-2-yl | 2-fluoro-1,4-phenylene | 2-aminosulfonylphenyl |
|  | 12 | CH$_3$ | CH$_2$-triazol-1-yl | 2-fluoro-1,4-phenylene | 2-aminosulfonylphenyl |
|  | 13 | CH$_3$ | CH$_2$SEt | 2-fluoro-1,4-phenylene | 2-aminosulfonylphenyl |
|  | 14 | CH$_3$ | CH$_2$SO$_2$Et | 2-fluoro-1,4-phenylene | 2-aminosulfonylphenyl |
|  | 15 | CH$_3$ | CF$_3$ | 2-fluoro-1,4-phenylene | 2-aminosulfonylphenyl |
|  | 16 | CH$_3$ | CH$_3$ | 2-fluoro-1,4-phenylene | 2-aminosulfonylphenyl |
|  | 17 | CH$_3$ | H | 2-fluoro-1,4-phenylene | 2-aminosulfonylphenyl |

TABLE 7-continued structure a: 3-(3-amidinophenyl)-isoxazoline with R and (CH₂)ₙR² substituents, carboxamide linked to N—V—(Z)ᵤ—D structure b: regioisomer with R and (CH₂)ₙR² on the other isoxazoline position

| Part | Cpd | R | (CH₂)₂R² | V | (Z)ᵤ—D |
|---|---|---|---|---|---|
| B5 | 1 | CH₃ | CH₂OMe | 2-chloro-1,4-phenylene | 2-aminosulfonylphenyl |
|  | 2 | CH₃ | CH₂OEt | 2-chloro-1,4-phenylene | 2-aminosulfonylphenyl |
|  | 3 | CH₃ | CH₂O-n-Pr | 2-chloro-1,4-phenylene | 2-aminosulfonylphenyl |
|  | 4 | CH₃ | CH₂O-i-Pr | 2-chloro-1,4-phenylene | 2-aminosulfonylphenyl |
|  | 5 | CH₃ | CH₂O-n-Bu | 2-chloro-1,4-phenylene | 2-aminosulfonylphenyl |
|  | 6 | CH₃ | CH₂O-i-Bu | 2-chloro-1,4-phenylene | 2-aminosulfonylphenyl |
|  | 7 | CH₃ | CH₂Ph | 2-chloro-1,4-phenylene | 2-aminosulfonylphenyl |
|  | 8 | CH₃ | CH₂-pyrazol-1-yl | 2-chloro-1,4-phenylene | 2-aminosulfonylphenyl |
|  | 9 | CH₃ | CH₂-imidazol-1-yl | 2-chloro-1,4-phenylene | 2-aminosulfonylphenyl |
|  | 10 | CH₃ | CH₂-tetrazol-1-yl | 2-chloro-1,4-phenylene | 2-aminosulfonylphenyl |
|  | 11 | CH₃ | CH₂-tetrazol-2-yl | 2-chloro-1,4-phenylene | 2-aminosulfonylphenyl |
|  | 12 | CH₃ | CH₂-triazol-1-yl | 2-chloro-1,4-phenylene | 2-aminosulfonylphenyl |
|  | 13 | CH₃ | CH₂SEt | 2-chloro-1,4-phenylene | 2-aminosulfonylphenyl |
|  | 14 | CH₃ | CH₂SO₂Et | 2-chloro-1,4-phenylene | 2-aminosulfonylphenyl |
|  | 15 | CH₃ | CF₃ | 2-chloro-1,4-phenylene | 2-aminosulfonylphenyl |
|  | 16 | CH₃ | CH₃ | 2-chloro-1,4-phenylene | 2-aminosulfonylphenyl |
|  | 17 | CH₃ | H | 2-chloro-1,4-phenylene | 2-aminosulfonylphenyl |
| C1 | 1 | H | CH₂OMe | 1,4-phenylene | 2-aminosulfonylphenyl |
|  | 2 | H | CH₂OEt | 1,4-phenylene | 2-aminosulfonylphenyl |
|  | 3 | H | CH₂O-n-Pr | 1,4-phenylene | 2-aminosulfonylphenyl |
|  | 4 | H | CH₂O-i-Pr | 1,4-phenylene | 2-aminosulfonylphenyl |
|  | 5 | H | CH₂O-n-Bu | 1,4-phenylene | 2-aminosulfonylphenyl |
|  | 6 | H | CH₂O-i-Bu | 1,4-phenylene | 2-aminosulfonylphenyl |
|  | 7 | H | CH₂Ph | 1,4-phenylene | 2-aminosulfonylphenyl |
|  | 8 | H | CH₂-pyrazol-1-yl | 1,4-phenylene | 2-aminosulfonylphenyl |
|  | 9 | H | CH₂-imidazol-1-yl | 1,4-phenylene | 2-aminosulfonylphenyl |
|  | 10 | H | CH₂tetrazol-1-yl | 1,4-phenylene | 2-aminosulfonylphenyl |
|  | 11 | H | CH₂-tetrazol-2-yl | 1,4-phenylene | 2-aminosulfonylphenyl |
|  | 12 | H | CH₂-triazol-1-yl | 1,4-phenylene | 2-aminosulfonylphenyl |
|  | 13 | H | CH₂SEt | 1,4-phenylene | 2-aminosulfonylphenyl |
|  | 14 | H | CH₂SO₂Et | 1,4-phenylene | 2-aminosulfonylphenyl |
|  | 15 | H | CF₃ | 1,4-phenylene | 2-aminosulfonylphenyl |
|  | 16 | H | CH₃ | 1,4-phenylene | 2-aminosulfonylphenyl |
|  | 17 | H | H | 1,4-phenylene | 2-aminosulfonylphenyl |
| C2 | 1 | H | CH₂OMe | pyridin-2,5-diyl | 2-aminosulfonylphenyl |
|  | 2 | H | CH₂OEt | pyridin-2,5-diyl | 2-aminosulfonylphenyl |
|  | 3 | H | CH₂O-n-Pr | pyridin-2,5-diyl | 2-aminosulfonylphenyl |
|  | 4 | H | CH₂O-i-Pr | pyridin-2,5-diyl | 2-aminosulfonylphenyl |
|  | 5 | H | CH₂O-n-Bu | pyridin-2,5-diyl | 2-aminosulfonylphenyl |
|  | 6 | H | CH₂O-i-Bu | pyridin-2,5-diyl | 2-aminosulfonylphenyl |
|  | 7 | H | CH₂Ph | pyridin-2,5-diyl | 2-aminosulfonylphenyl |
|  | 8 | H | CH₂-pyrazol-1-yl | pyridin-2,5-diyl | 2-aminosulfonylphenyl |
|  | 9 | H | CH₂-imidazol-1-yl | pyridin-2,5-diyl | 2-aminosulfonylphenyl |
|  | 10 | H | CH₂-tetrazol-1-yl | pyridin-2,5-diyl | 2-aminosulfonylphenyl |
|  | 11 | H | CH₂-tetrazol-2-yl | pyridin-2,5-diyl | 2-aminosulfonylphenyl |
|  | 12 | H | CH₂-triazol-1-yl | pyridin-2,5-diyl | 2-aminosulfonylphenyl |
|  | 13 | H | CH₂SEt | pyridin-2,5-diyl | 2-aminosulfonylphenyl |
|  | 14 | H | CH₂SO₂Et | pyridin-2,5-diyl | 2-aminosulfonylphenyl |
|  | 15 | H | CF₃ | pyridin-2,5-diyl | 2-aminosulfonylphenyl |
|  | 16 | H | CH₃ | pyridin-2,5-diyl | 2-aminosulfonylphenyl |
|  | 17 | H | H | pyridin-2,5-diyl | 2-aminosulfonylphenyl |

TABLE 7-continued a: 3-[3-amidinophenyl]-4-R-5-(CH₂)ₙR²-4,5-dihydroisoxazole-5-carboxamide structure with N—V—(Z)ᵤ—D b: 3-[3-amidinophenyl]-4-R-5-(CH₂)ₙR²-4,5-dihydroisoxazole-4-carboxamide structure with N—V—(Z)ᵤ—D

| Part | Cpd | R | (CH$_2$)$_2$R$^2$ | V | (Z)$_u$—D |
|---|---|---|---|---|---|
| C3 | 1 | H | CH$_2$OMe | pyrimidin-2,5-diyl | 2-aminosulfonylphenyl |
|  | 2 | H | CH$_2$OEt | pyrimidin-2,5-diyl | 2-aminosulfonylphenyl |
|  | 3 | H | CH$_2$O-n-Pr | pyrimidin-2,5-diyl | 2-aminosulfonylphenyl |
|  | 4 | H | CH$_2$O-i-Pr | pyrimidin-2,5-diyl | 2-aminosulfonylphenyl |
|  | 5 | H | CH$_2$O-n-Bu | pyrimidin-2,5-diyl | 2-aminosulfonylphenyl |
|  | 6 | H | CH$_2$O-i-Bu | pyrimidin-2,5-diyl | 2-aminosulfonylphenyl |
|  | 7 | H | CH$_2$Ph | pyrimidin-2,5-diyl | 2-aminosulfonylphenyl |
|  | 8 | H | CH$_2$-pyrazol-1-yl | pyrimidin-2,5-diyl | 2-aminosulfonylphenyl |
|  | 9 | H | CH$_2$-imidazol-1-yl | pyrimidin-2,5-diyl | 2-aminosulfonylphenyl |
|  | 10 | H | CH$_2$-tetrazol-1-yl | pyrimidin-2,5-diyl | 2-aminosulfonylphenyl |
|  | 11 | H | CH$_2$-tetrazol-2-yl | pyrimidin-2,5-diyl | 2-aminosulfonylphenyl |
|  | 12 | H | CH$_2$-triazol-1-yl | pyrimidin-2,5-diyl | 2-aminosulfonylphenyl |
|  | 13 | H | CH$_2$SEt | pyrimidin-2,5-diyl | 2-aminosulfonylphenyl |
|  | 14 | H | CH$_2$SO$_2$Et | pyrimidin-2,5-diyl | 2-aminosulfonylphenyl |
|  | 15 | H | CF$_3$ | pyrimidin-2,5-diyl | 2-aminosulfonylphenyl |
|  | 16 | H | CH$_3$ | pyrimidin-2,5-diyl | 2-aminosulfonylphenyl |
|  | 17 | H | H | pyrimidin-2,5-diyl | 2-aminosulfonylphenyl |
| C4 | 1 | H | CH$_2$OMe | 2-fluoro-1,4-phenylene | 2-aminosulfonylphenyl |
|  | 2 | H | CH$_2$OEt | 2-fluoro-1,4-phenylene | 2-aminosulfonylphenyl |
|  | 3 | H | CH$_2$O-n-Pr | 2-fluoro-1,4-phenylene | 2-aminosulfonylphenyl |
|  | 4 | H | CH$_2$O-i-Pr | 2-fluoro-1,4-phenylene | 2-aminosulfonylphenyl |
|  | 5 | H | CH$_2$O-n-Bu | 2-fluoro-1,4-phenylene | 2-aminosulfonylphenyl |
|  | 6 | H | CH$_2$O-i-Bu | 2-fluoro-1,4-phenylene | 2-aminosulfonylphenyl |
|  | 7 | H | CH$_2$Ph | 2-fluoro-1,4-phenylene | 2-aminosulfonylphenyl |
|  | 8 | H | CH$_2$-pyrazol-1-yl | 2-fluoro-1,4-phenylene | 2-aminosulfonylphenyl |
|  | 9 | H | CH$_2$-imidazol-1-yl | 2-fluoro-1,4-phenylene | 2-aminosulfonylphenyl |
|  | 10 | H | CH$_2$-tetrazol-1-yl | 2-fluoro-1,4-phenylene | 2-aminosulfonylphenyl |
|  | 11 | H | CH$_2$-tetrazol-2-yl | 2-fluoro-1,4-phenylene | 2-aminosulfonylphenyl |
|  | 12 | H | CH$_2$-triazol-1-yl | 2-fluoro-1,4-phenylene | 2-aminosulfonylphenyl |
|  | 13 | H | CH$_2$SEt | 2-fluoro-1,4-phenylene | 2-aminosulfonylphenyl |
|  | 14 | H | CH$_2$SO$_2$Et | 2-fluoro-1,4-phenylene | 2-aminosulfonylphenyl |
|  | 15 | H | CF$_3$ | 2-fluoro-1,4-phenylene | 2-aminosulfonylphenyl |
|  | 16 | H | CH$_3$ | 2-fluoro-1,4-phenylene | 2-aminosulfonylphenyl |
|  | 17 | H | H | 2-fluoro-1,4-phenylene | 2-aminosulfonylphenyl |
| C5 | 1 | H | CH$_2$OMe | 2-chloro-1,4-phenylene | 2-aminosulfonylphenyl |
|  | 2 | H | CH$_2$OEt | 2-chloro-1,4-phenylene | 2-aminosulfonylphenyl |
|  | 3 | H | CH$_2$O-n-Pr | 2-chloro-1,4-phenylene | 2-aminosulfonylphenyl |
|  | 4 | H | CH$_2$O-i-Pr | 2-chloro-1,4-phenylene | 2-aminosulfonylphenyl |
|  | 5 | H | CH$_2$O-n-Bu | 2-chloro-1,4-phenylene | 2-aminosulfonylphenyl |
|  | 6 | H | CH$_2$O-i-Bu | 2-chloro-1,4-phenylene | 2-aminosulfonylphenyl |
|  | 7 | H | CH$_2$Ph | 2-chloro-1,4-phenylene | 2-aminosulfonylphenyl |
|  | 8 | H | CH$_2$-pyrazol-1-yl | 2-chloro-1,4-phenylene | 2-aminosulfonylphenyl |
|  | 9 | H | CH$_2$-imidazol-1-yl | 2-chloro-1,4-phenylene | 2-aminosulfonylphenyl |
|  | 10 | H | CH$_2$-tetrazol-1-yl | 2-chloro-1,4-phenylene | 2-aminosulfonylphenyl |
|  | 11 | H | CH$_2$-tetrazol-2-yl | 2-chloro-1,4-phenylene | 2-aminosulfonylphenyl |
|  | 12 | H | CH$_2$-triazol-1-yl | 2-chloro-1,4-phenylene | 2-aminosulfonylphenyl |
|  | 13 | H | CH$_2$SEt | 2-chloro-1,4-phenylene | 2-aminosulfonylphenyl |
|  | 14 | H | CH$_2$SO$_2$Et | 2-chloro-1,4-phenylene | 2-aminosulfonylphenyl |
|  | 15 | H | CF$_3$ | 2-chloro-1,4-phenylene | 2-aminosulfonylphenyl |
|  | 16 | H | CH$_3$ | 2-chloro-1,4-phenylene | 2-aminosulfonylphenyl |
|  | 17 | H | H | 2-chloro-1,4-phenylene | 2-aminosulfonylphenyl |

TABLE 7-continued

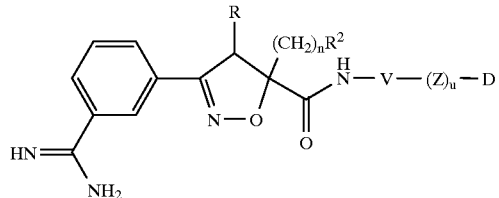

a

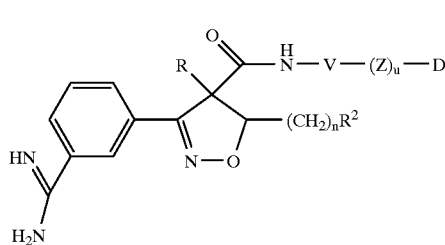

b

| Part | Cpd | R | (CH$_2$)$_n$R$^2$ | V | (Z)$_u$—D |
|---|---|---|---|---|---|
| C6 | 1 | H | CH$_2$OMe | 2-methyl-1,4-phenylene | 2-aminosulfonylphenyl |
| | 2 | H | CH$_2$OEt | 2-methyl-1,4-phenylene | 2-aminosulfonylphenyl |
| | 3 | H | CH$_2$O-n-Pr | 2-methyl-1,4-phenylene | 2-aminosulfonylphenyl |
| | 4 | H | CH$_2$O-i-Pr | 2-methyl-1,4-phenylene | 2-aminosulfonylphenyl |
| | 5 | H | CH$_2$O-n-Bu | 2-methyl-1,4-phenylene | 2-aminosulfonylphenyl |
| | 6 | H | CH$_2$O-i-Bu | 2-methyl-1,4-phenylene | 2-aminosulfonylphenyl |
| | 7 | H | CH$_2$Ph | 2-methyl-1,4-phenylene | 2-aminosulfonylphenyl |
| | 8 | H | CH$_2$-pyrazol-1-yl | 2-methyl-1,4-phenylene | 2-aminosulfonylphenyl |
| | 9 | H | CH$_2$-imidazol-1-yl | 2-methyl-1,4-phenylene | 2-aminosulfonylphenyl |
| | 10 | H | CH$_2$-tetrazol-1-yl | 2-methyl-1,4-phenylene | 2-aminosulfonylphenyl |
| | 11 | H | CH$_2$-tetrazol-2-yl | 2-methyl-1,4-phenylene | 2-aminosulfonylphenyl |
| | 12 | H | CH$_2$-triazol-1-yl | 2-methyl-1,4-phenylene | 2-aminosulfonylphenyl |
| | 13 | H | CH$_2$SEt | 2-methyl-1,4-phenylene | 2-aminosulfonylphenyl |
| | 14 | H | CH$_2$SO$_2$Et | 2-methyl-1,4-phenylene | 2-aminosulfonylphenyl |
| | 15 | H | CF$_3$ | 2-methyl-1,4-phenylene | 2-aminosulfonylphenyl |
| | 16 | H | CH$_3$ | 2-methyl-1,4-phenylene | 2-aminosulfonylphenyl |
| | 17 | H | H | 2-methyl-1,4-phenylene | 2-aminosulfonylphenyl |
| D1 | 1 | H | CH$_2$OMe | 1,4-phenylene | 2-trifluoromethylphenyl |
| | 2 | H | CH$_2$OEt | 1,4-phenylene | 2-trifluoromethylphenyl |
| | 3 | H | CH$_2$O-n-Pr | 1,4-phenylene | 2-trifluoromethylphenyl |
| | 4 | H | CH$_2$O-i-Pr | 1,4-phenylene | 2-trifluoromethylphenyl |
| | 5 | H | CH$_2$O-n-Bu | 1,4-phenylene | 2-trifluoromethylphenyl |
| | 6 | H | CH$_2$O-i-Bu | 1,4-phenylene | 2-trifluoromethylphenyl |
| | 7 | H | CH$_2$Ph | 1,4-phenylene | 2-trifluoromethylphenyl |
| | 8 | H | CH$_2$-pyrazol-1-yl | 1,4-phenylene | 2-trifluoromethylphenyl |
| | 9 | H | CH$_2$-imidazol-1-yl | 1,4-phenylene | 2-trifluoromethylphenyl |
| | 10 | H | CH$_2$-tetrazol-1-yl | 1,4-phenylene | 2-trifluoromethylphenyl |
| | 11 | H | CH$_2$-tetrazol-1-yl | 1,4-phenylene | 2-trifluoromethylphenyl |
| | 13 | H | CH$_2$SEt | pyridin-2,5-diyl | 2-trifluoromethylphenyl |
| | 14 | H | CH$_2$SO$_2$Et | pyridin-2,5-diyl | 2-trifluoromethylphenyl |
| | 15 | H | CF$_3$ | pyridin-2,5-diyl | 2-trifluoromethylphenyl |
| | 16 | H | CH$_3$ | pyridin-2,5-diyl | 2-trifluoromethylphenyl |
| | 17 | H | H | pyridin-2,5-diyl | 2-trifluoromethylphenyl |
| D3 | 1 | H | CH$_2$OMe | pyrimidin-2,5-diyl | 2-trifluoromethylphenyl |
| | 2 | H | CH$_2$OEt | pyrimidin-2,5-diyl | 2-trifluoromethylphenyl |
| | 3 | H | CH$_2$O-n-Pr | pyrimidin-2,5-diyl | 2-trifluoromethylphenyl |
| | 4 | H | CH$_2$O-i-Pr | pyrimidin-2,5-diyl | 2-trifluoromethylphenyl |
| | 5 | H | CH$_2$O-n-Bu | pyrimidin-2,5-diyl | 2-trifluoromethylphenyl |
| | 6 | H | CH$_2$O-i-Bu | pyrimidin-2,5-diyl | 2-trifluoromethylphenyl |
| | 7 | H | CH$_2$Ph | pyrimidin-2,5-diyl | 2-trifluoromethylphenyl |
| | 8 | H | CH$_2$-pyrazol-1-yl | pyrimidin-2,5-diyl | 2-trifluoromethylphenyl |
| | 9 | H | CH$_2$-imidazol-1-yl | pyrimidin-2,5-diyl | 2-trifluoromethylphenyl |
| | 10 | H | CH$_2$-tetrazol-1-yl | pyrimidin-2,5-diyl | 2-trifluoromethylphenyl |
| | 11 | H | CH$_2$-tetrazol-2-yl | pyrimidin-2,5-diyl | 2-trifluoromethylphenyl |
| | 12 | H | CH$_2$-triazol-1-yl | pyrimidin-2,5-diyl | 2-trifluoromethylphenyl |
| | 13 | H | CH$_2$SEt | pyrimidin-2,5-diyl | 2-trifluoromethylphenyl |
| | 14 | H | CH$_2$SO$_2$Et | pyrimidin-2,5-diyl | 2-trifluoromethylphenyl |
| | 15 | H | CF$_3$ | pyrimidin-2,5-diyl | 2-trifluoromethylphenyl |
| | 16 | H | CH$_3$ | pyrimidin-2,5-diyl | 2-trifluoromethylphenyl |
| | 17 | H | H | pyrimidin-2,5-diyl | 2-trifluoromethylphenyl |
| D4 | 1 | H | CH$_2$OMe | 2-fluoro-1,4-phenylene | 2-trifluoromethylphenyl |

TABLE 7-continued

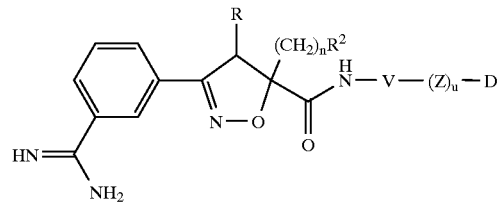

a

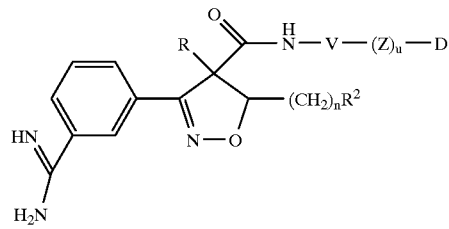

b

| Part | Cpd | R | (CH$_2$)$_2$R$^2$ | V | (Z)$_u$—D |
|---|---|---|---|---|---|
| | 2 | H | CH$_2$OEt | 2-fluoro-1,4-phenylene | 2-trifluoromethylphenyl |
| | 3 | H | CH$_2$O-n-Pr | 2-fluoro-1,4-phenylene | 2-trifluoromethylphenyl |
| | 4 | H | CH$_2$O-i-Pr | 2-fluoro-1,4-phenylene | 2-trifluoromethylphenyl |
| | 5 | H | CH$_2$O-n-Bu | 2-fluoro-1,4-phenylene | 2-trifluoromethylphenyl |
| | 6 | H | CH$_2$O-i-Bu | 2-fluoro-1,4-phenylene | 2-trifluoromethylphenyl |
| | 7 | H | CH$_2$Ph | 2-fluoro-1,4-phenylene | 2-trifluoromethylphenyl |
| | 8 | H | CH$_2$-pyrazol-1-yl | 2-fluoro-1,4-phenylene | 2-trifluoromethylphenyl |
| | 9 | H | CH$_2$-imidazol-1-yl | 2-fluoro-1,4-phenylene | 2-trifluoromethylphenyl |
| | 10 | H | CH$_2$tetrazol-1-yl | 2-fluoro-1,4-phenylene | 2-trifluoromethylphenyl |
| | 11 | H | CH$_2$tetrazol-2-yl | 2-fluoro-1,4-phenylene | 2-trifluoromethylphenyl |
| | 12 | H | CH$_2$-triazol-1-yl | 2-fluoro-1,4-phenylene | 2-trifluoromethylphenyl |
| | 13 | H | CH$_2$SEt | 2-fluoro-1,4-phenylene | 2-trifluoromethylphenyl |
| | 14 | H | CH$_2$SO$_2$Et | 2-fluoro-1,4-phenylene | 2-trifluoromethylphenyl |
| | 15 | H | CF$_3$ | 2-fluoro-1,4-phenylene | 2-trifluoromethylphenyl |
| | 16 | H | CH$_3$ | 2-fluoro-1,4-phenylene | 2-trifluoromethylphenyl |
| | 17 | H | H | 2-fluoro-1,4-phenylene | 2-trifluoromethylphenyl |
| D5 | 1 | H | CH$_2$OMe | 2-chloro-1,4-phenylene | 2-trifluoromethylphenyl |
| | 2 | H | CH$_2$OEt | 2-chloro-1,4-phenylene | 2-trifluoromethylphenyl |
| | 3 | H | CH$_2$O-n-Pr | 2-chloro-1,4-phenylene | 2-trifluoromethylphenyl |
| | 4 | H | CH$_2$O-i-Pr | 2-chloro-1,4-phenylene | 2-trifluoromethylphenyl |
| | 5 | H | CH$_2$O-n-Bu | 2-chloro-1,4-phenylene | 2-trifluoromethylphenyl |
| | 6 | H | CH$_2$O-i-Bu | 2-chloro-1,4-phenylene | 2-trifluoromethylphenyl |
| | 7 | H | CH$_2$Ph | 2-chloro-1,4-phenylene | 2-trifluoromethylphenyl |
| | 8 | H | CH$_2$-pyrazol-1-yl | 2-chloro-1,4-phenylene | 2-trifluoromethylphenyl |
| | 9 | H | CH$_2$-imidazol-1-yl | 2-chloro-1,4-phenylene | 2-trifluoromethylphenyl |
| | 10 | H | CH$_2$-tetrazol-1-yl | 2-chloro-1,4-phenylene | 2-trifluoromethylphenyl |
| | 11 | H | CH$_2$-tetrazol-2-yl | 2-chloro-1,4-phenylene | 2-trifluoromethylphenyl |
| | 12 | H | CH$_2$-triazol-1-yl | 2-chloro-1,4-phenylene | 2-trifluoromethylphenyl |
| | 13 | H | CH$_2$SEt | 2-chloro-1,4-phenylene | 2-trifluoromethylphenyl |
| | 14 | H | CH$_2$SO$_2$Et | 2-chloro-1,4-phenylene | 2-trifluoromethylphenyl |
| | 15 | H | CF$_3$ | 2-chloro-1,4-phenylene | 2-trifluoromethylphenyl |
| | 16 | H | CH$_3$ | 2-chloro-1,4-phenylene | 2-trifluoromethylphenyl |
| | 17 | H | H | 2-chloro-1,4-phenylene | 2-trifluoromethylphenyl |
| D6 | 1 | H | CH$_2$OMe | 2-methyl-1,4-phenylene | 2-trifluoromethylphenyl |
| | 2 | H | CH$_2$OEt | 2-methyl-1,4-phenylene | 2-trifluoromethylphenyl |
| | 3 | H | CH$_2$O-n-Pr | 2-methyl-1,4-phenylene | 2-trifluoromethylphenyl |
| | 4 | H | CH$_2$O-i-Pr | 2-methyl-1,4-phenylene | 2-trifluoromethylphenyl |
| | 5 | H | CH$_2$O-n-Bu | 2-methyl-1,4-phenylene | 2-trifluoromethylphenyl |
| | 6 | H | CH$_2$O-i-Bu | 2-methyl-1,4-phenylene | 2-trifluoromethylphenyl |
| | 7 | H | CH$_2$Ph | 2-methyl-1,4-phenylene | 2-trifluoromethylphenyl |
| | 8 | H | CH$_2$-pyrazol-1-yl | 2-methyl-1,4-phenylene | 2-trifluoromethylphenyl |
| | 9 | H | CH$_2$-imidazol-1-yl | 2-methyl-1,4-phenylene | 2-trifluoromethylphenyl |
| | 10 | H | CH$_2$-tetrazol-1-yl | 2-methyl-1,4-phenylene | 2-trifluoromethylphenyl |
| | 11 | H | CH$_2$-tetrazol-2-yl | 2-methyl-1,4-phenylene | 2-trifluoromethylphenyl |
| | 12 | H | CH$_2$-triazol-1-yl | 2-methyl-1,4-phenylene | 2-trifluoromethylphenyl |
| | 13 | H | CH$_2$SEt | 2-methyl-1,4-phenylene | 2-trifluoromethylphenyl |
| | 14 | H | CH$_2$SO$_2$Et | 2-methyl-1,4-phenylene | 2-trifluoromethylphenyl |
| | 15 | H | CF$_3$ | 2-methyl-1,4-phenylene | 2-trifluoromethylphenyl |
| | 16 | H | CH$_3$ | 2-methyl-1,4-phenylene | 2-trifluoromethylphenyl |
| | 17 | H | H | 2-methyl-1,4-phenylene | 2-trifluoromethylphenyl |
| E1 | 1 | H | CH$_2$OMe | 1,4-phenylene | 2-trifluoromethoxyphenyl |

TABLE 7-continued

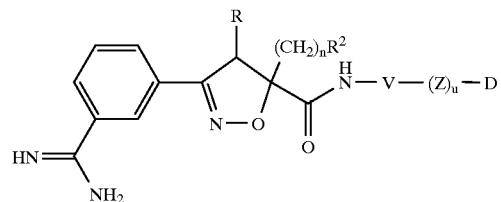

a

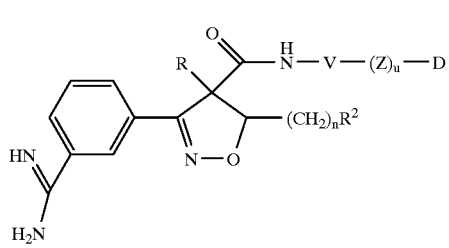

b

| Part | Cpd | R | (CH₂)₂R² | V | (Z)ᵤ—D |
|------|-----|---|----------|---|--------|
|  | 2 | H | CH₂OEt | 1,4-phenylene | 2-trifluoromethoxyphenyl |
|  | 3 | H | CH₂O-n-Pr | 1,4-phenylene | 2-trifluoromethoxyphenyl |
|  | 4 | H | CH₂O-i-Pr | 1,4-phenylene | 2-trifluoromethoxyphenyl |
|  | 5 | H | CH₂O-n-Bu | 1,4-phenylene | 2-trifluoromethoxyphenyl |
|  | 6 | H | CH₂O-i-Bu | 1,4-phenylene | 2-trifluoromethoxyphenyl |
|  | 7 | H | CH₂Ph | 1,4-phenylene | 2-trifluoromethoxyphenyl |
|  | 8 | H | CH₂-pyrazol-1-yl | 1,4-phenylene | 2-trifluoromethoxyphenyl |
|  | 9 | H | CH₂-imidazol-1-yl | 1,4-phenylene | 2-trifluoromethoxyphenyl |
|  | 10 | H | CH₂-tetrazol-1-yl | 1,4-phenylene | 2-trifluoromethoxyphenyl |
|  | 11 | H | CH₂-tetrazol-2-yl | 1,4-phenylene | 2-trifluoromethoxyphenyl |
|  | 12 | H | CH₂-triazol-1-yl | 1,4-phenylene | 2-trifluoromethoxyphenyl |
|  | 13 | H | CH₂SEt | 1,4-phenylene | 2-trifluoromethoxyphenyl |
|  | 14 | H | CH₂SO₂Et | 1,4-phenylene | 2-trifluoromethoxyphenyl |
|  | 15 | H | CF₃ | 1,4-phenylene | 2-trifluoromethoxyphenyl |
|  | 16 | H | CH₃ | 1,4-phenylene | 2-trifluoromethoxyphenyl |
|  | 17 | H | H | 1,4-phenylene | 2-trifluoromethoxyphenyl |
| E2 | 1 | H | CH₂OMe | pyridin-2,5-diyl | 2-trifluoromethoxyphenyl |
|  | 2 | H | CH₂OEt | pyridin-2,5-diyl | 2-trifluoromethoxyphenyl |
|  | 3 | H | CH₂O-n-Pr | pyridin-2,5-diyl | 2-trifluoromethoxyphenyl |
|  | 4 | H | CH₂O-i-Pr | pyridin-2,5-diyl | 2-trifluoromethoxyphenyl |
|  | 5 | H | CH₂O-n-Bu | pyridin-2,5-diyl | 2-trifluoromethoxyphenyl |
|  | 6 | H | CH₂O-i-Bu | pyridin-2,5-diyl | 2-trifluoromethoxyphenyl |
|  | 7 | H | CH₂Ph | pyridin-2,5-diyl | 2-trifluoromethoxyphenyl |
|  | 8 | H | CH₂-pyrazol-1-yl | pyridin-2,5-diyl | 2-trifluoromethoxyphenyl |
|  | 9 | H | CH₂-imidazol-1-yl | pyridin-2,5-diyl | 2-trifluoromethoxyphenyl |
|  | 10 | H | CH₂-tetrazol-1-yl | pyridin-2,5-diyl | 2-trifluoromethoxyphenyl |
|  | 11 | H | CH₂-tetrazol-2-yl | pyridin-2,5-diyl | 2-trifluoromethoxyphenyl |
|  | 12 | H | CH₂-triazol-1-yl | pyridin-2,5-diyl | 2-trifluoromethoxyphenyl |
|  | 13 | H | CH₂SEt | pyridin-2,5-diyl | 2-trifluoromethoxyphenyl |
|  | 14 | H | CH₂SO₂Et | pyridin-2,5-diyl | 2-trifluoromethoxyphenyl |
|  | 15 | H | CF₃ | pyridin-2,5-diyl | 2-trifluoromethoxyphenyl |
|  | 16 | H | CH₃ | pyridin-2,5-diyl | 2-trifluoromethoxyphenyl |
|  | 17 | H | H | pyridin-2,5-diyl | 2-trifluoromethoxyphenyl |
| E3 | 1 | H | CH₂OMe | pyrimidin-2,5-diyl | 2-trifluoromethoxyphenyl |
|  | 2 | H | CH₂OEt | pyrimidin-2,5-diyl | 2-trifluoromethoxyphenyl |
|  | 3 | H | CH₂O-n-Pr | pyrimidin-2,5-diyl | 2-trifluoromethoxyphenyl |
|  | 4 | H | CH₂O-i-Pr | pyrimidin-2,5-diyl | 2-trifluoromethoxyphenyl |
|  | 5 | H | CH₂O-n-Bu | pyrimidin-2,5-diyl | 2-trifluoromethoxyphenyl |
|  | 6 | H | CH₂O-i-Bu | pyrimidin-2,5-diyl | 2-trifluoromethoxyphenyl |
|  | 7 | H | CH₂Ph | pyrimidin-2,5-diyl | 2-trifluoromethoxyphenyl |
|  | 8 | H | CH₂-pyrazol-1-yl | pyrimidin-2,5-diyl | 2-trifluoromethoxyphenyl |
|  | 9 | H | CH₂-imidazol-1-yl | pyrimidin-2,5-diyl | 2-trifluoromethoxyphenyl |
|  | 10 | H | CH₂-tetrazol-1-yl | pyrimidin-2,5-diyl | 2-trifluoromethoxyphenyl |
|  | 11 | H | CH₂-tetrazol-2-yl | pyrimidin-2,5-diyl | 2-trifluoromethoxyphenyl |
|  | 12 | H | CH₂-triazol-1-yl | pyrimidin-2,5-diyl | 2-trifluoromethoxyphenyl |
|  | 13 | H | CH₂SEt | pyrimidin-2,5-diyl | 2-trifluoromethoxyphenyl |
|  | 14 | H | CH₂SO₂Et | pyrimidin-2,5-diyl | 2-trifluoromethoxyphenyl |
|  | 15 | H | CF₃ | pyrimidin-2,5-diyl | 2-trifluoromethoxyphenyl |
|  | 16 | H | CH₃ | pyrimidin-2,5-diyl | 2-trifluoromethoxyphenyl |
|  | 17 | H | H | pyrimidin-2,5-diyl | 2-trifluoromethoxyphenyl |
| E4 | 1 | H | CH₂OMe | 2-fluoro-1,4-phenylene | 2-trifluoromethoxyphenyl |

TABLE 7-continued

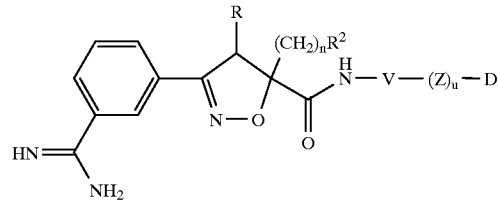

a

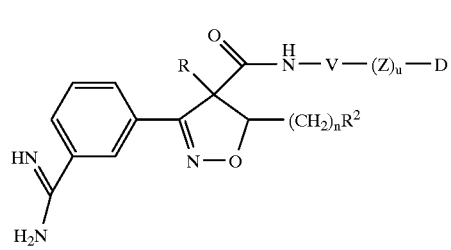

b

| Part | Cpd | R | (CH$_2$)$_2$R$^2$ | V | (Z)$_u$—D |
|---|---|---|---|---|---|
| | 2 | H | CH$_2$OEt | 2-fluoro-1,4-phenylene | 2-trifluoromethoxyphenyl |
| | 3 | H | CH$_2$O-n-Pr | 2-fluoro-1,4-phenylene | 2-trifluoromethoxyphenyl |
| | 4 | H | CH$_2$O-i-Pr | 2-fluoro-1,4-phenylene | 2-trifluoromethoxyphenyl |
| | 5 | H | CH$_2$O-n-Bu | 2-fluoro-1,4-phenylene | 2-trifluoromethoxyphenyl |
| | 6 | H | CH$_2$O-i-Bu | 2-fluoro-1,4-phenylene | 2-trifluoromethoxyphenyl |
| | 7 | H | CH$_2$Ph | 2-fluoro-1,4-phenylene | 2-trifluoromethoxyphenyl |
| | 8 | H | CH$_2$-pyrazol-1-yl | 2-fluoro-1,4-phenylene | 2-trifluoromethoxyphenyl |
| | 9 | H | CH$_2$-imidazol-1-yl | 2-fluoro-1,4-phenylene | 2-trifluoromethoxyphenyl |
| | 10 | H | CH$_2$-tetrazol-1-yl | 2-fluoro-1,4-phenylene | 2-trifluoromethoxyphenyl |
| | 11 | H | CH$_2$-tetrazol-2-yl | 2-fluoro-1,4-phenylene | 2-trifluoromethoxyphenyl |
| | 12 | H | CH$_2$-triazol-1-yl | 2-fluoro-1,4-phenylene | 2-trifluoromethoxyphenyl |
| | 13 | H | CH$_2$SEt | 2-fluoro-1,4-phenylene | 2-trifluoromethoxyphenyl |
| | 14 | H | CH$_2$SO$_2$Et | 2-fluoro-1,4-phenylene | 2-trifluoromethoxyphenyl |
| | 15 | H | CF$_3$ | 2-fluoro-1,4-phenylene | 2-trifluoromethoxyphenyl |
| | 16 | H | CH$_3$ | 2-fluoro-1,4-phenylene | 2-trifluoromethoxyphenyl |
| | 17 | H | H | 2-fluoro-1,4-phenylene | 2-trifluoromethoxyphenyl |
| E5 | 1 | H | CH$_2$OMe | 2-chloro-1,4-phenylene | 2-trifluoromethoxyphenyl |
| | 2 | H | CH$_2$OEt | 2-chloro-1,4-phenylene | 2-trifluoromethoxyphenyl |
| | 3 | H | CH$_2$O-n-Pr | 2-chloro-1,4-phenylene | 2-trifluoromethoxyphenyl |
| | 4 | H | CH$_2$O-i-Pr | 2-chloro-1,4-phenylene | 2-trifluoromethoxyphenyl |
| | 5 | H | CH$_2$O-n-Bu | 2-chloro-1,4-phenylene | 2-trifluoromethoxyphenyl |
| | 6 | H | CH$_2$O-i-Bu | 2-chloro-1,4-phenylene | 2-trifluoromethoxyphenyl |
| | 7 | H | CH$_2$Ph | 2-chloro-1,4-phenylene | 2-trifluoromethoxyphenyl |
| | 8 | H | CH$_2$-pyrazol-1-yl | 2-chloro-1,4-phenylene | 2-trifluoromethoxyphenyl |
| | '9 | H | CH$_2$-imidazol-1-yl | 2-chloro-1,4-phenylene | 2-trifluoromethoxyphenyl |
| | 10 | H | CH$_2$-tetrazol-1-yl | 2-chloro-1,4-phenylene | 2-trifluoromethoxyphenyl |
| | 11 | H | CH$_2$-tetrazol-2-yl | 2-chloro-1,4-phenylene | 2-trifluoromethoxyphenyl |
| | 12 | H | CH$_2$-triazol-1-yl | 2-chloro-1,4-phenylene | 2-trifluoromethoxyphenyl |
| | 13 | H | CH$_2$SEt | 2-chloro-1,4-phenylene | 2-trifluoromethoxyphenyl |
| | 14 | H | CH$_2$SO$_2$Et | 2-chloro-1,4-phenylene | 2-trifluoromethoxyphenyl |
| | 15 | H | CF$_3$ | 2-chloro-1,4-phenylene | 2-trifluoromethoxyphenyl |
| | 16 | H | CH$_3$ | 2-chloro-1,4-phenylene | 2-trifluoromethoxyphenyl |
| | 17 | H | H | 2-chloro-1,4-phenylene | 2-trifluoromethoxyphenyl |
| E6 | 1 | H | CH$_2$OMe | 2-methyl-1,4-phenylene | 2-trifluoromethoxyphenyl |
| | 2 | H | CH$_2$OEt | 2-methyl-1,4-phenylene | 2-trifluoromethoxyphenyl |
| | 3 | H | CH$_2$O-n-Pr | 2-methyl-1,4-phenylene | 2-trifluoromethoxyphenyl |
| | 4 | H | CH$_2$O-i-Pr | 2-methyl-1,4-phenylene | 2-trifluoromethoxyphenyl |
| | 5 | H | CH$_2$O-n-Bu | 2-methyl-1,4-phenylene | 2-trifluoromethoxyphenyl |
| | 6 | H | CH$_2$O-i-Bu | 2-methyl-1,4-phenylene | 2-trifluoromethoxyphenyl |
| | 7 | H | CH$_2$Ph | 2-methyl-1,4-phenylene | 2-trifluoromethoxyphenyl |
| | 8 | H | CH$_2$-pyrazol-1-yl | 2-methyl-1,4-phenylene | 2-trifluoromethoxyphenyl |
| | 9 | H | CH$_2$-imidazol-1-yl | 2-methyl-1,4-phenylene | 2-trifluoromethoxyphenyl |
| | 10 | H | CH$_2$-tetrazol-1-yl | 2-methyl-1,4-phenylene | 2-trifluoromethoxyphenyl |
| | 11 | H | CH$_2$-tetrazol-2-yl | 2-methyl-1,4-phenylene | 2-trifluoromethoxyphenyl |
| | 12 | H | CH$_2$-triazol-1-yl | 2-methyl-1,4-phenylene | 2-trifluoromethoxyphenyl |
| | 13 | H | CH$_2$SEt | 2-methyl-1,4-phenylene | 2-trifluoromethoxyphenyl |
| | 14 | H | CH$_2$SO$_2$Et | 2-methyl-1,4-phenylene | 2-trifluoromethoxyphenyl |
| | 15 | H | CF$_3$ | 2-methyl-1,4-phenylene | 2-trifluoromethoxyphenyl |
| | 16 | H | CH$_3$ | 2-methyl-1,4-phenylene | 2-trifluoromethoxyphenyl |
| | 17 | H | H | 2-methyl-1,4-phenylene | 2-trifluoromethoxyphenyl |
| F1 | 1 | H | CH$_2$OMe | 1,4-phenylene | 2-trifluoromethyl- |

TABLE 7-continued

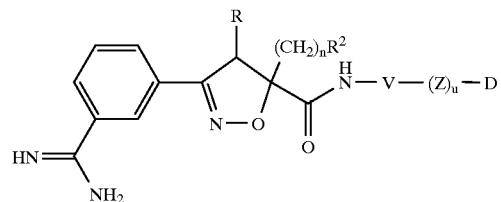

a

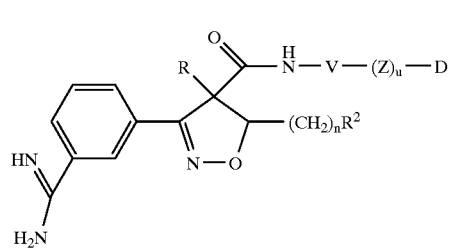

b

| Part | Cpd | R | $(CH_2)_2R^2$ | V | $(Z)_u-D$ |
|---|---|---|---|---|---|
| | | | | | sulfonyl-phenyl |
| | 2 | H | $CH_2OEt$ | 1,4-phenylene | 2-trifluoromethyl-sulfonyl-phenyl |
| | 3 | H | $CH_2O$-n-Pr | 1,4-phenylene | 2-trifluoromethyl-sulfonyl-phenyl |
| | 4 | H | $CH_2O$-i-Pr | 1,4-phenylene | 2-trifluoromethyl-sulfonyl-phenyl |
| | 5 | H | $CH_2O$-n-Bu | 1,4-phenylene | 2-trifluoromethyl-sulfonyl-phenyl |
| | 6 | H | $CH_2O$-i-Bu | 1,4-phenylene | 2-trifluoromethyl-sulfonyl-phenyl |
| | 7 | H | $CH_2Ph$ | 1,4-phenylene | 2-trifluoromethyl-sulfonyl-phenyl |
| | 8 | H | $CH_2$-pyrazol-1-yl | 1,4-phenylene | 2-trifluoromethyl-sulfonyl-phenyl |
| | 9 | H | $CH_2$-imidazol-1-yl | 1,4-phenylene | 2-trifluoromethyl-sulfonyl-phenyl |
| | 10 | H | $CH_2$-tetrazol-1-yl | 1,4-phenylene | 2-trifluoromethyl-sulfonyl-phenyl |
| | 11 | H | $CH_2$-tetrazol-2-yl | 1,4-phenylene | 2-trifluoromethyl-sulfonyl-phenyl |
| | 12 | H | $CH_2$-triazol-1-yl | 1,4-phenylene | 2-trifluoromethyl-sulfonyl-phenyl |
| | 13 | H | $CH_2SEt$ | 1,4-phenylene | 2-trifluoromethyl-sulfonyl-phenyl |
| | 14 | H | $CH_2SO_2Et$ | 1,4-phenylene | 2-trifluoromethyl-sulfonyl-phenyl |
| | 15 | H | $CF_3$ | 1,4-phenylene | 2-trifluoromethyl-sulfonyl-phenyl |
| | 16 | H | $CH_3$ | 1,4-phenylene | 2-trifluoromethyl-sulfonyl-phenyl |
| | 17 | H | H | 1,4-phenylene | 2-trifluoromethyl-sulfonyl-phenyl |
| F2 | 1 | H | $CH_2OMe$ | pyridin-2,5-diyl | 2-trifluoromethyl-sulfonyl-phenyl |
| | 2 | H | $CH_2OEt$ | pyridin-2,5-diyl | 2-trifluoromethyl-sulfonyl-phenyl |
| | 3 | H | $CH_2O$-n-Pr | pyridin-2,5-diyl | 2-trifluoromethyl-sulfonyl-phenyl |
| | 4 | H | $CH_2O$-i-Pr | pyridin-2,5-diyl | 2-trifluoromethyl-sulfonyl-phenyl |
| | 5 | H | $CH_2O$-n-Bu | pyridin-2,5-diyl | 2-trifluoromethyl-sulfonyl-phenyl |
| | 6 | H | $CH_2O$-i-Bu | pyridin-2,5-diyl | 2-trifluoromethyl-sulfonyl-phenyl |
| | 7 | H | $CH_2Ph$ | pyridin-2,5-diyl | 2-trifluoromethyl-sulfonyl-phenyl |
| | 8 | H | $CH_2$-pyrazol-1-yl | pyridin-2,5-diyl | 2-trifluoromethyl-sulfonyl-phenyl |
| | 9 | H | $CH_2$-imidazol-1-yl | pyridin-2,5-diyl | 2-trifluoromethyl-sulfonyl-phenyl |

TABLE 7-continued

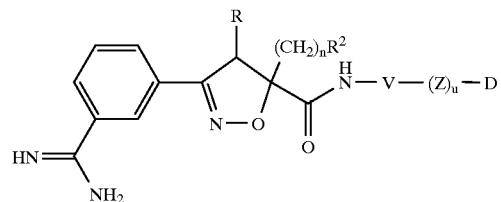

a

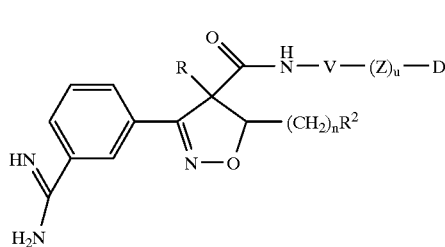

b

| Part | Cpd | R | (CH₂)₂R² | V | (Z)ᵤ—D |
|------|-----|---|----------|---|--------|
|  | 10 | H | CH₂-tetrazol-1-yl | pyridin-2,5-diyl | 2-trifluoromethyl-sulfonyl-phenyl |
|  | 11 | H | CH₂-tetrazol-2-yl | pyridin-2,5-diyl | 2-trifluoromethyl-sulfonyl-phenyl |
|  | 12 | H | CH₂-triazol-1-yl | pyridin-2,5-diyl | 2-trifluoromethyl-sulfonyl-phenyl |
|  | 13 | H | CH₂SEt | pyridin-2,5-diyl | 2-trifluoromethyl-sulfonyl-phenyl |
|  | 14 | H | CH₂SO₂Et | pyridin-2,5-diyl | 2-trifluoromethyl-sulfonyl-phenyl |
|  | 15 | H | CF₃ | pyridin-2,5-diyl | 2-trifluoromethyl-sulfonyl-phenyl |
|  | 16 | H | CH₃ | pyridin-2,5-diyl | 2-trifluoromethyl-sulfonyl-phenyl |
|  | 17 | H | H | pyridin-2,5-diyl | 2-trifluoromethyl-sulfonyl-phenyl |
| F3 | 1 | H | CH₂OMe | pyrimidin-2,5-diyl | 2-trifluoromethyl-sulfonyl-phenyl |
|  | 2 | H | CH₂OEt | pyrimidin-2,5-diyl | 2-trifluoromethyl-sulfonyl-phenyl |
|  | 3 | H | CH₂O-n-Pr | pyrimidin-2,5-diyl | 2-trifluoromethyl-sulfonyl-phenyl |
|  | 4 | H | CH₂O-i-Pr | pyrimidin-2,5-diyl | 2-trifluoromethyl-sulfonyl-phenyl |
|  | 5 | H | CH₂O-n-Bu | pyrimidin-2,5-diyl | 2-trifluoromethyl-sulfonyl-phenyl |
|  | 6 | H | CH₂O-i-Bu | pyrimidin-2,5-diyl | 2-trifluoromethyl-sulfonyl-phenyl |
|  | 7 | H | CH₂Ph | pyrimidin-2,5-diyl | 2-trifluoromethyl-sulfonyl-phenyl |
|  | 8 | H | CH₂-pyrazol-1-yl | pyrimidin-2,5-diyl | 2-trifluoromethyl-sulfonyl-phenyl |
|  | 9 | H | CH₂-imidazol-1-yl | pyrimidin-2,5-diyl | 2-trifluoromethyl-sulfonyl-phenyl |
|  | 10 | H | CH₂-tetrazol-1-yl | pyrimidin-2,5-diyl | 2-trifluoromethyl-sulfonyl-phenyl |
|  | 11 | H | CH₂-tetrazol-2-yl | pyrimidin-2,5-diyl | 2-trifluoromethyl-sulfonyl-phenyl |
|  | 12 | H | CH₂-triazol-1-yl | pyrimidin-2,5-diyl | 2-trifluoromethyl-sulfonyl-phenyl |
|  | 13 | H | CH₂SEt | pyrimidin-2,5-diyl | 2-trifluoromethyl-sulfonyl-phenyl |
|  | 14 | H | CH₂SO₂Et | pyrimidin-2,5-diyl | 2-trifluoromethyl-sulfonyl-phenyl |
|  | 15 | H | CF₃ | pyrimidin-2,5-diyl | 2-trifluoromethyl-sulfonyl-phenyl |
|  | 16 | H | CH₃ | pyrimidin-2,5-diyl | 2-trifluoromethyl-sulfonyl-phenyl |
|  | 17 | H | H | pyrimidin-2,5-diyl | 2-trifluoromethyl-sulfonyl-phenyl |
| F4 | 1 | H | CH₂OMe | 2-fluoro-1,4-phenylene | 2-trifluoromethyl- |

TABLE 7-continued a b

| Part | Cpd | R | (CH$_2$)$_2$R$^2$ | V | (Z)$_u$—D |
|------|-----|---|-------------------|---|-----------|
| | 2 | H | CH$_2$OEt | 2-fluoro-1,4-phenylene | 2-trifluoromethyl-sulfonyl-phenyl |
| | 3 | H | CH$_2$O-n-Pr | 2-fluoro-1,4-phenylene | 2-trifluoromethyl-sulfonyl-phenyl |
| | 4 | H | CH$_2$O-i-Pr | 2-fluoro-1,4-phenylene | 2-trifluoromethyl-sulfonyl-phenyl |
| | 5 | H | CH$_2$O-n-Bu | 2-fluoro-1,4-phenylene | 2-trifluoromethyl-sulfonyl-phenyl |
| | 6 | H | CH$_2$O-i-Bu | 2-fluoro-1,4-phenylene | 2-trifluoromethyl-sulfonyl-phenyl |
| | 7 | H | CH$_2$Ph | 2-fluoro-1,4-phenylene | 2-trifluoromethyl-sulfonyl-phenyl |
| | 8 | H | CH$_2$-pyrazol-1-yl | 2-fluoro-1,4-phenylene | 2-trifluoromethyl-sulfonyl-phenyl |
| | 9 | H | CH$_2$-imidazol-1-yl | 2-fluoro-1,4-phenylene | 2-trifluoromethyl-sulfonyl-phenyl |
| | 10 | H | CH$_2$-tetrazol-1-yl | 2-fluoro-1,4-phenylene | 2-trifluoromethyl-sulfonyl-phenyl |
| | 11 | H | CH$_2$-tetrazol-2-yl | 2-fluoro-1,4-phenylene | 2-trifluoromethyl-sulfonyl-phenyl |
| | 12 | H | CH$_2$-triazol-1-yl | 2-fluoro-1,4-phenylene | 2-trifluoromethyl-sulfonyl-phenyl |
| | 13 | H | CH$_2$SEt | 2-fluoro-1,4-phenylene | 2-trifluoromethyl-sulfonyl-phenyl |
| | 14 | H | CH$_2$SO$_2$Et | 2-fluoro-1,4-phenylene | 2-trifluoromethyl-sulfonyl-phenyl |
| | 15 | H | CF$_3$ | 2-fluoro-1,4-phenylene | 2-trifluoromethyl-sulfonyl-phenyl |
| | 16 | H | CH$_3$ | 2-fluoro-1,4-phenylene | 2-trifluoromethyl-sulfonyl-phenyl |
| | 17 | H | H | 2-fluoro-1,4-phenylene | 2-trifluoromethyl-sulfonyl-phenyl |
| F5 | 1 | H | CH$_2$OMe | 2-chloro-1,4-phenylene | 2-trifluoromethyl-sulfonyl-phenyl |
| | 2 | H | CH$_2$OEt | 2-chloro-1,4-phenylene | 2-trifluoromethyl-sulfonyl-phenyl |
| | 3 | H | CH$_2$O-n-Pr | 2-chloro-1,4-phenylene | 2-trifluoromethyl-sulfonyl-phenyl |
| | 4 | H | CH$_2$O-i-Pr | 2-chloro-1,4-phenylene | 2-trifluoromethyl-sulfonyl-phenyl |
| | 5 | H | CH$_2$O-n-Bu | 2-chloro-1,4-phenylene | 2-trifluoromethyl-sulfonyl-phenyl |
| | 6 | H | CH$_2$O-i-Bu | 2-chloro-1,4-phenylene | 2-trifluoromethyl-sulfonyl-phenyl |
| | 7 | H | CH$_2$Ph | 2-chloro-1,4-phenylene | 2-trifluoromethyl-sulfonyl-phenyl |
| | 8 | H | CH$_2$-pyrazol-1-yl | 2-chloro-1,4-phenylene | 2-trifluoromethyl-sulfonyl-phenyl |
| | 9 | H | CH$_2$-imidazol-1-yl | 2-chloro-1,4-phenylene | 2-trifluoromethyl-sulfonyl-phenyl |

TABLE 7-continued

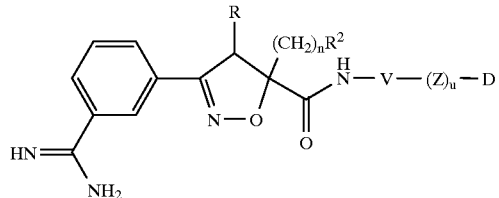

a

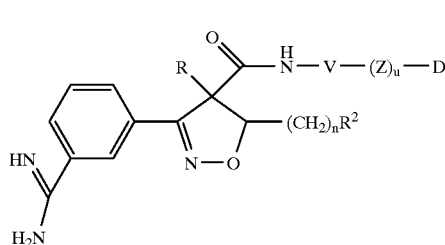

b

| Part | Cpd | R | (CH$_2$)$_2$R$^2$ | V | (Z)$_u$—D |
|---|---|---|---|---|---|
| | 10 | H | CH$_2$-tetrazol-1-yl | 2-chloro-1,4-phenylene | 2-trifluoromethyl-sulfonyl-phenyl |
| | 11 | H | CH$_2$-tetrazol-2-yl | 2-chloro-1,4-phenylene | 2-trifluoromethyl-sulfonyl-phenyl |
| | 12 | H | CH$_2$-triazol-1-yl | 2-chloro-1,4-phenylene | 2-trifluoromethyl-sulfonyl-phenyl |
| | 13 | H | CH$_2$SEt | 2-chloro-1,4-phenylene | 2-trifluoromethyl-sulfonyl-phenyl |
| | 14 | H | CH$_2$SO$_2$Et | 2-chloro-1,4-phenylene | 2-trifluoromethyl-sulfonyl-phenyl |
| | 15 | H | CF$_3$ | 2-chloro-1,4-phenylene | 2-trifluoromethyl-sulfonyl-phenyl |
| | 16 | H | CH$_3$ | 2-chloro-1,4-phenylene | 2-trifluoromethyl-sulfonyl-phenyl |
| | 17 | H | H | 2-chloro-1,4-phenylene | 2-trifluoromethyl-sulfonyl-phenyl |
| F6 | 1 | H | CH$_2$OMe | 2-methyl-1,4-phenylene | 2-trifluoromethyl-sulfonyl-phenyl |
| | 2 | H | CH$_2$OEt | 2-methyl-1,4-phenylene | 2-trifluoromethyl-sulfonyl-phenyl |
| | 3 | H | CH$_2$O-n-Pr | 2-methyl-1,4-phenylene | 2-trifluoromethyl-sulfonyl-phenyl |
| | 4 | H | CH$_2$O-i-Pr | 2-methyl-1,4-phenylene | 2-trifluoromethyl-sulfonyl-phenyl |
| | 5 | H | CH$_2$O-n-Bu | 2-methyl-1,4-phenylene | 2-trifluoromethyl-sulfonyl-phenyl |
| | 6 | H | CH$_2$O-i-Bu | 2-methyl-1,4-phenylene | 2-trifluoromethyl-sulfonyl-phenyl |
| | 7 | H | CH$_2$Ph | 2-methyl-1,4-phenylene | 2-trifluoromethyl-sulfonyl-phenyl |
| | 8 | H | CH$_2$-pyrazol-1-yl | 2-methyl-1,4-phenylene | 2-trifluoromethyl-sulfonyl-phenyl |
| | 9 | H | CH$_2$-imidazol-1-yl | 2-methyl-1,4-phenylene | 2-trifluoromethyl-sulfonyl-phenyl |
| | 10 | H | CH$_2$-tetrazol-1-yl | 2-methyl-1,4-phenylene | 2-trifluoromethyl-sulfonyl-phenyl |
| | 11 | H | CH$_2$-tetrazol-2-yl | 2-methyl-1,4-phenylene | 2-trifluoromethyl-sulfonyl-phenyl |
| | 12 | H | CH$_2$-triazol-1-yl | 2-methyl-1,4-phenylene | 2-trifluoromethyl-sulfonyl-phenyl |
| | 13 | H | CH$_2$SEt | 2-methyl-1,4-phenylene | 2-trifluoromethyl-sulfonyl-phenyl |
| | 14 | H | CH$_2$SO$_2$Et | 2-methyl-1,4-phenylene | 2-trifluoromethyl-sulfonyl-phenyl |
| | 15 | H | CF$_3$ | 2-methyl-1,4-phenylene | 2-trifluoromethyl-sulfonyl-phenyl |
| | 16 | H | CH$_3$ | 2-methyl-1,4-phenylene | 2-trifluoromethyl-sulfonyl-phenyl |
| | 17 | H | H | 2-methyl-1,4-phenylene | 2-trifluoromethyl-sulfonyl-phenyl |
| G1 | 1 | H | CH$_2$OMe | phenyl | 2-methoxyphenyl |

TABLE 7-continued a

[Structure a: 3-(3-carbamimidoylphenyl)-isoxazoline with R, (CH₂)ₙR² substituents and C(O)NH-V-(Z)ᵤ-D carboxamide at 5-position]

b

[Structure b: regioisomer with carboxamide at 4-position and (CH₂)ₙR² at 5-position]

| Part | Cpd | R | (CH₂)₂R² | V | (Z)ᵤ—D |
|---|---|---|---|---|---|
| | 2 | H | CH₂OEt | phenyl | 2-methoxyphenyl |
| | 3 | H | CH₂O-n-Pr | phenyl | 2-methoxyphenyl |
| | 4 | H | CH₂O-i-Pr | phenyl | 2-methoxyphenyl |
| | 5 | H | CH₂O-n-Bu | phenyl | 2-methoxyphenyl |
| | 6 | H | CH₂O-i-Bu | phenyl | 2-methoxyphenyl |
| | 7 | H | CH₂Ph | phenyl | 2-methoxyphenyl |
| | 8 | H | CH₂-pyrazol-1-yl | phenyl | 2-methoxyphenyl |
| | 9 | H | CH₂-imidazol-1-yl | phenyl | 2-methoxyphenyl |
| | 10 | H | CH₂-tetrazol-1-yl | phenyl | 2-methoxyphenyl |
| | 11 | H | CH₂-tetrazol-2-yl | phenyl | 2-methoxyphenyl |
| | 12 | H | CH₂-triazol-1-yl | phenyl | 2-methoxyphenyl |
| | 13 | H | CH₂SEt | phenyl | 2-methoxyphenyl |
| | 14 | H | CH₂SO₂Et | phenyl | 2-methoxyphenyl |
| | 15 | H | CF₃ | phenyl | 2-methoxyphenyl |
| | 16 | H | CH₃ | phenyl | 2-methoxyphenyl |
| | 17 | H | H | phenyl | 2-methoxyphenyl |
| G2 | 1 | H | CH₂OMe | pyridin-2,5-diyl | 2-methoxyphenyl |
| | 2 | H | CH₂OEt | pyridin-2,5-diyl | 2-methoxyphenyl |
| | 3 | H | CH₂O-n-Pr | pyridin-2,5-diyl | 2-methoxyphenyl |
| | 4 | H | CH₂O-i-Pr | pyridin-2,5-diyl | 2-methoxyphenyl |
| | 5 | H | CH₂O-n-Bu | pyridin-2,5-diyl | 2-methoxyphenyl |
| | 6 | H | CH₂O-i-Bu | pyridin-2,5-diyl | 2-methoxyphenyl |
| | 7 | H | CH₂Ph | pyridin-2,5-diyl | 2-methoxyphenyl |
| | 8 | H | CH₂-pyrazol-1-yl | pyridin-2,5-diyl | 2-methoxyphenyl |
| | 9 | H | CH₂-imidazol-1-yl | pyridin-2,5-diyl | 2-methoxyphenyl |
| | 10 | H | CH₂-tetrazol-1-yl | pyridin-2,5-diyl | 2-methoxyphenyl |
| | 11 | H | CH₂-tetrazol-2-yl | pyridin-2,5-diyl | 2-methoxyphenyl |
| | 12 | H | CH₂-triazol-1-yl | pyridin-2,5-diyl | 2-methoxyphenyl |
| | 13 | H | CH₂SEt | pyridin-2,5-diyl | 2-methoxyphenyl |
| | 14 | H | CH₂SO₂Et | pyridin-2,5-diyl | 2-methoxyphenyl |
| | 15 | H | CF₃ | pyridin-2,5-diyl | 2-methoxyphenyl |
| | 16 | H | CH₃ | pyridin-2,5-diyl | 2-methoxyphenyl |
| | 17 | H | H | pyridin-2,5-diyl | 2-methoxyphenyl |
| G3 | 1 | H | CH₂OMe | pyrimidin-2,5-diyl | 2-methoxyphenyl |
| | 2 | H | CH₂OEt | pyrimidin-2,5-diyl | 2-methoxyphenyl |
| | 3 | H | CH₂O-n-Pr | pyrimidin-2,5-diyl | 2-methoxyphenyl |
| | 4 | H | CH₂O-i-Pr | pyrimidin-2,5-diyl | 2-methoxyphenyl |
| | 5 | H | CH₂O-n-Bu | pyrimidin-2,5-diyl | 2-methoxyphenyl |
| | 6 | H | CH₂O-i-Bu | pyrimidin-2,5-diyl | 2-methoxyphenyl |
| | 7 | H | CH₂Ph | pyrimidin-2,5-diyl | 2-methoxyphenyl |
| | 8 | H | CH₂-pyrazol-1-yl | pyrimidin-2,5-diyl | 2-methoxyphenyl |
| | 9 | H | CH₂-imidazol-1-yl | pyrimidin-2,5-diyl | 2-methoxyphenyl |
| | 10 | H | CH₂-tetrazol-1-yl | pyrimidin-2,5-diyl | 2-methoxyphenyl |
| | 11 | H | CH₂-tetrazol-2-yl | pyrimidin-2,5-diyl | 2-methoxyphenyl |
| | 12 | H | CH₂-triazol-1-yl | pyrimidin-2,5-diyl | 2-methoxyphenyl |
| | 13 | H | CH₂SEt | pyrimidin-2,5-diyl | 2-methoxyphenyl |
| | 14 | H | CH₂SO₂Et | pyrimidin-2,5-diyl | 2-methoxyphenyl |
| | 15 | H | CF₃ | pyrimidin-2,5-diyl | 2-methoxyphenyl |
| | 16 | H | CH₃ | pyrimidin-2,5-diyl | 2-methoxyphenyl |
| | 17 | H | H | pyrimidin-2,5-diyl | 2-methoxyphenyl |
| G4 | 1 | H | CH₂OMe | 2-fluoro-1,4-phenylene | 2-methoxyphenyl |

TABLE 7-continued a $$\text{structure a: 3-(3-amidinophenyl)-isoxazoline with R, (CH}_2\text{)}_n\text{R}^2\text{ at 5-position, C(O)NH-V-(Z)}_u\text{-D}$$

b $$\text{structure b: regioisomer with R, C(O)NH-V-(Z)}_u\text{-D at 4-position and (CH}_2\text{)}_n\text{R}^2\text{ at 5-position}$$

| Part | Cpd | R | $(CH_2)_2R^2$ | V | $(Z)_u$—D |
|---|---|---|---|---|---|
|  | 2 | H | $CH_2OEt$ | 2-fluoro-1,4-phenylene | 2-methoxyphenyl |
|  | 3 | H | $CH_2O$-n-Pr | 2-fluoro-1,4-phenylene | 2-methoxyphenyl |
|  | 4 | H | $CH_2O$-i-Pr | 2-fluoro-1,4-phenylene | 2-methoxyphenyl |
|  | 5 | H | $CH_2O$-n-Bu | 2-fluoro-1,4-phenylene | 2-methoxyphenyl |
|  | 6 | H | $CH_2O$-i-Bu | 2-fluoro-1,4-phenylene | 2-methoxyphenyl |
|  | 7 | H | $CH_2Ph$ | 2-fluoro-1,4-phenylene | 2-methoxyphenyl |
|  | 8 | H | $CH_2$-pyrazol-1-yl | 2-fluoro-1,4-phenylene | 2-methoxyphenyl |
|  | 9 | H | $CH_2$-imidazol-1-yl | 2-fluoro-1,4-phenylene | 2-methoxyphenyl |
|  | 10 | H | $CH_2$-tetrazol-1-yl | 2-fluoro-1,4-phenylene | 2-methoxyphenyl |
|  | 11 | H | $CH_2$-tetrazol-2-yl | 2-fluoro-1,4-phenylene | 2-methoxyphenyl |
|  | 12 | H | $CH_2$-triazol-1-yl | 2-fluoro-1,4-phenylene | 2-methoxyphenyl |
|  | 13 | H | $CH_2SEt$ | 2-fluoro-1,4-phenylene | 2-methoxyphenyl |
|  | 14 | H | $CH_2SO_2Et$ | 2-fluoro-1,4-phenylene | 2-methoxyphenyl |
|  | 15 | H | $CF_3$ | 2-fluoro-1,4-phenylene | 2-methoxyphenyl |
|  | 16 | H | $CH_3$ | 2-fluoro-1,4-phenylene | 2-methoxyphenyl |
|  | 17 | H | H | 2-fluoro-1,4-phenylene | 2-methoxyphenyl |
| G5 | 1 | H | $CH_2OMe$ | 2-chloro-1,4-phenylene | 2-methoxyphenyl |
|  | 2 | H | $CH_2OEt$ | 2-chloro-1,4-phenylene | 2-methoxyphenyl |
|  | 3 | H | $CH_2O$-n-Pr | 2-chloro-1,4-phenylene | 2-methoxyphenyl |
|  | 4 | H | $CH_2O$-i-Pr | 2-chloro-1,4-phenylene | 2-methoxyphenyl |
|  | 5 | H | $CH_2O$-n-Bu | 2-chloro-1,4-phenylene | 2-methoxyphenyl |
|  | 6 | H | $CH_2O$-i-Bu | 2-chloro-1,4-phenylene | 2-methoxyphenyl |
|  | 7 | H | $CH_2Ph$ | 2-chloro-1,4-phenylene | 2-methoxyphenyl |
|  | 8 | H | $CH_2$-pyrazol-1-yl | 2-chloro-1,4-phenylene | 2-methoxyphenyl |
|  | 9 | H | $CH_2$-imidazol-1-yl | 2-chloro-1,4-phenylene | 2-methoxyphenyl |
|  | 10 | H | $CH_2$-tetrazol-1-yl | 2-chloro-1,4-phenylene | 2-methoxyphenyl |
|  | 11 | H | $CH_2$-tetrazol-2-yl | 2-chloro-1,4-phenylene | 2-methoxyphenyl |
|  | 12 | H | $CH_2$-triazol-1-yl | 2-chloro-1,4-phenylene | 2-methoxyphenyl |
|  | 13 | H | $CH_2SEt$ | 2-chloro-1,4-phenylene | 2-methoxyphenyl |
|  | 14 | H | $CH_2SO_2Et$ | 2-chloro-1,4-phenylene | 2-methoxyphenyl |
|  | 15 | H | $CF_3$ | 2-chloro-1,4-phenylene | 2-methoxyphenyl |
|  | 16 | H | $CH_3$ | 2-chloro-1,4-phenylene | 2-methoxyphenyl |
|  | 17 | H | H | 2-chloro-1,4-phenylene | 2-methoxyphenyl |
| G6 | 1 | H | $CH_2OMe$ | 2-methyl-1,4-phenylene | 2-methoxyphenyl |
|  | 2 | H | $CH_2OEt$ | 2-methyl-1,4-phenylene | 2-methoxyphenyl |
|  | 3 | H | $CH_2O$-n-Pr | 2-methyl-1,4-phenylene | 2-methoxyphenyl |
|  | 4 | H | $CH_2O$-i-Pr | 2-methyl-1,4-phenylene | 2-methoxyphenyl |
|  | 5 | H | $CH_2O$-n-Bu | 2-methyl-1,4-phenylene | 2-methoxyphenyl |
|  | 6 | H | $CH_2O$-i-Bu | 2-methyl-1,4-phenylene | 2-methoxyphenyl |
|  | 7 | H | $CH_2Ph$ | 2-methyl-1,4-phenylene | 2-methoxyphenyl |
|  | 8 | H | $CH_2$-pyrazol-1-yl | 2-methyl-1,4-phenylene | 2-methoxyphenyl |
|  | 9 | H | $CH_2$-imidazol-1-yl | 2-methyl-1,4-phenylene | 2-methoxyphenyl |
|  | 10 | H | $CH_2$-tetrazol-1-yl | 2-methyl-1,4-phenylene | 2-methoxyphenyl |
|  | 11 | H | $CH_2$-tetrazol-2-yl | 2-methyl-1,4-phenylene | 2-methoxyphenyl |
|  | 12 | H | $CH_2$-triazol-1-yl | 2-methyl-1,4-phenylene | 2-methoxyphenyl |
|  | 13 | H | $CH_2SEt$ | 2-methyl-1,4-phenylene | 2-methoxyphenyl |
|  | 14 | H | $CH_2SO_2Et$ | 2-methyl-1,4-phenylene | 2-methoxyphenyl |
|  | 15 | H | $CF_3$ | 2-methyl-1,4-phenylene | 2-methoxyphenyl |
|  | 16 | H | $CH_3$ | 2-methyl-1,4-phenylene | 2-methoxyphenyl |
|  | 17 | H | H | 2-methyl-1,4-phenylene | 2-methoxyphenyl |
| H1 | 1 | H | $CH_2OMe$ | phenyl | 2-methysulfonylphenyl |

TABLE 7-continued a

![Structure a: 3-(3-amidinophenyl)-isoxazoline with R, (CH2)nR2 substituents and carboxamide linker to N-V-(Z)u-D]

b

![Structure b: isomeric isoxazoline with R and (CH2)nR2 on opposite ring positions]

| Part | Cpd | R | (CH$_2$)$_2$R$^2$ | V | (Z)$_u$—D |
|------|-----|---|-------------------|---|-----------|
|  | 2 | H | CH$_2$OEt | phenyl | 2-methysulfonylphenyl |
|  | 3 | H | CH$_2$O-n-Pr | phenyl | 2-methysulfonylphenyl |
|  | 4 | H | CH$_2$O-i-Pr | phenyl | 2-methysulfonylphenyl |
|  | 5 | H | CH$_2$O-n-Bu | phenyl | 2-methysulfonylphenyl |
|  | 6 | H | CH$_2$O-i-Bu | phenyl | 2-methysulfonylphenyl |
|  | 7 | H | CH$_2$Ph | phenyl | 2-methysulfonylphenyl |
|  | 8 | H | CH$_2$-pyrazol-1-yl | phenyl | 2-methysulfonylphenyl |
|  | 9 | H | CH$_2$-imidazol-1-yl | phenyl | 2-methysulfonylphenyl |
|  | 10 | H | CH$_2$-tetrazol-1-yl | phenyl | 2-methysulfonylphenyl |
|  | 11 | H | CH$_2$-tetrazol-2-yl | phenyl | 2-methysulfonylphenyl |
|  | 12 | H | CH$_2$-triazol-1-yl | phenyl | 2-methysulfonylphenyl |
|  | 13 | H | CH$_2$SEt | phenyl | 2-methysulfonylphenyl |
|  | 14 | H | CH$_2$SO$_2$Et | phenyl | 2-methysulfonylphenyl |
|  | 15 | H | CF$_3$ | phenyl | 2-methysulfonylphenyl |
|  | 16 | H | CH$_3$ | phenyl | 2-methysulfonylphenyl |
|  | 17 | H | H | phenyl | 2-methysulfonylphenyl |
| H2 | 1 | H | CH$_2$OMe | pyridin-2,5-diyl | 2-methysulfonylphenyl |
|  | 2 | H | CH$_2$OEt | pyridin-2,5-diyl | 2-methysulfonylphenyl |
|  | 3 | H | CH$_2$O-n-Pr | pyridin-2,5-diyl | 2-methysulfonylphenyl |
|  | 4 | H | CH$_2$O-i-Pr | pyridin-2,5-diyl | 2-methysulfonylphenyl |
|  | 5 | H | CH$_2$O-n-Bu | pyridin-2,5-diyl | 2-methysulfonylphenyl |
|  | 6 | H | CH$_2$O-i-Bu | pyridin-2,5-diyl | 2-methysulfonylphenyl |
|  | 7 | H | CH$_2$Ph | pyridin-2,5-diyl | 2-methysulfonylphenyl |
|  | 8 | H | CH$_2$-pyrazol-1-yl | pyridin-2,5-diyl | 2-methysulfonylphenyl |
|  | 9 | H | CH$_2$-imidazol-1-yl | pyridin-2,5-diyl | 2-methysulfonylphenyl |
|  | 10 | H | CH$_2$-tetrazol-1-yl | pyridin-2,5-diyl | 2-methysulfonylphenyl |
|  | 11 | H | CH$_2$-tetrazol-2-yl | pyridin-2,5-diyl | 2-methysulfonylphenyl |
|  | 12 | H | CH$_2$-triazol-1-yl | pyridin-2,5-diyl | 2-methysulfonylphenyl |
|  | 13 | H | CH$_2$SEt | pyridin-2,5-diyl | 2-methysulfonylphenyl |
|  | 14 | H | CH$_2$SO$_2$Et | pyridin-2,5-diyl | 2-methysulfonylphenyl |
|  | 15 | H | CF$_3$ | pyridin-2,5-diyl | 2-methysulfonylphenyl |
|  | 16 | H | CH$_3$ | pyridin-2,5-diyl | 2-methysulfonylphenyl |
|  | 17 | H | H | pyridin-2,5-diyl | 2-methysulfonylphenyl |
| H3 | 1 | H | CH$_2$OMe | pyrimidin-2,5-diyl | 2-methysulfonylphenyl |
|  | 2 | H | CH$_2$OEt | pyrimidin-2,5-diyl | 2-methysulfonylphenyl |
|  | 3 | H | CH$_2$O-n-Pr | pyrimidin-2,5-diyl | 2-methysulfonylphenyl |
|  | 4 | H | CH$_2$O-i-Pr | pyrimidin-2,5-diyl | 2-methysulfonylphenyl |
|  | 5 | H | CH$_2$O-n-Bu | pyrimidin-2,5-diyl | 2-methysulfonylphenyl |
|  | 6 | H | CH$_2$O-i-Bu | pyrimidin-2,5-diyl | 2-methysulfonylphenyl |
|  | 7 | H | CH$_2$Ph | pyrimidin-2,5-diyl | 2-methysulfonylphenyl |
|  | 8 | H | CH$_2$-pyrazol-1-yl | pyrimidin-2,5-diyl | 2-methysulfonylphenyl |
|  | 9 | H | CH$_2$-imidazol-1-yl | pyrimidin-2,5-diyl | 2-methysulfonylphenyl |
|  | 10 | H | CH$_2$-tetrazol-1-yl | pyrimidin-2,5-diyl | 2-methysulfonylphenyl |
|  | 11 | H | CH$_2$-tetrazol-2-yl | pyrimidin-2,5-diyl | 2-methysulfonylphenyl |
|  | 12 | H | CH$_2$-triazol-1-yl | pyrimidin-2,5-diyl | 2-methysulfonylphenyl |
|  | 13 | H | CH$_2$SEt | pyrimidin-2,5-diyl | 2-methysulfonylphenyl |
|  | 14 | H | CH$_2$SO$_2$Et | pyrimidin-2,5-diyl | 2-methysulfonylphenyl |
|  | 15 | H | CF$_3$ | pyrimidin-2,5-diyl | 2-methysulfonylphenyl |
|  | 16 | H | CH$_3$ | pyrimidin-2,5-diyl | 2-methysulfonylphenyl |
|  | 17 | H | H | pyrimidin-2,5-diyl | 2-methysulfonylphenyl |
| H4 | 1 | H | CH$_2$OMe | 2-fluoro-1,4-phenylene | 2-methylsulfonylphenyl |

TABLE 7-continued a

[Structure a: 3-(3-amidinophenyl)-isoxazoline with R at 4-position, (CH₂)ₙR² at 5-position, and carboxamide-NH-V-(Z)ᵤ-D]

b

[Structure b: 3-(3-amidinophenyl)-isoxazoline with R and carboxamide at 4-position, (CH₂)ₙR² at 5-position]

| Part | Cpd | R | (CH₂)₂R² | V | (Z)ᵤ—D |
|------|-----|---|----------|---|--------|
|    | 2  | H | CH₂OEt            | 2-fluoro-1,4-phenylene | 2-methylsulfonylphenyl |
|    | 3  | H | CH₂O-n-Pr         | 2-fluoro-1,4-phenylene | 2-methylsulfonylphenyl |
|    | 4  | H | CH₂O-i-Pr         | 2-fluoro-1,4-phenylene | 2-methylsulfonylphenyl |
|    | 5  | H | CH₂O-n-Bu         | 2-fluoro-1,4-phenylene | 2-methylsulfonylphenyl |
|    | 6  | H | CH₂O-i-Bu         | 2-fluoro-1,4-phenylene | 2-methylsulfonylphenyl |
|    | 7  | H | CH₂Ph             | 2-fluoro-1,4-phenylene | 2-methylsulfonylphenyl |
|    | 8  | H | CH₂-pyrazol-1-yl  | 2-fluoro-1,4-phenylene | 2-methylsulfonylphenyl |
|    | 9  | H | CH₂-imidazol-1-yl | 2-fluoro-1,4-phenylene | 2-methylsulfonylphenyl |
|    | 10 | H | CH₂-tetrazol-1-yl | 2-fluoro-1,4-phenylene | 2-methylsulfonylphenyl |
|    | 11 | H | CH₂-tetrazol-2-yl | 2-fluoro-1,4-phenylene | 2-methylsulfonylphenyl |
|    | 12 | H | CH₂triazol-1-yl   | 2-fluoro-1,4-phenylene | 2-methylsulfonylphenyl |
|    | 13 | H | CH₂SEt            | 2-fluoro-1,4-phenylene | 2-methylsulfonylphenyl |
|    | 14 | H | CH₂SO₂Et          | 2-fluoro-1,4-phenylene | 2-methylsulfonylphenyl |
|    | 15 | H | CF₃               | 2-fluoro-1,4-phenylene | 2-methylsulfonylphenyl |
|    | 16 | H | CH₃               | 2-fluoro-1,4-phenylene | 2-methylsulfonylphenyl |
|    | 17 | H | H                 | 2-fluoro-1,4-phenylene | 2-methylsulfonylphenyl |
| H5 | 1  | H | CH₂OMe            | 2-chloro-1,4-phenylene | 2-methylsulfonylphenyl |
|    | 2  | H | CH₂OEt            | 2-chloro-1,4-phenylene | 2-methylsulfonylphenyl |
|    | 3  | H | CH₂O-n-Pr         | 2-chloro-1,4-phenylene | 2-methylsulfonylphenyl |
|    | 4  | H | CH₂O-i-Pr         | 2-chloro-1,4-phenylene | 2-methylsulfonylphenyl |
|    | 5  | H | CH₂O-n-Bu         | 2-chloro-1,4-phenylene | 2-methylsulfonylphenyl |
|    | 6  | H | CH₂O-i-Bu         | 2-chloro-1,4-phenylene | 2-methylsulfonylphenyl |
|    | 7  | H | CH₂Ph             | 2-chloro-1,4-phenylene | 2-methylsulfonylphenyl |
|    | 8  | H | CH₂-pyrazol-1-yl  | 2-chloro-1,4-phenylene | 2-methylsulfonylphenyl |
|    | 9  | H | CH₂-imidazol-1-yl | 2-chloro-1,4-phenylene | 2-methylsulfonylphenyl |
|    | 10 | H | CH₂-tetrazol-1-yl | 2-chloro-1,4-phenylene | 2-methylsulfonylphenyl |
|    | 11 | H | CH₂-tetrazol-2-yl | 2-chloro-1,4-phenylene | 2-methylsulfonylphenyl |
|    | 12 | H | CH₂-triazol-1-yl  | 2-chloro-1,4-phenylene | 2-methylsulfonylphenyl |
|    | 13 | H | CH₂SEt            | 2-chloro-1,4-phenylene | 2-methylsulfonylphenyl |
|    | 14 | H | CH₂SO₂Et          | 2-chloro-1,4-phenylene | 2-methylsulfonylphenyl |
|    | 15 | H | CF₃               | 2-chloro-1,4-phenylene | 2-methylsulfonylphenyl |
|    | 16 | H | CH₃               | 2-chloro-1,4-phenylene | 2-methylsulfonylphenyl |
|    | 17 | H | H                 | 2-chloro-1,4-phenylene | 2-methylsulfonylphenyl |
| H6 | 1  | H | CH₂OMe            | 2-methyl-1,4-phenylene | 2-methylsulfonylphenyl |
|    | 2  | H | CH₂OEt            | 2-methyl-1,4-phenylene | 2-methylsulfonylphenyl |
|    | 3  | H | CH₂O-n-Pr         | 2-methyl-1,4-phenylene | 2-methylsulfonylphenyl |
|    | 4  | H | CH₂O-i-Pr         | 2-methyl-1,4-phenylene | 2-methylsulfonylphenyl |
|    | 5  | H | CH₂O-n-Bu         | 2-methyl-1,4-phenylene | 2-methylsulfonylphenyl |
|    | 6  | H | CH₂O-i-Bu         | 2-methyl-1,4-phenylene | 2-methylsulfonylphenyl |
|    | 7  | H | CH₂Ph             | 2-methyl-1,4-phenylene | 2-methylsulfonylphenyl |
|    | 8  | H | CH₂-pyrazol-1-yl  | 2-methyl-1,4-phenylene | 2-methylsulfonylphenyl |
|    | 9  | H | CH₂-imidazol-1-yl | 2-methyl-1,4-phenylene | 2-methylsulfonylphenyl |
|    | 10 | H | CH₂-tetrazol-1-yl | 2-methyl-1,4-phenylene | 2-methylsulfonylphenyl |
|    | 11 | H | CH₂-tetrazol-2-yl | 2-methyl-1,4-phenylene | 2-methylsulfonylphenyl |
|    | 12 | H | CH₂-triazol-1-yl  | 2-methyl-1,4-phenylene | 2-methylsulfonylphenyl |
|    | 13 | H | CH₂SEt            | 2-methyl-1,4-phenylene | 2-methylsulfonylphenyl |
|    | 14 | H | CH₂SO₂Et          | 2-methyl-1,4-phenylene | 2-methylsulfonylphenyl |
|    | 15 | H | CF₃               | 2-methyl-1,4-phenylene | 2-methylsulfonylphenyl |
|    | 16 | H | CH₃               | 2-methyl-1,4-phenylene | 2-methylsulfonylphenyl |
|    | 17 | H | H                 | 2-methyl-1,4-phenylene | 2-methylsulfonylphenyl |
| I1 | 1  | H | CH₂OMe            | 1,4-phenylene          | 2-nitrophenoxy |

TABLE 7-continued

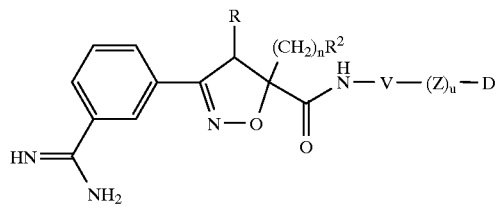

a

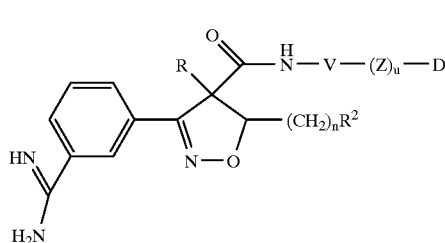

b

| Part | Cpd | R | $(CH_2)_2R^2$ | V | $(Z)_u$—D |
|---|---|---|---|---|---|
| | 2 | H | $CH_2OEt$ | 1,4-phenylene | 2-nitrophenoxy |
| | 3 | H | $CH_2O$-n-Pr | 1,4-phenylene | 2-nitrophenoxy |
| | 4 | H | $CH_2O$-i-Pr | 1,4-phenylene | 2-nitrophenoxy |
| | 5 | H | $CH_2O$-n-Bu | 1,4-phenylene | 2-nitrophenoxy |
| | 6 | H | $CH_2O$-i-Bu | 1,4-phenylene | 2-nitrophenoxy |
| | 7 | H | $CH_2Ph$ | 1,4-phenylene | 2-nitrophenoxy |
| | 8 | H | $CH_2$-pyrazol-1-yl | 1,4-phenylene | 2-nitrophenoxy |
| | 9 | H | $CH_2$-imidazol-1-yl | 1,4-phenylene | 2-nitrophenoxy |
| | 10 | H | $CH_2$-tetrazol-1-yl | 1,4-phenylene | 2-nitrophenoxy |
| | 11 | H | $CH_2$-tetrazol-2-yl | 1,4-phenylene | 2-nitrophenoxy |
| | 12 | H | $CH_2$-triazol-1-yl | 1,4-phenylene | 2-nitrophenoxy |
| | 13 | H | $CH_2SEt$ | 1,4-phenylene | 2-nitrophenoxy |
| | 14 | H | $CH_2SO_2Et$ | 1,4-phenylene | 2-nitrophenoxy |
| | 15 | H | $CF_3$ | 1,4-phenylene | 2-nitrophenoxy |
| | 16 | H | $CH_3$ | 1,4-phenylene | 2-nitrophenoxy |
| | 17 | H | H | 1,4-phenylene | 2-nitrophenoxy |
| J1 | 1 | H | $CH_2OMe$ | 2,5-thiophene | 2-aminosulfonylphenyl |
| | 2 | H | $CH_2OEt$ | 2,5-thiophene | 2-aminosulfonylphenyl |
| | 3 | H | $CH_2O$-n-Pr | 2,5-thiophene | 2-aminosulfonylphenyl |
| | 4 | H | $CH_2O$-i-Pr | 2,5-thiophene | 2-aminosulfonylphenyl |
| | 5 | H | $CH_2O$-n-Bu | 2,5-thiophene | 2-aminosulfonylphenyl |
| | 6 | H | $CH_2O$-i-Bu | 2,5-thiophene | 2-aminosulfonylphenyl |
| | 7 | H | $CH_2Ph$ | 2,5-thiophene | 2-aminosulfonylphenyl |
| | 8 | H | $CH_2$-pyrazol-1-yl | 2,5-thiophene | 2-aminosulfonylphenyl |
| | 9 | H | $CH_2$-imidazol-1-yl | 2,5-thiophene | 2-aminosulfonylphenyl |
| | 10 | H | $CH_2$-tetrazol-1-yl | 2,5-thiophene | 2-aminosulfonylphenyl |
| | 11 | H | $CH_2$-tetrazol-2-yl | 2,5-thiophene | 2-aminosulfonylphenyl |
| | 12 | H | $CH_2$-triazol-1-yl | 2,5-thiophene | 2-aminosulfonylphenyl |
| | 13 | H | $CH_2SEt$ | 2,5-thiophene | 2-aminosulfonylphenyl |
| | 14 | H | $CH_2SO_2Et$ | 2,5-thiophene | 2-aminosulfonylphenyl |
| | 15 | H | $CF_3$ | 2,5-thiophene | 2-aminosulfonylphenyl |
| | 16 | H | $CH_3$ | 2,5-thiophene | 2-aminosulfonylphenyl |
| | 17 | H | H | 2,5-thiophene | 2-aminosulfonylphenyl |

TABLE 8

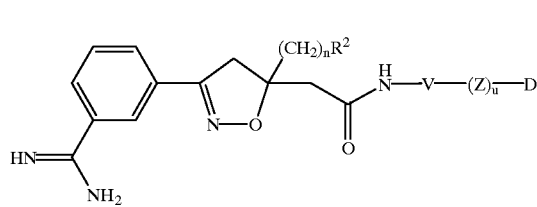
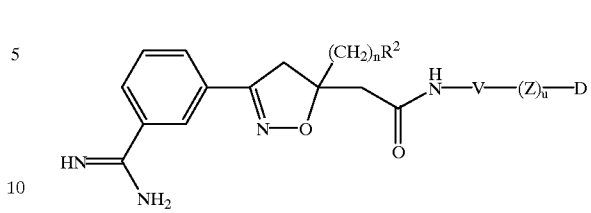

| Part | Cpd | (CH$_2$)$_n$R$^2$ | V | (Z)$_u$—D |
|---|---|---|---|---|
| A | 1 | CH$_2$OMe | phenyl | 2-aminosulfonylphenyl |
|   | 2 | CH$_2$OEt | phenyl | 2-aminosulfonylphenyl |
|   | 3 | CH$_2$O-n-Pr | phenyl | 2-aminosulfonylphenyl |
|   | 4 | CH$_2$O-i-Pr | phenyl | 2-aminosulfonylphenyl |
|   | 5 | CH$_2$O-n-Bu | phenyl | 2-aminosulfonylphenyl |
|   | 6 | CH$_2$O-i-Bu | phenyl | 2-aminosulfonylphenyl |
|   | 7 | CH$_2$Ph | phenyl | 2-aminosulfonylphenyl |
|   | 8 | CH$_2$-pyrazol-1-yl | phenyl | 2-aminosulfonylphenyl |
|   | 9 | CH$_2$-imidazol-1-yl | phenyl | 2-aminosulfonylphenyl |
|   | 10 | CH$_2$-tetrazol-1-yl | phenyl | 2-aminosulfonylphenyl |
|   | 11 | CH$_2$-tetrazol-2-yl | phenyl | 2-aminosulfonylphenyl |
|   | 12 | CH$_2$-triazol-1-yl | phenyl | 2-aminosulfonylphenyl |
|   | 13 | CH$_2$SEt | phenyl | 2-aminosulfonylphenyl |
|   | 14 | CH$_2$SO$_2$Et | phenyl | 2-aminosulfonylphenyl |
|   | 15 | CF$_3$ | phenyl | 2-aminosulfonylphenyl |
|   | 16 | CH$_3$ | phenyl | 2-aminosulfonylphenyl |
|   | 17 | H | phenyl | 2-aminosulfonylphenyl |
| B | 1 | CH$_2$OMe | pyridin-2,5-diyl | 2-aminosulfonylphenyl |
|   | 2 | CH$_2$OEt | pyridin-2,5-diyl | 2-aminosulfonylphenyl |
|   | 3 | CH$_2$O-n-Pr | pyridin-2,5-diyl | 2-aminosulfonylphenyl |
|   | 4 | CH$_2$O-i-Pr | pyridin-2,5-diyl | 2-aminosulfonylphenyl |
|   | 5 | CH$_2$O-n-Bu | pyridin-2,5-diyl | 2-aminosulfonylphenyl |
|   | 6 | CH$_2$O-i-Bu | pyridin-2,5-diyl | 2-aminosulfonylphenyl |
|   | 7 | CH$_2$Ph | pyridin-2,5-diyl | 2-aminosulfonylphenyl |
|   | 8 | CH$_2$-pyrazol-1-yl | pyridin-2,5-diyl | 2-aminosulfonylphenyl |
|   | 9 | CH$_2$-imidazol-1-yl | pyridin-2,5-diyl | 2-aminosulfonylphenyl |
|   | 10 | CH$_2$-tetrazol-1-yl | pyridin-2,5-diyl | 2-aminosulfonylphenyl |
|   | 11 | CH$_2$-tetrazol-2-yl | pyridin-2,5-diyl | 2-aminosulfonylphenyl |
|   | 12 | CH$_2$-triazol-1-yl | pyridin-2,5-diyl | 2-aminosulfonylphenyl |
|   | 13 | CH$_2$SEt | pyridin-2,5-diyl | 2-aminosulfonylphenyl |
|   | 14 | CH$_2$SO$_2$Et | pyridin-2,5-diyl | 2-aminosulfonylphenyl |
|   | 15 | CF$_3$ | pyridin-2,5-diyl | 2-aminosulfonylphenyl |
|   | 16 | CH$_3$ | pyridin-2,5-diyl | 2-aminosulfonylphenyl |
|   | 17 | H | pyridin-2,5-diyl | 2-aminosulfonylphenyl |
| C | 1 | CH$_2$OMe | pyrimidin-2,5-diyl | 2-aminosulfonylphenyl |
|   | 2 | CH$_2$OEt | pyrimidin-2,5-diyl | 2-aminosulfonylphenyl |
|   | 3 | CH$_2$O-n-Pr | pyrimidin-2,5-diyl | 2-aminosulfonylphenyl |
|   | 4 | CH$_2$O-i-Pr | pyrimidin-2,5-diyl | 2-aminosulfonylphenyl |
|   | 5 | CH$_2$O-n-Bu | pyrimidin-2,5-diyl | 2-aminosulfonylphenyl |
|   | 6 | CH$_2$O-i-Bu | pyrimidin-2,5-diyl | 2-aminosulfonylphenyl |
|   | 7 | CH$_2$Ph | pyrimidin-2,5-diyl | 2-aminosulfonylphenyl |
|   | 8 | CH$_2$-pyrazol-1-yl | pyrimidin-2,5-diyl | 2-aminosulfonylphenyl |
|   | 9 | CH$_2$-imidazol-1-yl | pyrimidin-2,5-diyl | 2-aminosulfonylphenyl |
|   | 10 | CH$_2$-tetrazol-1-yl | pyrimidin-2,5-diyl | 2-aminosulfonylphenyl |
|   | 11 | CH$_2$-tetrazol-2-yl | pyrimidin-2,5-diyl | 2-aminosulfonylphenyl |
|   | 12 | CH$_2$-triazol-1-yl | pyrimidin-2,5-diyl | 2-aminosulfonylphenyl |
|   | 13 | CH$_2$SEt | pyrimidin-2,5-diyl | 2-aminosulfonylphenyl |
|   | 14 | CH$_2$SO$_2$Et | pyrimidin-2,5-diyl | 2-aminosulfonylphenyl |
|   | 15 | CF$_3$ | pyrimidin-2,5-diyl | 2-aminosulfonylphenyl |
|   | 16 | CH$_3$ | pyrimidin-2,5-diyl | 2-aminosulfonylphenyl |
|   | 17 | H | pyrimidin-2,5-diyl | 2-aminosulfonylphenyl |

TABLE 9

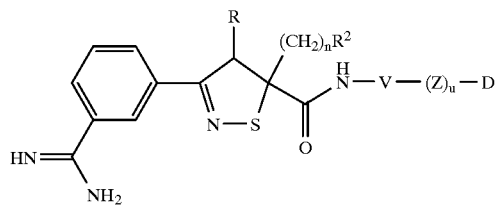

a

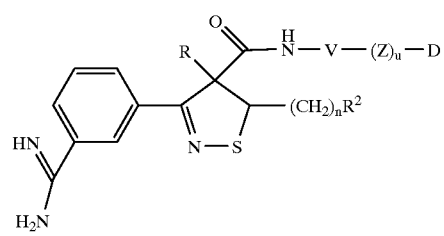

b

| Part | Cpd | R | (CH₂)ₙR² | V | (Z)ᵤ—D |
|---|---|---|---|---|---|
| A | 1 | $CH_3$ | $CH_2OMe$ | phenyl | 2-aminosulfonylphenyl |
|  | 2 | $CH_3$ | $CH_2OEt$ | phenyl | 2-aminosulfonylphenyl |
|  | 3 | $CH_3$ | $CH_2O$-n-Pr | phenyl | 2-aminosulfonylphenyl |
|  | 4 | $CH_3$ | $CH_2O$-i-Pr | phenyl | 2-aminosulfonylphenyl |
|  | 5 | $CH_3$ | $CH_2O$-n-Bu | phenyl | 2-aminosulfonylphenyl |
|  | 6 | $CH_3$ | $CH_2O$-i-Bu | phenyl | 2-aminosulfonylphenyl |
|  | 7 | $CH_3$ | $CH_2Ph$ | phenyl | 2-aminosulfonylphenyl |
|  | 8 | $CH_3$ | $CH_2$-pyrazol-1-yl | phenyl | 2-aminosulfonylphenyl |
|  | 9 | $CH_3$ | $CH_2$-imidazol-1-yl | phenyl | 2-aminosulfonylphenyl |
|  | 10 | $CH_3$ | $CH_2$-tetrazol-1-yl | phenyl | 2-aminosulfonylphenyl |
|  | 11 | $CH_3$ | $CH_2$-tetrazol-2-yl | phenyl | 2-aminosulfonylphenyl |
|  | 12 | $CH_3$ | $CH_2$-triazol-1-yl | phenyl | 2-aminosulfonylphenyl |
|  | 13 | $CH_3$ | $CH_2SEt$ | phenyl | 2-aminosulfonylphenyl |
|  | 14 | $CH_3$ | $CH_2SO_2Et$ | phenyl | 2-aminosulfonylphenyl |
|  | 15 | $CH_3$ | $CF_3$ | phenyl | 2-aminosulfonylphenyl |
|  | 16 | $CH_3$ | $CH_3$ | phenyl | 2-aminosulfonylphenyl |
|  | 17 | $CH_3$ | H | phenyl | 2-aminosulfonylphenyl |
| B | 1 | H | $CH_2OMe$ | phenyl | 2-aminosulfonylphenyl |
|  | 2 | H | $CH_2OEt$ | phenyl | 2-aminosulfonylphenyl |
|  | 3 | H | $CH_2O$-n-Pr | phenyl | 2-aminosulfonylphenyl |
|  | 4 | H | $CH_2O$-i-Pr | phenyl | 2-aminosulfonylphenyl |
|  | 5 | H | $CH_2O$-n-Bu | phenyl | 2-aminosulfonylphenyl |
|  | 6 | H | $CH_2O$-i-Bu | phenyl | 2-aminosulfonylphenyl |
|  | 7 | H | $CH_2Ph$ | phenyl | 2-aminosulfonylphenyl |
|  | 8 | H | $CH_2$-pyrazol-1-yl | phenyl | 2-aminosulfonylphenyl |
|  | 9 | H | $CH_2$-imidazol-1-yl | phenyl | 2-aminosulfonylphenyl |
|  | 10 | H | $CH_2$-tetrazol-1-yl | phenyl | 2-aminosulfonylphenyl |
|  | 11 | H | $CH_2$-tetrazol-2-yl | phenyl | 2-aminosulfonylphenyl |
|  | 12 | H | $CH_2$-triazol-1-yl | phenyl | 2-aminosulfonylphenyl |
|  | 13 | H | $CH_2SEt$ | phenyl | 2-aminosulfonylphenyl |
|  | 14 | H | $CH_2SO_2Et$ | phenyl | 2-aminosulfonylphenyl |
|  | 15 | H | $CF_3$ | phenyl | 2-aminosulfonylphenyl |
|  | 16 | H | $CH_3$ | phenyl | 2-aminosulfonylphenyl |
|  | 17 | H | H | phenyl | 2-aminosulfonylphenyl |

TABLE 10

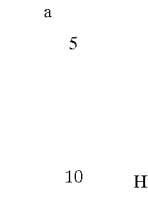

a

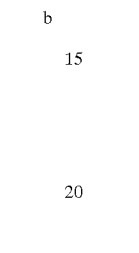

b

| Cpd | R¹⁵ | (CH₂)ₙR² | V | (Z)ᵤ—D |
|---|---|---|---|---|
| 1 | $CH_3$ | $CH_2OMe$ | 1,4-phenylene | 2-aminosulfonylphenyl |
| 2 | $CH_3$ | $CH_2OEt$ | 1,4-phenylene | 2-aminosulfonylphenyl |
| 3 | $CH_3$ | $CH_2O$-n-Pr | 1,4-phenylene | 2-aminosulfonylphenyl |
| 4 | $CH_3$ | $CH_2O$-i-Pr | 1,4-phenylene | 2-aminosulfonylphenyl |
| 5 | $CH_3$ | $CH_2O$-n-Bu | 1,4-phenylene | 2-aminosulfonylphenyl |
| 6 | $CH_3$ | $CH_2O$-i-Bu | 1,4-phenylene | 2-aminosulfonylphenyl |
| 7 | $CH_3$ | $CH_2Ph$ | 1,4-phenylene | 2-aminosulfonylphenyl |
| 8 | $CH_3$ | $CH_2$-pyrazol-1-yl | 1,4-phenylene | 2-aminosulfonylphenyl |
| 9 | $CH_3$ | $CH_2$-imidazol-1-yl | 1,4-phenylene | 2-aminosulfonylphenyl |
| 10 | $CH_3$ | $CH_2$-tetrazol-1-yl | 1,4-phenylene | 2-aminosulfonylphenyl |
| 11 | $CH_3$ | $CH_2$-tetrazol-2-yl | 1,4-phenylene | 2-aminosulfonylphenyl |
| 12 | $CH_3$ | $CH_2$-triazol-1-yl | 1,4-phenylene | 2-aminosulfonylphenyl |
| 13 | $CH_3$ | $CH_2SEt$ | 1,4-phenylene | 2-aminosulfonylphenyl |
| 14 | $CH_3$ | $CH_2SO_2Et$ | 1,4-phenylene | 2-aminosulfonylphenyl |
| 15 | $CH_3$ | $CF_3$ | 1,4-phenylene | 2-aminosulfonylphenyl |
| 16 | $CH_3$ | $CH_3$ | 1,4-phenylene | 2-aminosulfonylphenyl |
| 17 | $CH_3$ | H | 1,4-phenylene | 2-aminosulfonylphenyl |
| 18 | $CH_2CF_3$ | $CH_2OMe$ | 1,4-phenylene | 2-aminosulfonylphenyl |
| 19 | $CH_2CF_3$ | $CH_2OEt$ | 1,4-phenylene | 2-aminosulfonylphenyl |
| 20 | $CH_2CF_3$ | $CH_2O$-n-Pr | 1,4-phenylene | 2-aminosulfonylphenyl |
| 21 | $CH_2CF_3$ | $CH_2O$-i-Pr | 1,4-phenylene | 2-aminosulfonylphenyl |
| 22 | $CH_2CF_3$ | $CH_2O$-n-Bu | 1,4-phenylene | 2-aminosulfonylphenyl |
| 23 | $CH_2CF_3$ | $CH_2O$-i-Bu | 1,4-phenylene | 2-aminosulfonylphenyl |
| 24 | $CH_2CF_3$ | $CH_2Ph$ | 1,4-phenylene | 2-aminosulfonylphenyl |
| 25 | $CH_2CF_3$ | $CH_2$-pyrazol-1-yl | 1,4-phenylene | 2-aminosulfonylphenyl |
| 26 | $CH_2CF_3$ | $CH_2$-imidazol-1-yl | 1,4-phenylene | 2-aminosulfonylphenyl |
| 27 | $CH_2CF_3$ | $CH_2$-tetrazol-1-yl | 1,4-phenylene | 2-aminosulfonylphenyl |
| 28 | $CH_2CF_3$ | $CH_2$-tetrazol-2-yl | 1,4-phenylene | 2-aminosulfonylphenyl |
| 29 | $CH_2CF_3$ | $CH_2$-triazol-1-yl | 1,4-phenylene | 2-aminosulfonylphenyl |
| 30 | $CH_2CF_3$ | $CH_2SEt$ | 1,4-phenylene | 2-aminosulfonylphenyl |
| 31 | $CH_2CF_3$ | $CH_2SO_2Et$ | 1,4-phenylene | 2-aminosulfonylphenyl |
| 32 | $CH_2CF_3$ | $CF_3$ | 1,4-phenylene | 2-aminosulfonylphenyl |
| 33 | $CH_2CF_3$ | $CH_3$ | 1,4-phenylene | 2-aminosulfonylphenyl |
| 34 | $CH_2CF_3$ | H | 1,4-phenylene | 2-aminosulfonylphenyl |

TABLE 11

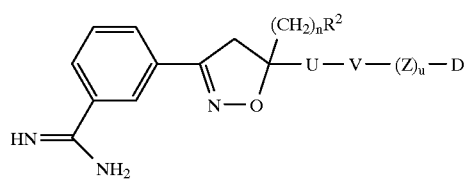

a

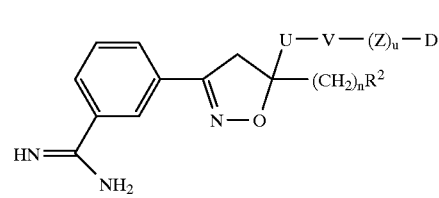

b

| Part | Cpd | U | $(CH_2)_nR^2$ | V | $(Z)_u$-D |
|---|---|---|---|---|---|
| A | 1 | $CH_2NH$ | $CH_2OMe$ | 1,4-phenylene | 2-aminosulfonylphenyl |
|  | 2 | $CH_2NH$ | $CH_2OEt$ | 1,4-phenylene | 2-aminosulfonylphenyl |
|  | 3 | $CH_2NH$ | $CH_2O$-n-Pr | 1,4-phenylene | 2-aminosulfonylphenyl |
|  | 4 | $CH_2NH$ | $CH_2O$-i-Pr | 1,4-phenylene | 2-aminosulfonylphenyl |
|  | 5 | $CH_2NH$ | $CH_2O$-n-Bu | 1,4-phenylene | 2-aminosulfonylphenyl |
|  | 6 | $CH_2NH$ | $CH_2O$-i-Bu | 1,4-phenylene | 2-aminosulfonylphenyl |
|  | 7 | $CH_2NH$ | $CH_2Ph$ | 1,4-phenylene | 2-aminosulfonylphenyl |
|  | 8 | $CH_2NH$ | $CH_2$-pyrazol-1-yl | 1,4-phenylene | 2-aminosulfonylphenyl |
|  | 9 | $CH_2NH$ | $CH_2$-imidazol-1-yl | 1,4-phenylene | 2-aminosulfonylphenyl |
|  | 10 | $CH_2NH$ | $CH_2$tetrazol-1-yl | 1,4-phenylene | 2-aminosulfonylphenyl |
|  | 11 | $CH_2NH$ | $CH_2$tetrazol-2-yl | 1,4-phenylene | 2-aminosulfonylphenyl |
|  | 12 | $CH_2NH$ | $CH_2$-triazol-1-yl | 1,4-phenylene | 2-aminosulfonylphenyl |
|  | 13 | $CH_2NH$ | $CH_2SEt$ | 1,4-phenylene | 2-aminosulfonylphenyl |
|  | 14 | $CH_2NH$ | $CH_2SO_2Et$ | 1,4-phenylene | 2-aminosulfonylphenyl |
|  | 15 | $CH_2NH$ | $CF_3$ | 1,4-phenylene | 2-aminosulfonylphenyl |
|  | 16 | $CH_2NH$ | $CH_3$ | 1,4-phenylene | 2-aminosulfonylphenyl |
|  | 17 | $CH_2NH$ | H | 1,4-phenylene | 2-aminosulfonylphenyl |
| B | 1 | $CH_2CO$ | $CH_2OMe$ | 1,4-phenylene | 2-aminosulfonylphenyl |
|  | 2 | $CH_2CO$ | $CH_2OEt$ | 1,4-phenylene | 2-aminosulfonylphenyl |
|  | 3 | $CH_2CO$ | $CH_2O$-n-Pr | 1,4-phenylene | 2-aminosulfonylphenyl |
|  | 4 | $CH_2CO$ | $CH_2O$-i-Pr | 1,4-phenylene | 2-aminosulfonylphenyl |
|  | 5 | $CH_2CO$ | $CH_2O$-n-Bu | 1,4-phenylene | 2-aminosulfonylphenyl |
|  | 6 | $CH_2CO$ | $CH_2O$-i-Bu | 1,4-phenylene | 2-aminosulfonylphenyl |
|  | 7 | $CH_2CO$ | $CH_2Ph$ | 1,4-phenylene | 2-aminosulfonylphenyl |
|  | 8 | $CH_2CO$ | $CH_2$-pyrazol-1-yl | 1,4-phenylene | 2-aminosulfonylphenyl |
|  | 9 | $CH_2CO$ | $CH_2$-imidazol-1-yl | 1,4-phenylene | 2-aminosulfonylphenyl |
|  | 10 | $CH_2CO$ | $CH_2$tetrazol-1-yl | 1,4-phenylene | 2-aminosulfonylphenyl |
|  | 11 | $CH_2CO$ | $CH_2$tetrazol-2-yl | 1,4-phenylene | 2-aminosulfonylphenyl |
|  | 12 | $CH_2CO$ | $CH_2$-triazol-1-yl | 1,4-phenylene | 2-aminosulfonylphenyl |
|  | 13 | $CH_2CO$ | $CH_2SEt$ | 1,4-phenylene | 2-aminosulfonylphenyl |
|  | 14 | $CH_2CO$ | $CH_2SO_2Et$ | 1,4-phenylene | 2-aminosulfonylphenyl |
|  | 15 | $CH_2CO$ | $CF_3$ | 1,4-phenylene | 2-aminosulfonylphenyl |
|  | 16 | $CH_2CO$ | $CH_3$ | 1,4-phenylene | 2-aminosulfonylphenyl |
|  | 17 | $CH_2CO$ | H | 1,4-phenylene | 2-aminosulfonylphenyl |
| C | 1 | $CH_2CH_2$ | $CH_2OMe$ | 1,4-phenylene | 2-aminosulfonylphenyl |
|  | 2 | $CH_2CH_2$ | $CH_2OEt$ | 1,4-phenylene | 2-aminosulfonylphenyl |
|  | 3 | $CH_2CH_2$ | $CH_2O$-n-Pr | 1,4-phenylene | 2-aminosulfonylphenyl |
|  | 4 | $CH_2CH_2$ | $CH_2O$-i-Pr | 1,4-phenylene | 2-aminosulfonylphenyl |
|  | 5 | $CH_2CH_2$ | $CH_2O$-n-Bu | 1,4-phenylene | 2-aminosulfonylphenyl |
|  | 6 | $CH_2CH_2$ | $CH_2O$-i-Bu | 1,4-phenylene | 2-aminosulfonylphenyl |
|  | 7 | $CH_2CH_2$ | $CH_2Ph$ | 1,4-phenylene | 2-aminosulfonylphenyl |
|  | 8 | $CH_2CH_2$ | $CH_2$-pyrazol-1-yl | 1,4-phenylene | 2-aminosulfonylphenyl |
|  | 9 | $CH_2CH_2$ | $CH_2$-imidazol-1-yl | 1,4-phenylene | 2-aminosulfonylphenyl |
|  | 10 | $CH_2CH_2$ | $CH_2$tetrazol-1-yl | 1,4-phenylene | 2-aminosulfonylphenyl |
|  | 11 | $CH_2CH_2$ | $CH_2$tetrazol-2-yl | 1,4-phenylene | 2-aminosulfonylphenyl |
|  | 12 | $CH_2CH_2$ | $CH_2$-triazol-1-yl | 1,4-phenylene | 2-aminosulfonylphenyl |
|  | 13 | $CH_2CH_2$ | $CH_2SEt$ | 1,4-phenylene | 2-aminosulfonylphenyl |
|  | 14 | $CH_2CH_2$ | $CH_2SO_2Et$ | 1,4-phenylene | 2-aminosulfonylphenyl |
|  | 15 | $CH_2CH_2$ | $CF_3$ | 1,4-phenylene | 2-aminosulfonylphenyl |
|  | 16 | $CH_2CH_2$ | $CH_3$ | 1,4-phenylene | 2-aminosulfonylphenyl |
|  | 17 | $CH_2CH_2$ | H | 1,4-phenylene | 2-aminosulfonylphenyl |
| D | 1 | $SO_2NH$ | $CH_2OMe$ | 1,4-phenylene | 2-aminosulfonylphenyl |
|  | 2 | $SO_2NH$ | $CH_2OEt$ | 1,4-phenylene | 2-aminosulfonylphenyl |
|  | 3 | $SO_2NH$ | $CH_2O$-n-Pr | 1,4-phenylene | 2-aminosulfonylphenyl |
|  | 4 | $SO_2NH$ | $CH_2O$-i-Pr | 1,4-phenylene | 2-aminosulfonylphenyl |

TABLE 11-continued a b

| Part | Cpd | U | $(CH_2)_nR^2$ | V | $(Z)_u$-D |
|---|---|---|---|---|---|
| | 5 | $SO_2NH$ | $CH_2$O-n-Bu | 1,4-phenylene | 2-aminosulfonylphenyl |
| | 6 | $SO_2NH$ | $CH_2$O-i-Bu | 1,4-phenylene | 2-aminosulfonylphenyl |
| | 7 | $SO_2NH$ | $CH_2$Ph | 1,4-phenylene | 2-aminosulfonylphenyl |
| | 8 | $SO_2NH$ | $CH_2$-pyrazol-1-yl | 1,4-phenylene | 2-aminosulfonylphenyl |
| | 9 | $SO_2NH$ | $CH_2$-imidazol-1-yl | 1,4-phenylene | 2-aminosulfonylphenyl |
| | 10 | $SO_2NH$ | $CH_2$tetrazol-1-yl | 1,4-phenylene | 2-aminosulfonylphenyl |
| | 11 | $SO_2NH$ | $CH_2$tetrazol-2-yl | 1,4-phenylene | 2-aminosulfonylphenyl |
| | 12 | $SO_2NH$ | $CH_2$-triazol-1-yl | 1,4-phenylene | 2-aminosulfonylphenyl |
| | 13 | $SO_2NH$ | $CH_2$SEt | 1,4-phenylene | 2-aminosulfonylphenyl |
| | 14 | $SO_2NH$ | $CH_2SO_2$Et | 1,4-phenylene | 2-aminosulfonylphenyl |
| | 15 | $SO_2NH$ | $CF_3$ | 1,4-phenylene | 2-aminosulfonylphenyl |
| | 16 | $SO_2NH$ | $CH_3$ | 1,4-phenylene | 2-aminosulfonylphenyl |
| | 17 | $SO_2NH$ | H | 1,4-phenylene | 2-aminosulfonylphenyl |
| E | 1 | $SO_2CH_2$ | $CH_2$OMe | 1,4-phenylene | 2-aminosulfonylphenyl |
| | 2 | $SO_2CH_2$ | $CH_2$OEt | 1,4-phenylene | 2-aminosulfonylphenyl |
| | 3 | $SO_2CH_2$ | $CH_2$O-n-Pr | 1,4-phenylene | 2-aminosulfonylphenyl |
| | 4 | $SO_2CH_2$ | $CH_2$O-i-Pr | 1,4-phenylene | 2-aminosulfonylphenyl |
| | 5 | $SO_2CH_2$ | $CH_2$O-n-Bu | 1,4-phenylene | 2-aminosulfonylphenyl |
| | 6 | $SO_2CH_2$ | $CH_2$O-i-Bu | 1,4-phenylene | 2-aminosulfonylphenyl |
| | 7 | $SO_2CH_2$ | $CH_2$Ph | 1,4-phenylene | 2-aminosulfonylphenyl |
| | 8 | $SO_2CH_2$ | $CH_2$-pyrazol-1-yl | 1,4-phenylene | 2-aminosulfonylphenyl |
| | 9 | $SO_2CH_2$ | $CH_2$-imidazol-1-yl | 1,4-phenylene | 2-aminosulfonylphenyl |
| | 10 | $SO_2CH_2$ | $CH_2$tetrazol-1-yl | 1,4-phenylene | 2-aminosulfonylphenyl |
| | 11 | $SO_2CH_2$ | $CH_2$tetrazol-2-yl | 1,4-phenylene | 2-aminosulfonylphenyl |
| | 12 | $SO_2CH_2$ | $CH_2$-triazol-1-yl | 1,4-phenylene | 2-aminosulfonylphenyl |
| | 13 | $SO_2CH_2$ | $CH_2$SEt | 1,4-phenylene | 2-aminosulfonylphenyl |
| | 14 | $SO_2CH_2$ | $CH_2SO_2$Et | 1,4-phenylene | 2-aminosulfonylphenyl |
| | 15 | $SO_2CH_2$ | $CF_3$ | 1,4-phenylene | 2-aminosulfonylphenyl |
| | 16 | $SO_2CH_2$ | $CH_3$ | 1,4-phenylene | 2-aminosulfonylphenyl |
| | 17 | $SO_2CH_2$ | H | 1,4-phenylene | 2-aminosulfonylphenyl |
| F | 1 | $CH_2O$ | $CH_2$OMe | 1,4-phenylene | 2-aminosulfonylphenyl |
| | 2 | $CH_2O$ | $CH_2$OEt | 1,4-phenylene | 2-aminosulfonylphenyl |
| | 3 | $CH_2O$ | $CH_2$O-n-Pr | 1,4-phenylene | 2-aminosulfonylphenyl |
| | 4 | $CH_2O$ | $CH_2$O-i-Pr | 1,4-phenylene | 2-aminosulfonylphenyl |
| | 5 | $CH_2O$ | $CH_2$O-n-Bu | 1,4-phenylene | 2-aminosulfonylphenyl |
| | 6 | $CH_2O$ | $CH_2$O-i-Bu | 1,4-phenylene | 2-aminosulfonylphenyl |
| | 7 | $CH_2O$ | $CH_2$Ph | 1,4-phenylene | 2-aminosulfonylphenyl |
| | 8 | $CH_2O$ | $CH_2$-pyrazol-1-yl | 1,4-phenylene | 2-aminosulfonylphenyl |
| | 9 | $CH_2O$ | $CH_2$-imidazol-1-yl | 1,4-phenylene | 2-aminosulfonylphenyl |
| | 10 | $CH_2O$ | $CH_2$tetrazol-1-yl | 1,4-phenylene | 2-aminosulfonylphenyl |
| | 11 | $CH_2O$ | $CH_2$tetrazol-2-yl | 1,4-phenylene | 2-aminosulfonylphenyl |
| | 12 | $CH_2O$ | $CH_2$-triazol-1-yl | 1,4-phenylene | 2-aminosulfonylphenyl |
| | 13 | $CH_2O$ | $CH_2$SEt | 1,4-phenylene | 2-aminosulfonylphenyl |
| | 14 | $CH_2O$ | $CH_2SO_2$Et | 1,4-phenylene | 2-aminosulfonylphenyl |
| | 15 | $CH_2O$ | $CF_3$ | 1,4-phenylene | 2-aminosulfonylphenyl |
| | 16 | $CH_2O$ | $CH_3$ | 1,4-phenylene | 2-aminosulfonylphenyl |
| | 17 | $CH_2O$ | H | 1,4-phenylene | 2-aminosulfonylphenyl |

TABLE 12

I-12

[Structure: isoxazoline core with R² on (CH₂)ₙ, (CH₂)ₘ—U—V—Z—D substituent, and phenyl group bearing R¹]

| Cpd. # | R¹ | n | m | R² | -U-V-Z-D |
|---|---|---|---|---|---|
| 1 | CH₃C(=NOH)NH₂ | 1 | 0 | CO₂Me | -C(=O)NH-(4-biphenyl)-2'-SO₂NH₂ |
| 2 | CH₃CH=NH | 1 | 0 | CO₂Me | -C(=O)NH-(4-biphenyl)-2'-SO₂NH₂ |
| 3 | CH₃C(=NOMe)NH₂ | 1 | 0 | CO₂Me | -C(=O)NH-(pyridin-2-yl)-5-(2-SO₂NH₂-phenyl) |
| 4 | CH₃C(=NCO₂Me)NH₂ | 1 | 0 | CO₂Me | -C(=O)NH-(2-Me-4-biphenyl)-2'-SO₂NH₂ |
| 5 | MeNHC(=NH)NH₂ | 1 | 0 | CO₂Me | -C(=O)NH-(pyrimidin-2-yl)-5-(2-SO₂NH₂-phenyl) |
| 6 | CH₂NH₂ | 1 | 0 | CO₂Me | -C(=O)NH-(pyrimidin-2-yl)-5-(2-SO₂NH₂-phenyl) |

TABLE 13

I-13

[Structure: isoxazoline core with R² and (CH₂)ₙ substituent, (CH₂)ₘ—U—V—Z—D chain, connected to a phenyl ring bearing a C(=NH)NH₂ amidine group]

| Cpd. # | n | m | R² | -U-V-Z-D |
|---|---|---|---|---|
| 1 | 1 | 0 | CO₂Me | —C(=O)NH—C₆H₄—C₆H₃(SO₂NH₂)(Me) (2-SO₂NH₂, 3-Me biphenyl) |
| 2 | 1 | 0 | CO₂Me | —C(=O)NH—C₆H₄—C₆H₃(SO₂NH₂)(NH₂) (2-SO₂NH₂, 4-NH₂ biphenyl) |
| 3 | 1 | 0 | CO₂Me | —C(=O)NH—C₆H₄—C₆H₄(2-Me) |
| 4 | 1 | 0 | CO₂Me | —C(=O)NH—C₆H₄—C₆H₄(2-OMe) |
| 5 | 1 | 0 | CO₂Me | —C(=O)NH—C₆H₄—C₆H₄(3-SO₂NH₂) |
| 6 | 1 | 0 | CO₂Me | —C(=O)NH—C₆H₄—pyridyl(SO₂NH₂) |

TABLE 13-continued
I-13
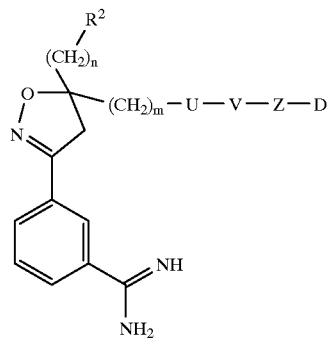
| Cpd. # | n | m | R² | -U-V-Z-D |
|---|---|---|---|---|
| 7 | 1 | 0 | CO₂Me | 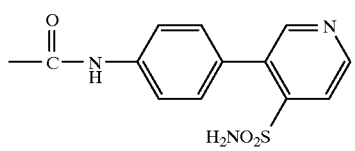 |
| 8 | 1 | 0 | CO₂Me | 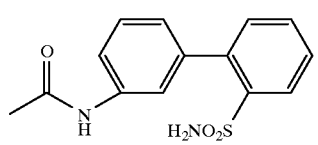 |
| 9 | 1 | 0 | CO₂Me | 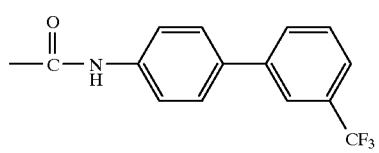 |
| 10 | 1 | 0 | CO₂Me | 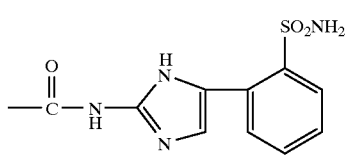 |
| 11 | 1 | 0 | CO₂Me | 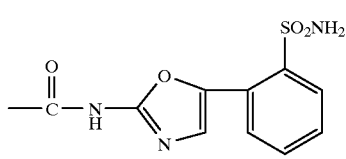 |
| 12 | 1 | 0 | CO₂Me | 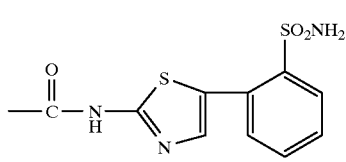 |

TABLE 13-continued

I-13

[Structure: 3-(5-(CH₂R²)-5-((CH₂)ₘ-U-V-Z-D)-4,5-dihydroisoxazol-3-yl)benzamidine]

| Cpd. # | n | m | R² | -U-V-Z-D |
|---|---|---|---|---|
| 13 | 1 | 0 | CO₂Me | -C(O)NH-(5-thiazolyl)-2-(2-sulfamoylphenyl) |
| 14 | 1 | 0 | CO₂Me | -C(O)NH-(4-phenyl)-2'-SO₂NH₂-3'-OMe-biphenyl |
| 15 | 1 | 0 | CO₂Me | -C(O)NH-(4-phenyl)-2'-SO₂NH₂-3'-F-biphenyl |
| 16 | 1 | 0 | CO₂Me | -C(O)NH-(4-phenyl)-2'-SO₂NMe₂-biphenyl |
| 17 | 1 | 0 | CO₂Me | -C(O)NH-(4-phenyl)-2'-SO₂NHCOMe-biphenyl |
| 18 | 1 | 0 | CO₂Me | -C(O)NH-(4-phenyl)-2'-SO₂NHCO₂Me-biphenyl |

TABLE 13-continued
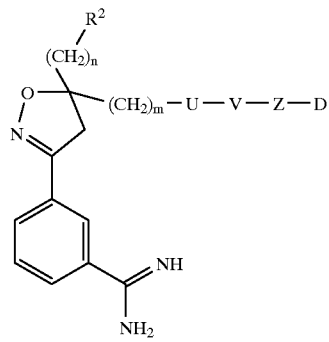
I-13
| Cpd. # | n | m | R² | -U-V-Z-D |
|---|---|---|---|---|
| 19 | 1 | 0 | CO₂Me | 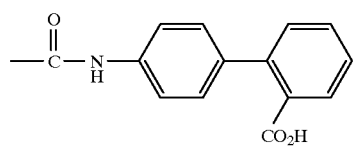 |
| 20 | 1 | 0 | CO₂Me | 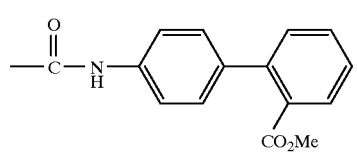 |
| 21 | 1 | 0 | CO₂Me | 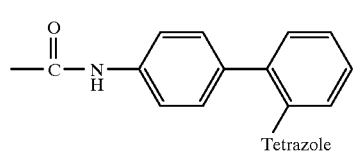 |
| 22 | 1 | 0 | CO₂Me | 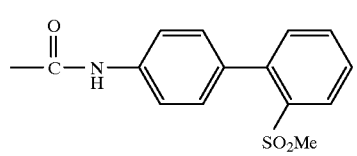 |
| 23 | 1 | 0 | CO₂Me | 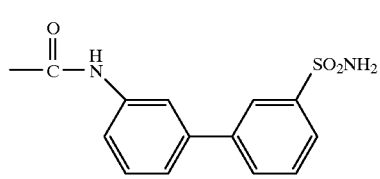 |
| 24 | 1 | 0 | CO₂Me | 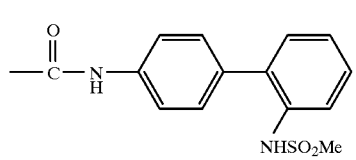 |

TABLE 13-continued
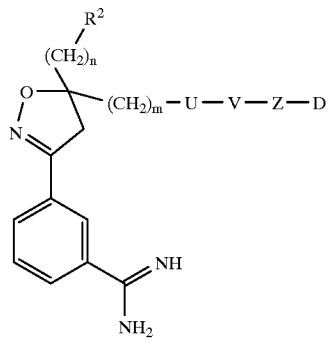
I-13
| Cpd. # | n | m | R² | -U-V-Z-D |
|---|---|---|---|---|
| 25 | 1 | 0 | CO₂Me | 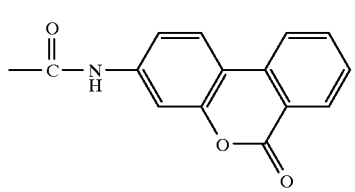 |
| 26 | 1 | 0 | CO₂Me | 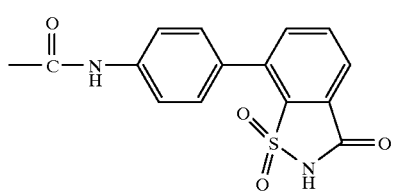 |
| 27 | 1 | 0 | CO₂Me | 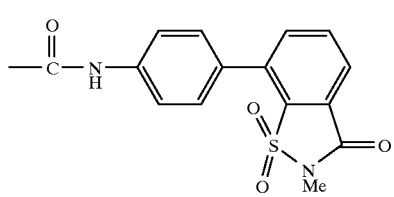 |
| 28 | 0 | 0 | H | 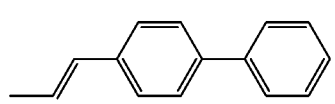 |
| 29 | 0 | 0 | CONHCH₂CO₂Me | 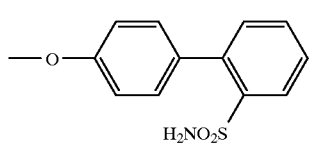 |
| 30 | 0 | 0 | CONHCH₂CO₂H | 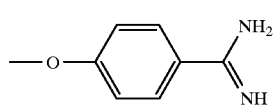 |

TABLE 13-continued
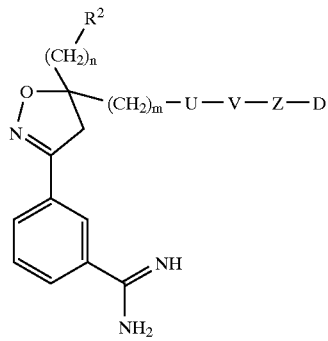
I-13
| Cpd. # | n | m | R² | -U-V-Z-D |
|---|---|---|---|---|
| 31 | 0 | 0 | CH₂OMe | 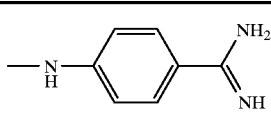 |
| 32 | 0 | 0 | CH=CH₂ | 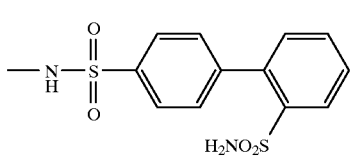 |
| 33 | 0 | 0 | CH=CHCO₂Me | 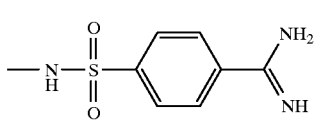 |
| 34 | 0 | 0 | CH=CHCO₂H | 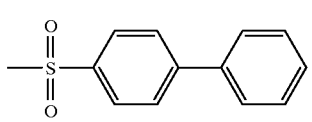 |
| 35 | 0 | 0 | CH=CHCONH₂ | 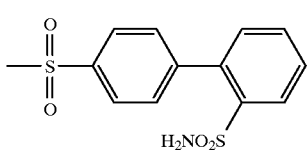 |
| 36 | 0 | 0 | CH=CHCONH—CH₂CO₂Me | 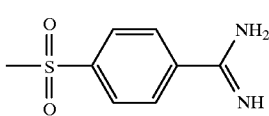 |
| 37 | 0 | 0 | CH=CHCONH—(CH₂)₂-4-imidazole | 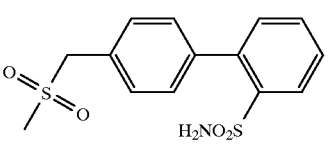 |

TABLE 13-continued

I-13

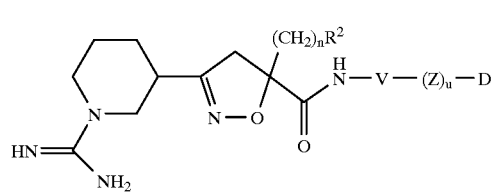

| Cpd. # | n | m | R² | -U-V-Z-D |
|---|---|---|---|---|
| 38 | 0 | 0 | CH=CHCH₂OH | (4'-methylthiomethyl-2-sulfamoylbiphenyl) |
| 39 | 0 | 0 | CH=CHCH₂OMe | (N-biphenyl-4-yl methanesulfonamide) |
| 40 | 1 | 0 | CO₂Me | (N-(2'-sulfamoylbiphenyl-4-yl)methanesulfonamide) |
| 41 | 1 | 0 | CO₂Me | (N-(4-amidinophenyl)methanesulfonamide) |

TABLE 14

I-14

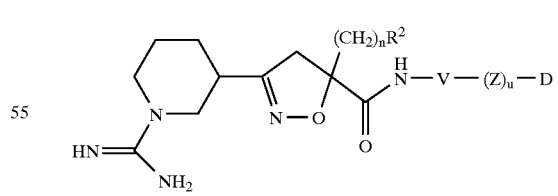

| Cpd | (CH₂)ₙR² | V | (Z)ᵤ-D |
|---|---|---|---|
| 1 | CH₂OMe | phenyl | 2-aminosulfonylphenyl |
| 2 | CH₂OEt | phenyl | 2-aminosulfonylphenyl |
| 3 | CH₂O-n-Pr | phenyl | 2-aminosulfonylphenyl |
| 4 | CH₂O-i-Pr | phenyl | 2-aminosulfonylphenyl |
| 5 | CH₂O-n-Bu | phenyl | 2-aminosulfonylphenyl |
| 6 | CH₂O-i-Bu | phenyl | 2-aminosulfonylphenyl |
| 7 | CH₂Ph | phenyl | 2-aminosulfonylphenyl |

TABLE 14-continued

I-14

| Cpd | (CH₂)ₙR² | V | (Z)ᵤ-D |
|---|---|---|---|
| 8 | CH₂-pyrazol-1-yl | phenyl | 2-aminosulfonylphenyl |
| 9 | CH₂-imidazol-1-yl | phenyl | 2-aminosulfonylphenyl |
| 10 | CH₂-tetrazol-1-yl | phenyl | 2-aminosulfonylphenyl |
| 11 | CH₂tetrazol-2-yl | phenyl | 2-aminosulfonylphenyl |
| 12 | CH₂triazol-1-yl | phenyl | 2-aminosulfonylphenyl |
| 13 | CH₂SEt | phenyl | 2-aminosulfonylphenyl |
| 14 | CH₂SO₂Et | phenyl | 2-aminosulfonylphenyl |

TABLE 14-continued

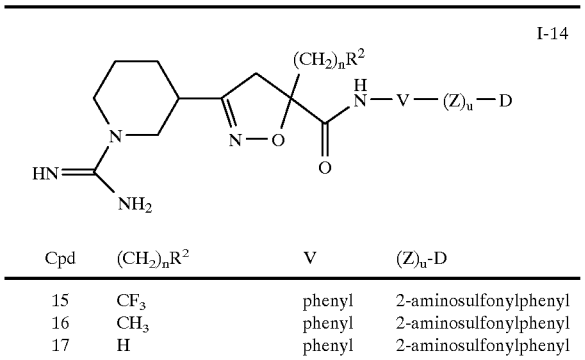

I-14

| Cpd | (CH$_2$)$_n$R$^2$ | V | (Z)$_u$-D |
|---|---|---|---|
| 15 | CF$_3$ | phenyl | 2-aminosulfonylphenyl |
| 16 | CH$_3$ | phenyl | 2-aminosulfonylphenyl |
| 17 | H | phenyl | 2-aminosulfonylphenyl |

TABLE 15

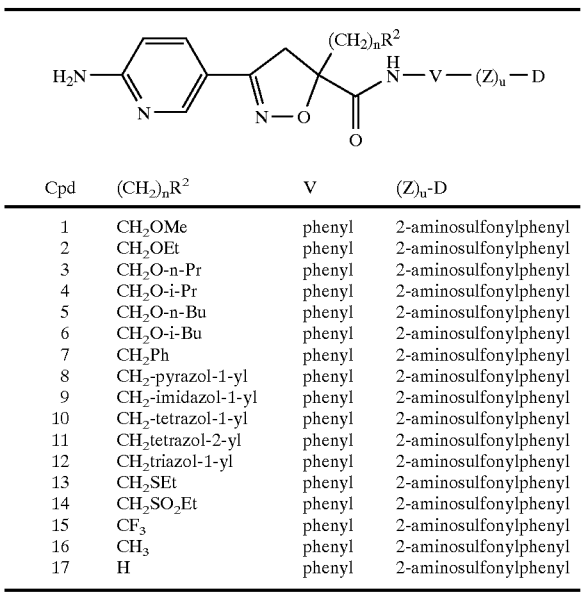

| Cpd | (CH$_2$)$_n$R$^2$ | V | (Z)$_u$-D |
|---|---|---|---|
| 1 | CH$_2$OMe | phenyl | 2-aminosulfonylphenyl |
| 2 | CH$_2$OEt | phenyl | 2-aminosulfonylphenyl |
| 3 | CH$_2$O-n-Pr | phenyl | 2-aminosulfonylphenyl |
| 4 | CH$_2$O-i-Pr | phenyl | 2-aminosulfonylphenyl |
| 5 | CH$_2$O-n-Bu | phenyl | 2-aminosulfonylphenyl |
| 6 | CH$_2$O-i-Bu | phenyl | 2-aminosulfonylphenyl |
| 7 | CH$_2$Ph | phenyl | 2-aminosulfonylphenyl |
| 8 | CH$_2$-pyrazol-1-yl | phenyl | 2-aminosulfonylphenyl |
| 9 | CH$_2$-imidazol-1-yl | phenyl | 2-aminosulfonylphenyl |
| 10 | CH$_2$-tetrazol-1-yl | phenyl | 2-aminosulfonylphenyl |
| 11 | CH$_2$tetrazol-2-yl | phenyl | 2-aminosulfonylphenyl |
| 12 | CH$_2$triazol-1-yl | phenyl | 2-aminosulfonylphenyl |
| 13 | CH$_2$SEt | phenyl | 2-aminosulfonylphenyl |
| 14 | CH$_2$SO$_2$Et | phenyl | 2-aminosulfonylphenyl |
| 15 | CF$_3$ | phenyl | 2-aminosulfonylphenyl |
| 16 | CH$_3$ | phenyl | 2-aminosulfonylphenyl |
| 17 | H | phenyl | 2-aminosulfonylphenyl |

TABLE 16

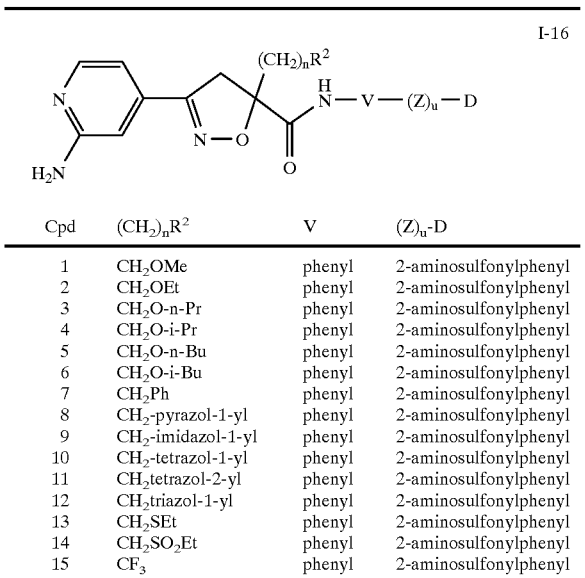

I-16

| Cpd | (CH$_2$)$_n$R$^2$ | V | (Z)$_u$-D |
|---|---|---|---|
| 1 | CH$_2$OMe | phenyl | 2-aminosulfonylphenyl |
| 2 | CH$_2$OEt | phenyl | 2-aminosulfonylphenyl |
| 3 | CH$_2$O-n-Pr | phenyl | 2-aminosulfonylphenyl |
| 4 | CH$_2$O-i-Pr | phenyl | 2-aminosulfonylphenyl |
| 5 | CH$_2$O-n-Bu | phenyl | 2-aminosulfonylphenyl |
| 6 | CH$_2$O-i-Bu | phenyl | 2-aminosulfonylphenyl |
| 7 | CH$_2$Ph | phenyl | 2-aminosulfonylphenyl |
| 8 | CH$_2$-pyrazol-1-yl | phenyl | 2-aminosulfonylphenyl |
| 9 | CH$_2$-imidazol-1-yl | phenyl | 2-aminosulfonylphenyl |
| 10 | CH$_2$-tetrazol-1-yl | phenyl | 2-aminosulfonylphenyl |
| 11 | CH$_2$tetrazol-2-yl | phenyl | 2-aminosulfonylphenyl |
| 12 | CH$_2$triazol-1-yl | phenyl | 2-aminosulfonylphenyl |
| 13 | CH$_2$SEt | phenyl | 2-aminosulfonylphenyl |
| 14 | CH$_2$SO$_2$Et | phenyl | 2-aminosulfonylphenyl |
| 15 | CF$_3$ | phenyl | 2-aminosulfonylphenyl |

TABLE 16-continued

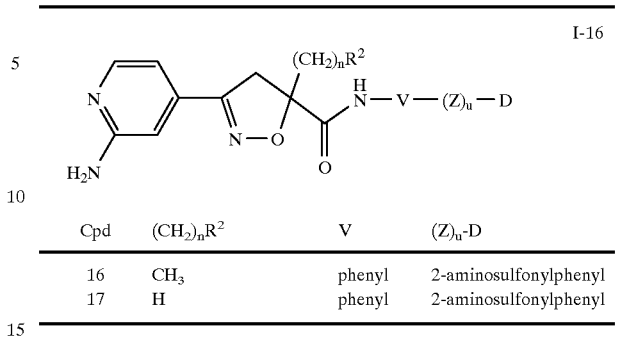

I-16

| Cpd | (CH$_2$)$_n$R$^2$ | V | (Z)$_u$-D |
|---|---|---|---|
| 16 | CH$_3$ | phenyl | 2-aminosulfonylphenyl |
| 17 | H | phenyl | 2-aminosulfonylphenyl |

TABLE 17

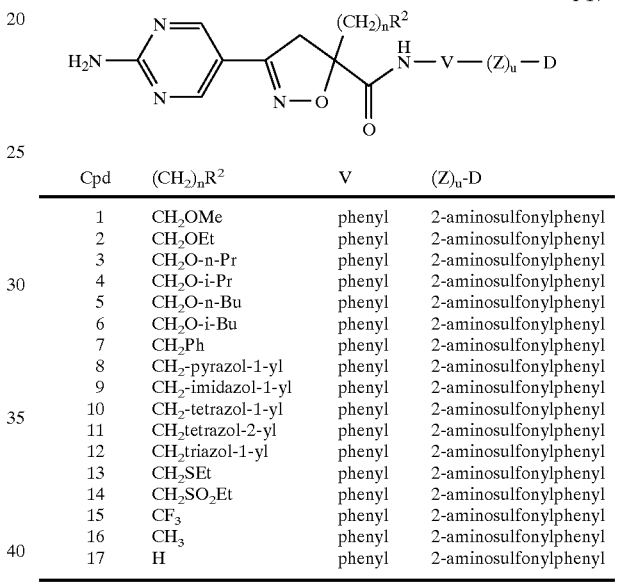

I-17

| Cpd | (CH$_2$)$_n$R$^2$ | V | (Z)$_u$-D |
|---|---|---|---|
| 1 | CH$_2$OMe | phenyl | 2-aminosulfonylphenyl |
| 2 | CH$_2$OEt | phenyl | 2-aminosulfonylphenyl |
| 3 | CH$_2$O-n-Pr | phenyl | 2-aminosulfonylphenyl |
| 4 | CH$_2$O-i-Pr | phenyl | 2-aminosulfonylphenyl |
| 5 | CH$_2$O-n-Bu | phenyl | 2-aminosulfonylphenyl |
| 6 | CH$_2$O-i-Bu | phenyl | 2-aminosulfonylphenyl |
| 7 | CH$_2$Ph | phenyl | 2-aminosulfonylphenyl |
| 8 | CH$_2$-pyrazol-1-yl | phenyl | 2-aminosulfonylphenyl |
| 9 | CH$_2$-imidazol-1-yl | phenyl | 2-aminosulfonylphenyl |
| 10 | CH$_2$-tetrazol-1-yl | phenyl | 2-aminosulfonylphenyl |
| 11 | CH$_2$tetrazol-2-yl | phenyl | 2-aminosulfonylphenyl |
| 12 | CH$_2$triazol-1-yl | phenyl | 2-aminosulfonylphenyl |
| 13 | CH$_2$SEt | phenyl | 2-aminosulfonylphenyl |
| 14 | CH$_2$SO$_2$Et | phenyl | 2-aminosulfonylphenyl |
| 15 | CF$_3$ | phenyl | 2-aminosulfonylphenyl |
| 16 | CH$_3$ | phenyl | 2-aminosulfonylphenyl |
| 17 | H | phenyl | 2-aminosulfonylphenyl |

TABLE 18

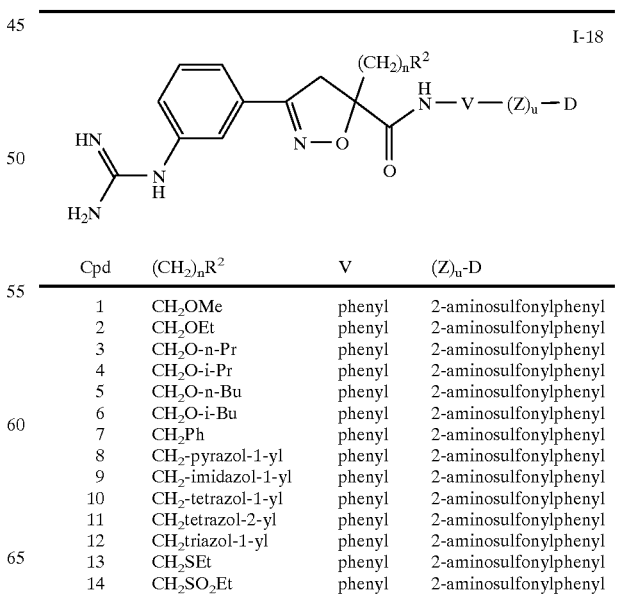

I-18

| Cpd | (CH$_2$)$_n$R$^2$ | V | (Z)$_u$-D |
|---|---|---|---|
| 1 | CH$_2$OMe | phenyl | 2-aminosulfonylphenyl |
| 2 | CH$_2$OEt | phenyl | 2-aminosulfonylphenyl |
| 3 | CH$_2$O-n-Pr | phenyl | 2-aminosulfonylphenyl |
| 4 | CH$_2$O-i-Pr | phenyl | 2-aminosulfonylphenyl |
| 5 | CH$_2$O-n-Bu | phenyl | 2-aminosulfonylphenyl |
| 6 | CH$_2$O-i-Bu | phenyl | 2-aminosulfonylphenyl |
| 7 | CH$_2$Ph | phenyl | 2-aminosulfonylphenyl |
| 8 | CH$_2$-pyrazol-1-yl | phenyl | 2-aminosulfonylphenyl |
| 9 | CH$_2$-imidazol-1-yl | phenyl | 2-aminosulfonylphenyl |
| 10 | CH$_2$-tetrazol-1-yl | phenyl | 2-aminosulfonylphenyl |
| 11 | CH$_2$tetrazol-2-yl | phenyl | 2-aminosulfonylphenyl |
| 12 | CH$_2$triazol-1-yl | phenyl | 2-aminosulfonylphenyl |
| 13 | CH$_2$SEt | phenyl | 2-aminosulfonylphenyl |
| 14 | CH$_2$SO$_2$Et | phenyl | 2-aminosulfonylphenyl |

TABLE 18-continued

I-18

[Structure: phenyl ring with HN=C(NH2)-NH- substituent, attached to isoxazoline ring (N—O) with (CH2)nR2 and C(=O)NH—V—(Z)u—D groups]

| Cpd | (CH2)nR2 | V | (Z)u-D |
|---|---|---|---|
| 15 | CF3 | phenyl | 2-aminosulfonylphenyl |
| 16 | CH3 | phenyl | 2-aminosulfonylphenyl |
| 17 | H | phenyl | 2-aminosulfonylphenyl |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, pulmonary embolisms.

The anticoagulant effect of compounds of this invention is due to inhibition of Factor Xa. The activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (Factor Xa, Factor V, $Ca^{2+}$ and phospholipid). Since it is calculated that one molecule of Factor Xa can generate 138 molecules of thrombin (Elodi, S., Varadi, K.: Optimization of conditions for the catalytic effect of the factor IXa-factor VIII COomplex: Probable role of the complex in the amplification of blood coagulation. *Thromb. Res.* 1979, 15, 617–629), inhibition of factor Xa may be more efficient that inactivation of thrombin in interrupting the blood coagulation system.

The effectiveness of the compounds of the invention as inhibitors of Factor Xa was determined using purified human Factor Xa and synthetic substrate. The rate of Factor Xa hydrolysis of chromogenic substrate S2222 (Kabi Pharmacia, Franklin, OH) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk.

Values of $K_i$ were determined by allowing 0.2–0.5 nM human Factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values.

$$\frac{v_o - v_s}{v_s} = \frac{I}{K_i(1 + S/K_m)}$$

where:

$v_o$ is the velocity of the control in the absence of inhibitor;
$v_s$ is the velocity in the presence of inhibitor;
I is the concentration of inhibitor;
$K_i$ is the dissociation constant of the enzyme: inhibitor complex;
S is the concentration of substrate;
$K_m$ is the Michaelis constant.

The antithrombotic effect of the compounds of this invention can be demonstrated in a rat vena cava thrombosis model. In this model Male Sprague-Dawley rats weighing 350–450 grams anesthetized with a mixture of xylazine (10 mg/kg i.m.) and ketamine (110 mg/kg i.m.) are used. A carotid artery, a jugular vein and a femoral vein are cannulated for blood sampling, drug infusion and hypotonic saline injection, respectively. The abdominal vena cava is isolated and all its side-branches are ligated beneath the left renal vein. Thrombus formation is induced by rapid injection of 1 ml hypotonic saline (0.225%) into the vena cava. This is followed 15 seconds later by a 15-minute stasis of an isolated segment (about 1 cm) of the vena cava. The formed thrombus in the vena cava is removed and immediately weighed.

Test compounds or vehicle are given as continuous intravenous infusions or orally starting 1 hour before the injection of hypotonic saline. Arterial blood samples (1.5 ml) for the determination of clotting times are collected before and 1 hour after the infusion or oral dosing of test compounds or vehicle. The percentage inhibition of thrombus formation is determined for each treatment group. The ID50 values (dose which produces 50% inhibition of thrombus formation) are estimated by linear regression.

The compounds of this invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin and heparin, as well as other Factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosures of which are hereby incorporated herein by reference herein, in their entirety. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of Factor Xa. Such compounds may be provided in a commercial kit, for example, for use in pharmaceutical research involving Factor Xa. The compounds of the present invention may also be used in diagnostic assays involving Factor Xa.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

We claim:

1. Compounds of Formula I:

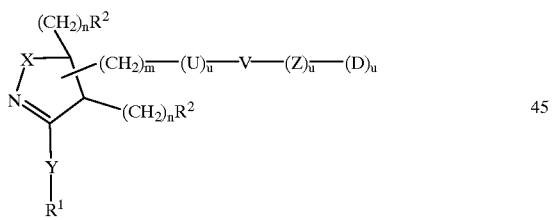

(I)

including pharmaceutically acceptable salts, and all stereoisomeric forms thereof and mixtures of such stereoisomeric forms, wherein:

U when present is selected from
—CO—NH—$(CH_2)_o$—
—CO—$(CH_2)_o$—
—$SO_2$—NH—$(CH_2)_o$—
—$SO_2$—$(CH_2)_o$—
—$NHSO_2$—$(CH_2)_o$—, provided m≠0
—NHCO—$(CH_2)_o$—, provided m≠0
—NH—$(CH_2)_o$—, provided m≠0
—O—$(CH_2)_o$—, provided m≠0
—S—$(CH_2)_o$—, provided m≠0
—CH=CH—$(CH_2)_o$—

X is O, S, $NR^{15}$

Y is selected from

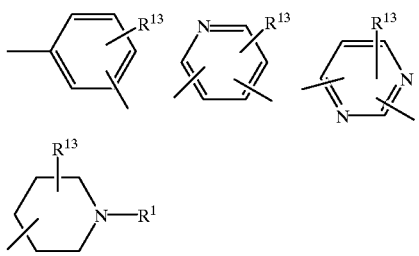

$R^1$ is selected from
$(CH_2)_p NR^5 R^6$
$C(NR^{14})NR^5 R^6$
$NHC(NR^{14})NR^5 R^6$
$NHC(NR^{14})H$
$CONR^5 R^6$ $R^2$ is selected from
H
$C_1$-$C_6$ alkyl
$C_1$-$C_6$ alkoxy
$CO_2 R^5$
$CONHR^5$
$CONHCH_2 CO_2 R^5$
$CONH(CH_2)_q$—$R^{10}$
$R^{10}$
CO—$R^5$
$COCO_2 R^5$
$COCONHR^5$
$SO_n R^5$
$SO_2 NHR^5$
$NHR^7$
CH=$CHCO_2 R^5$
CH=$CHCONHR^5$
O—$(CH_2)_n$—$R^{10}$
$SO_n$—$(CH_2)_n$—$R^{10}$
NH—$(CH_2)_n$—$R^{10}$ U and $R^2$ taken together provide a spiro compound of formula IIa and IIb, or a compound of formula IIIa or IIIb:

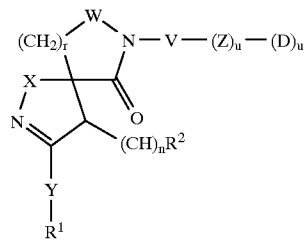

IIa

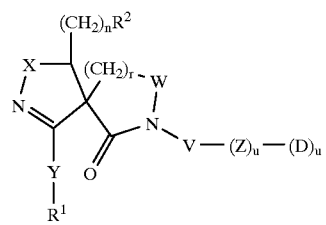

IIb where W=CO, CH$_2$, CHOR$^5$ and r=1–3
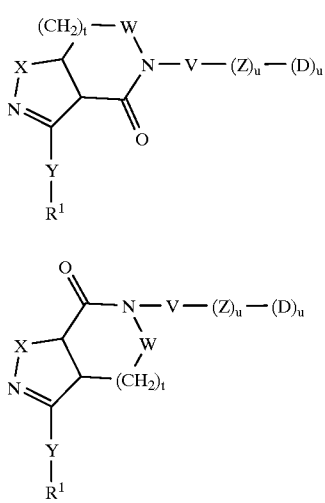
IIIa
IIIb
where W=CO, CH$_2$, CHOR$^5$ and t=0–2
R$^3$ is selected from
(CH$_2$)$_s$NR$^5$R$^6$
C(NR$^{14}$)NR$^5$R$^6$
NHC(NR$^{14}$)NR$^5$R$^6$
NHC(NR$^{14}$)H
CONR$^5$R$^6$
V is selected from the following when Z and D are both absent:
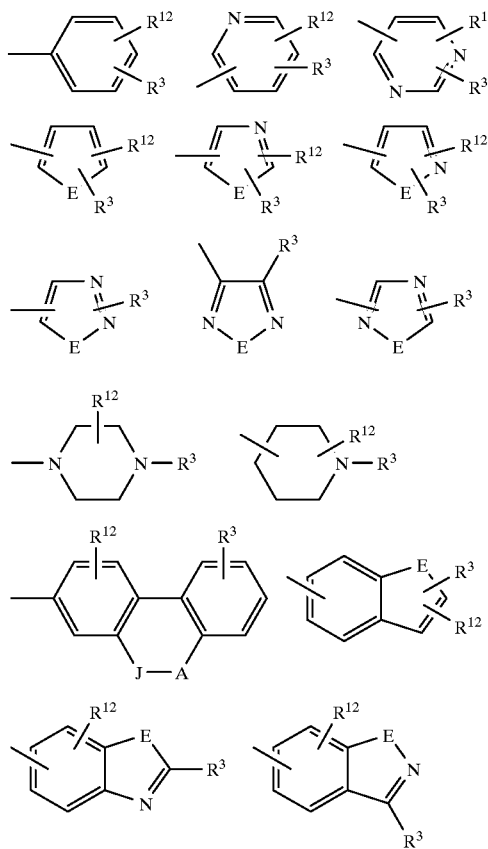
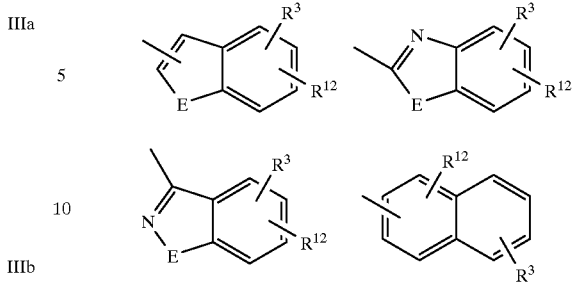
-continued
V is selected from the following when Z and/or D are present:
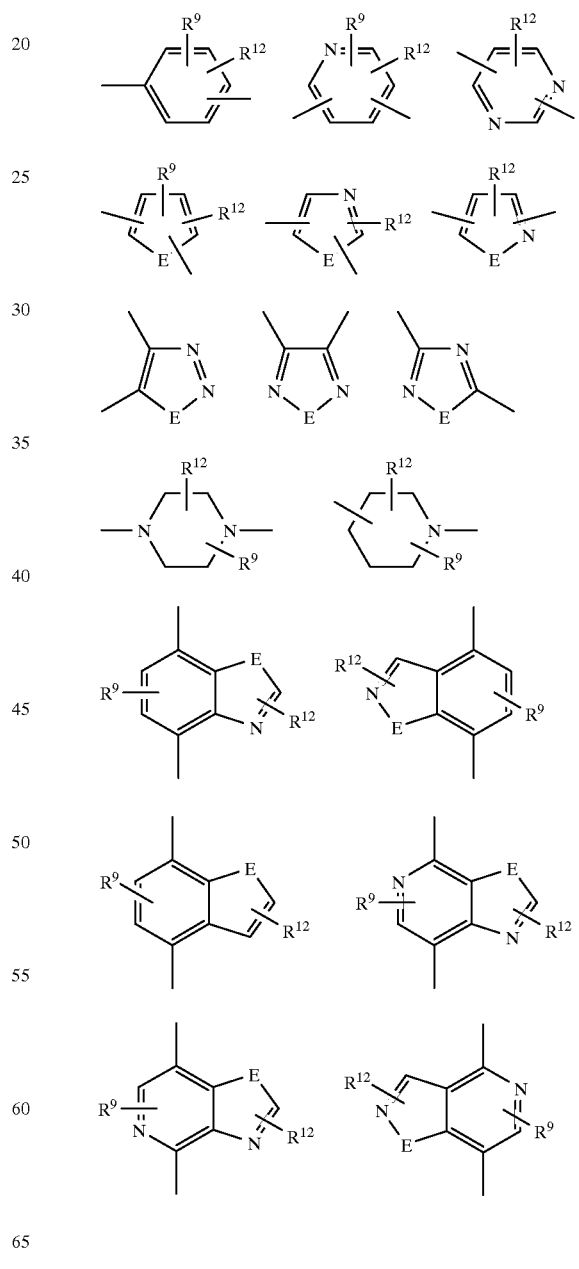

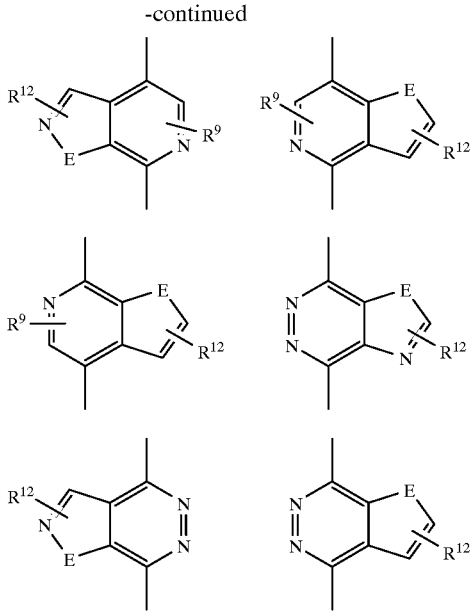

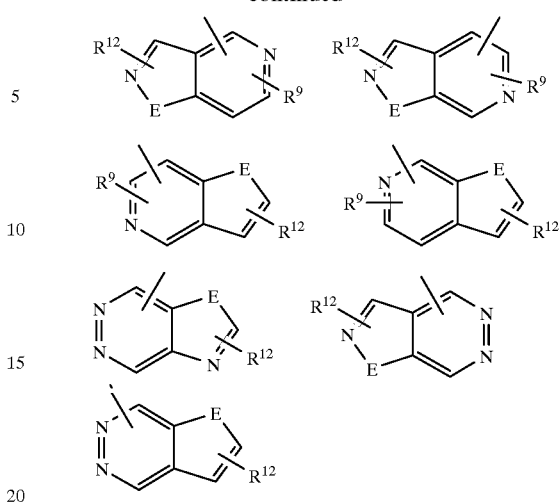

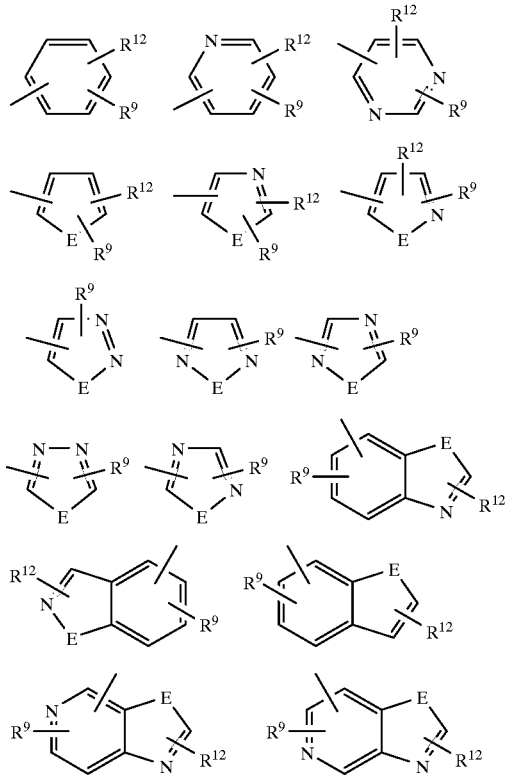

Z when present is selected from a single bond,
—CO—,
—(CH$_2$)$_r$—,
—SO$_n$—,
—SO$_2$NHR$^4$, provided D is absent
—NH—,
—NR$^7$—,
—O—

D when present is selected from

E is selected from N, NR$^5$, O, S;
J is selected from O, NR$^7$;
A is selected from CO, CH$_2$, SO, SO$_2$
R$^4$ is selected from
 H
 C$_1$–C$_6$ alkyl
 (CH$_2$)$_n$-phenyl
 (CH$_2$)$_n$-CONHR$^5$
 (CH$_2$)$_n$-CONHR$^5$CH$_2$CO$_2$R$^5$
R$^5$ and R$^6$ at each appearance are independently
 H
 C$_1$–C$_6$ alkyl
 (CH$_2$)$_n$-phenyl
R$^7$ is selected from
 H
 C$_1$–C$_6$ alkyl
 SO$_2$R$^5$
 COR$^5$
 (CH$_2$)$_r$—R$^{10}$
 (CH$_2$)$_n$-phenyl
R$^8$ is selected from
 H
 C$_1$–C$_6$ alkyl
 halogen
 NO$_2$
 CF$_3$
 OR$^5$
R$^9$ is selected from
 H
 C$_1$–C$_6$ alkyl
 halogen
 NO$_2$
 NHR$^7$
 SO$_2$NHR$^{11}$
 CF$_3$
 OR$^5$
 CO$_2$R$^5$
 CONR$^5$R$^7$
 CN
 (CH$_2$)$_p$NR$^5$R$^6$
 C(NR$^{14}$) NR$^5$R$^6$
 NHC(NR$^{14}$)NR$^5$R$^6$
 NHC(NR$^{14}$)H
 SO$_n$—R$^5$
 SO$_n$—CF$_3$ imidazole, pyrazole, 1,2,3-triazole, 1,2,4-triazole and tetrazole, each optionally substituted with $CF_3$, halogen, $NO_2$, $C_1$–$C_5$ alkyl, or $C_1$–$C_5$ alkoxy;

$R^{10}$ is selected from

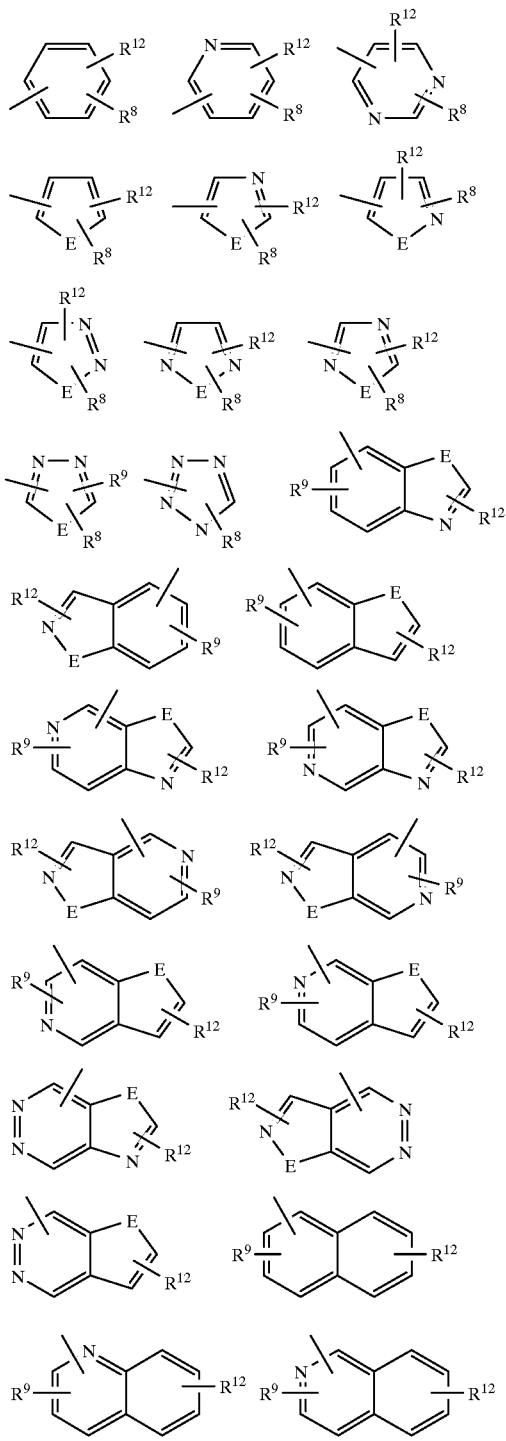

$R^{11}$ is selected from
H
$C_1$–$C_6$ alkyl
$(CH_2)_n$-phenyl
$COR^5$
$CO_2R^5$ $R^{12}$ is selected from
H
$C_1$–$C_6$ alkyl
$C_1$–$C_6$ alkoxy
halogen
$NO_2$
$NH_2$
$NH(C_1$–$C_6$ alkyl)
$NHSO_2R^5$
$NHCOR^5$
$NH(CH_2)_n$-phenyl
CN
$CF_3$
$SONHR^{11}$ $R^{13}$ is selected from
H
OH
$C_1$–$C_{10}$ alkyl
$C_1$–$C_{10}$ alkoxy
nitro
halo
$CF_3$ $R^{14}$ is selected from
H
OH
$C_1$–$C_{10}$ alkyl
$C_1$–$C_{10}$ alkoxy
$CO_2$—$C_1$–$C_{10}$ alkyl
CO—$C_1$–$C_{10}$ alkyl
CONH—$C_1$–$C_{10}$ alkyl
CONH-phenyl
$CO_2(CH_2)_n$-phenyl;

$R^{15}$ is selected from
H
$C_1$–$C_6$ alkyl,
$C_1$–$C_6$ alkoxy
$CO_2R^{14}$
$CONHR^{14}$
$CONHCH_2CO_2R^5$
$CONH(CH_2)_q$—$R^{10}$
$(CH_2)_nR^{10}$
CO—$R^5$
$COCO_2R^5$
$COCONHR^5$
$SO_2NHR^5$ at each appearance each of the following are independently:
m=0–2
n=0–4, except that in —$SO_n$—, n=0–2;
o=0–2
p=0–1
q=0–4
r=1–2
s=0–2
t=0–2
u=0–1, provided that, when X is $NR^{15}$, Z and D are both absent,

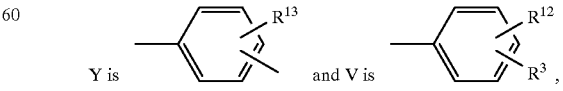

then at least one of $R^1$ and $R^3$ must be
$C(NR^{14})NR^5R^6$
$NHC(NR^{14})NR^5R^6$ or

NHC(NR$^{14}$)H.

2. Compounds of claim 1 wherein:

U is present and is selected from
—CO—NH—(CH$_2$)$_o$—
—CO—(CH$_2$)$_o$—
—SO$_2$—NH—(CH$_2$)$_o$—
—SO$_2$—(CH$_2$)$_o$—
—NH—(CH$_2$)$_o$—
—O—(CH$_2$)$_o$— is O

Y is selected from

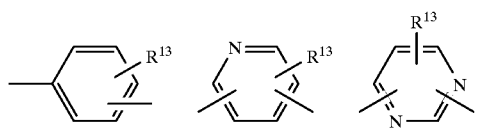

R$^1$ is selected from
C(NR$^{14}$)NR$^5$R$^6$
NHC(NR$^{14}$)NR$^5$R$^6$

R$^2$ is selected from
H
C$_1$–C$_6$ alkyl
C$_1$–C$_6$ alkoxy
CO$_2$R$^5$
CONHR$^5$
CONHCH$_2$CO$_2$R$^5$
CONH(CH$_2$)$_q$—R$^{10}$
R$^{10}$
CO—R$^5$
COCO$_2$R$^5$
COCONHR$^5$
SO$_n$R$^5$
SO$_2$NHR$^5$
NHR$^7$
CH=CHCO$_2$R$^5$
CH=CHCONHR$^5$
O—(CH)$_n$—R$^{10}$
SO$_n$—(CH)$_n$—R$^{10}$
NH—(CH)$_n$—R$^{10}$ V is selected from the following when Z and/or D are present:

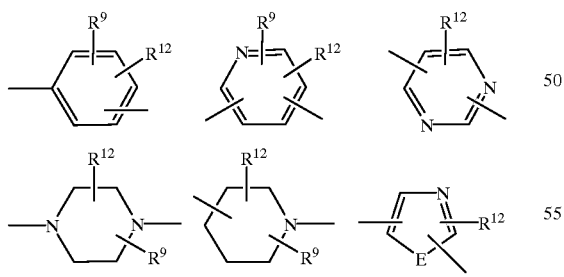

V is selected from the following when Z and D are both absent:

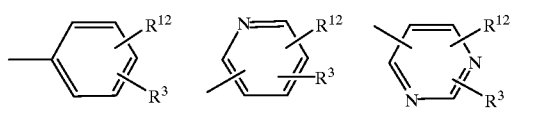

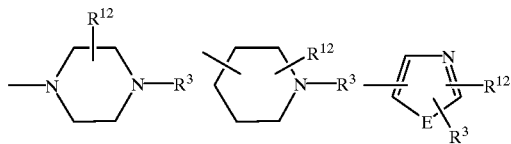

D when present is selected from

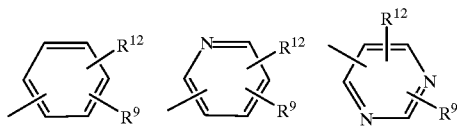

R$^{10}$ is selected from

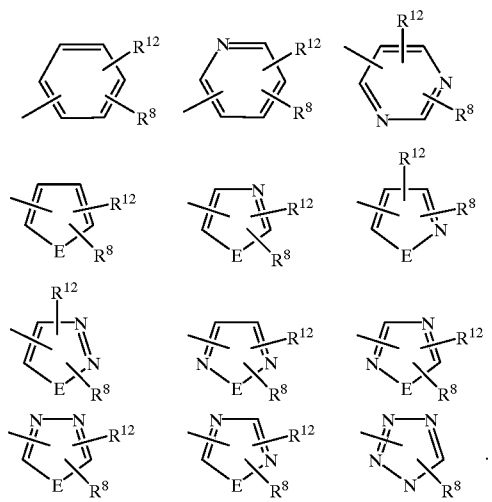

3. Compounds of claim 2 wherein:
U is —CO—NH—(CH$_2$)$_o$—
Y is selected from

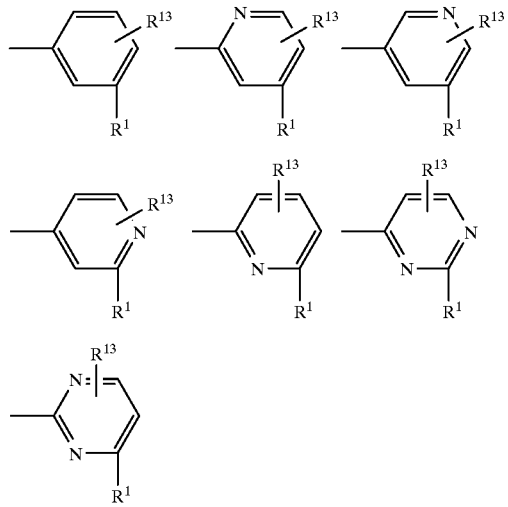

R$^1$ is C(NR$^{14}$)NR$^5$R$^6$
Z is absent or is present and is selected from —O— and —NR$^7$—.

4. Compounds of claim 3 having the structures of V and VI:

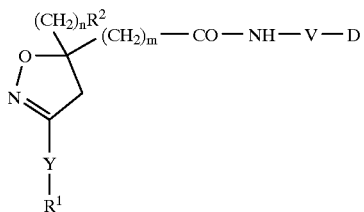
(V)

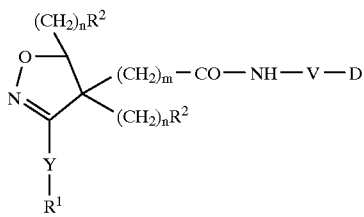
(VI)

wherein
$R^1$ is $C(NR^{14})NR^5R^6$ and
D is selected from

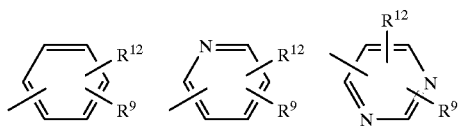

V is selected from the following:

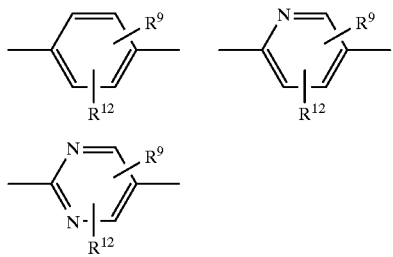

5. A compound of claim 1 selected from the group consisting of the following compounds, including pharmaceutically acceptable salt, and all stereoisomeric forms thereof and mixtures of such stereoisomeric forms:

3-(3-Amidinophenyl)-5-[(2-naphthylsulfonyl)amino]methyl-isoxazoline 3-(3-amidinophenyl)-5-[[(2'-aminosulfonyl-[1,1']-biphenyl-4-yl)-methyl]aminocarbonyl]-5-(carbomethoxymethyl)isoxazoline 3-(3-amidinophenyl)-5-[[(2'-aminosulfonyl-[1,1']-biphenyl-4-yl)methyl]aminocarbonyl]-5-(aminocarbonylmethyl)isoxazoline 3-(3-amidinophenyl)-7-(2'-aminosulfonyl-[1,1']-biphenyl-4-yl)methyl[1-oxa-2,7-diazaspiro[4,4]non-2-ene-6,8-diones 3-amidinophenyl 3-(4-amidinophenyl)-5-[(aminocarbonyl)isoxazolin-5-yl]acetamide 4-amidinophenyl 3-(3-amidinophenyl)-5-[(carbometoxy)isoxazolin-5-yl]acetamide 3-(3-amidinophenyl)-5-[(4-amidinophenyl)aminocarbonyl]isoxazoline 3-(3-amidinophenyl)-5-[(4-amidinophenyl)aminocarbonyl]-5-[(carbomethoxymethyl)aminocarbonylmethyl]isoxazoline 3-(3-amidinophenyl)-5-[(4-amidinophenyl)aminocarbonyl]-5-(carboxymethyl)isoxazoline 3-(4-amidinophenyl)-5-[(3-amidinophenyl)aminocarbonyl]-5-(carbomethoxymethyl)isoxazoline 3-(3-amidinophenyl)-5-[(4-amidinophenyl)methylaminocarbonyl]-5-(carbomethoxymethyl)isoxazoline 3-(3-amidinophenyl)-5-[(4-benzenesulfonylpiperidin-1-yl)carbonyl]-5-(carbomethoxymethyl)isoxazoline 3-(3-amidinophenyl)-5-[[(4-pyrimidin-5-yl)piperidin-1-yl]carbonyl]-5-(carbomethoxymethyl)isoxazoline 3-(3-amidinophenyl)-5-[(4-benzenesulfonylphenyl-1-yl)aminocarbonyl]-5-(carbomethoxymethyl)isoxazoline 3-(3-amidinophenyl)-5-[(4-amidinophenyl)aminocarbonyl]-5-(carbomethoxymethyl)isoxazoline 3-(3-amidinophenyl)-5-[([1,1']-biphenyl-4-yl)aminocarbonyl]-5-(carbomethoxymethyl)isoxazoline 3-(3-amidinophenyl)-5-[([1,1']-biphenyl-4-yl)aminocarbonyl]-5-(carboxymethyl)isoxazoline 3-(3-amidinophenyl)-5-[([1,1']-biphenyl-4-yl)aminocarbonyl]-5-(aminocarbonylmethyl)isoxazoline 3-(3-amidinophenyl)-5-[([1,1']-biphenyl-4-yl)aminocarbonyl]-5-(hydroxymethyl)isoxazoline 3-(3-amidinophenyl)-5-[(2'-aminosulfonyl-3'-n-propyl-[1,1']-biphenyl-4-yl)aminocarbonyl]-5-(carbomethoxymethyl)isoxazoline 3-(3-amidinophenyl)-5-[(2'-t-butylaminosulfonyl-[1,1']-biphenyl-4-yl)aminocarbonyl]-5-(carbomethoxymethyl)isoxazoline 3-(3-amidinophenyl)-5-[(2'-t-butylaminosulfonyl-[1,1']-biphenyl-4-yl)aminocarbonyl]-5-(aminocarbonylmethyl)isoxazoline 3-(3-amidinophenyl)-5-[(4'-amino-[1,1']-biphenyl-4-yl)aminocarbonyl]-5-(carbomethoxymethyl)isoxazoline 3-(3-amidinophenyl)-5-[(2'-trifluoromethyl-[1,1']-biphenyl-4-yl)aminocarbonyl]-5-(carbomethoxymethyl)isoxazoline 3-(3-amidinophenyl)-5-[(2'-aminosulfonyl-3-methyl-[1,1']-biphenyl-4-yl)aminocarbonyl)]-5-(carbomethoxyethyl)isoxazoline 3-(3-amidinophenyl)-5-[(2'-aminosulfonyl-3-methyl-[1,1']-biphenyl-4-yl)aminocarbonyl]-5-(carboxyethyl)isoxazoline 3-(3-amidinophenyl)-5-[(2'-aminosulfonyl-3-methyl-[1,1']-biphenyl-4-yl)aminocarbonyl]-5-(carbomethoxyethylene)isoxazoline 3-(3-amidinophenyl)-5-[[5-(2'-aminosulfonylphenyl-1-yl)pyrimidin-2-yl]aminocarbonyl]-5-(aminocarbonylmethyl)isoxazoline 3-(3-amidinophenyl)-5-[[5-(2'-aminosulfonylphenyl-1-yl)pyrimidin-2-yl]aminocarbonyl]-5-(hydroxyethyl)isoxazoline 3-(3-amidinophenyl)-5-[[5-(2'-aminosulfonylphenyl-1-yl)pyrimidin-2-yl]aminocarbonyl]-5-(methoxyethyl)isoxazoline 3-(3-amidinophenyl)-5-[[5-(2'-aminosulfonylpherlyl-1-yl)pyrimidin-2-yl]aminocarbonyl]-5-(methyl)isoxazoline 3-(3-amidinophenyl)-5-[(2'-aminosulfonyl-[1,1']-biphenyl-4-yl)aminocarbonyl]-5-(carbomethoxymethyl)isoxazoline 3-(3-amidinophenyl)-5-[(2'-aminosulfonyl-[1,1']-biphenyl-4-yl)aminocarbonyl]-5-(carboxymethyl)isoxazoline 3-(3-amidinophenyl)-5-[(2'-aminosulfonyl-[1,1']-biphenyl-4-yl)aminocarbonyl]-5-(aminocarbonylmethyl)isoxazoline 3-(3-amidinophenyl)-5-[(2'-aminosulfonyl-[1,1']-biphenyl-4-yl)aminocarbonyl)-5-(hydroxyethyl)isoxazoline 3-(3-amidinophenyl)-5-[(2'-aminosulfonyl-[1,1']-biphenyl-4-yl)aminocarbonyl]-5-(carbomethoxymethylaminocarbonylmethyl)isoxazoline 3-(3-amidinophenyl)-5-[(2'-aminosulfonyl-[1,1']-biphenyl-4-yl)aminocarbonyl]-5-[(imidazole-4-yl)ethylaminocarbonylmethyl]isoxazoline 3-(3-amidinophenyl)-5-[(2'-aminosulfonyl-[1,1']-biphenyl-4-yl)aminocarbonyl]-5-(methoxyethyl)isoxazoline 3-(3-amidinophenyl)-5-[(2'-aminosulfonyl-[1,1']-biphenyl-4-yl)aminocarbonyl]-5-(methyl)isoxazoline 3-(3-amidinophenyl)-5-[(2'-aminosulfonyl-3-methyl-[1,1']-biphenyl-4-yl)aminocarbonyl]-5-(carbomethoxymethyl)isoxazoline 3-(3-amidinophenyl)-5-[(2'-aminosulfonyl-3-methyl-[1,1']-biphenyl-4-yl)aminocarbonyl]-5-(carboxymethyl)isoxazoline 3-(3-amidinophenyl)-5-[(2'-aminosulfonyl-3-methyl-[1,1']-biphenyl-4-yl)aminocarbonyl]-5-(aminocarbonylmethyl)isoxazoline 3-(3-amidinophenyl)-5-[(2'-aminosulfonyl-3-methyl[1,1']-biphenyl-4-yl)aminocarbonyl]-5-(carbomethoxymethylaminocarbonylmethyl)isoxazoline 3-(3-amidinophenyl)-5-[(2'-aminosulfonyl-3-methyl-[1,1']-biphenyl-4-yl)aminocarbonyl]-5-(hydroxyethyl)isoxazoline 3-(3-amidinophenyl)-5-[(2'-aminosulfonyl-3-methyl-[1,1']-biphenyl-4-yl)aminocarbonyl]-5-(methoxyethyl)isoxazoline 3-(3-amidinophenyl)-5-[(2'-aminosulfonyl-3-methyl-[1,1']-biphenyl-4-yl)aminocarbonyl]-5-(methyl)isoxazoline 3-(3-amidinophenyl)-5-[(2'-aminosulfonyl-3-fluoro-[1,1']-biphenyl-4-yl)aminocarbonyl]-5-(carbomethoxymethyl)isoxazoline 3-(3-amidinophenyl)-5-[(2'-aminosulfonyl-3-fluoro-[1,1']-biphenyl-4-yl)aminocarbonyl]-5-(carboxymethyl)isoxazoline 3-(3-amidinophenyl)-5-[(2'-aminosulfonyl-3-fluoro-[1,1']-biphenyl-4-yl)aminocarbonyl]-5-(aminocarbonylmethyl)isoxazoline 3-(3-amidinophenyl)-5-[(2'-aminosulfonyl-3-fluoro-[1,1']-biphenyl-4-yl)aminocarbonyl]-5-(hydroxyethyl)isoxazoline 3-(3-amidinophenyl)-5-[(2'-aminosulfonyl-3-fluoro-[1,1']-biphenyl-4-yl)aminocarbonyl]-5-(methoxyethyl)isoxazoline 3-(3-amidinophenyl)-5-[(2'-aminosulfonyl-3-fluoro-[1,1']-biphenyl-4-yl)aminocarbonyl]-5-(methyl)isoxazoline 3-(3-amidinophenyl)-5-[[2-(2'-aminosulfonylphenyl-1-yl)pyridin-5-yl]aminocarbonyl]-5-(carbomethoxymethyl)isoxazoline 3-(3-amidinophenyl)-5-[[2-(2'-aminosulfonylphenyl-1-yl)pyridin-5-yl]aminocarbonyl]-5-(carboxymethyl)isoxazoline 3-(3-amidinophenyl)-5-[[2-(2'-aminosulfonylphenyl-1-yl)pyridin-5-yl]aminocarbonyl]-5-(aminocarbonylmethyl)isoxazoline 3-(3-amidinophenyl)-5-[[2-(2'-aminosulfonylphenyl-1-yl)pyridin-5-yl]aminocarbonyl]-5-(hydroxyethyl)isoxazoline 3-(3-amidinophenyl)-5-[[2-(2'-aminosulfonylphenyl-1-yl)pyridin-5-yl]aminocarbonyl]-5-(methoxyethyl)isoxazoline 3-(3-amidinophenyl)-5-[[2-(2'-aminosulfonylphenyl-1-yl)pyridin-5-yl]aminocarbonyl]-5-(methyl)isoxazoline 3-(3-amidinophenyl)-5-[[5-(2'-aminosulfonylphenyl-1-yl)pyridin-2-yl]aminocarbonyl]-5-(carbomethoxymethyl)isoxazoline 3-(3-amidinophenyl)-5-[[5-(2'-aminosulfonylphenyl-1-yl)pyridin-2-yl]aminocarbonyl]-5-(carboxymethyl)isoxazoline 3-(3-amidinophenyl)-5-[[5-(2'-aminosulfonylphenyl-1-yl)pyridin-2-yl]aminocarbonyl]-5-(aminocarbonylmethyl)isoxazoline 3-(3-amidinophenyl)-5-[[5-(2'-aminosulfonylphenyl-1-yl)pyridin-2-yl]aminocarbonyl]-5-(hydroxyethyl)isoxazoline 3-(3-amidinophenyl)-5-[[5-(2'-aminosulfonylphenyl-1-yl)pyridin-2-yl]aminocarbonyl]-5-(methoxyethyl)isoxazoline 3-(3-amidinophenyl)-5-[[5-(2'-aminosulfonylphenyl-1-yl)pyridin-2-yl]aminocarbonyl]-5-(methyl)isoxazoline 3-(3-amidinophenyl)-5-[[5-(2'-aminosulfonylphenyl-1-yl)pyrimidin-2-yl]aminocarbonyl]-5-(carbomethoxymethyl)isoxazoline 3-(3-amidinophenyl)-5-[[5-(2'-aminosulfonylphenyl-1-yl)pyrimidin-2-yl]aminocarbonyl]-5-(carboxymethyl)isoxazoline 3-(3-amidinophenyl)-5-[5-(2'-aminosulfonylphenyl-1-yl)pyrimidin-2-yl]aminocarbonyl-5-carbomethoxymethyl-isoxazoline 3-(3-amidinophenyl)-5-[5-(2'-aminosulfonylphenyl-1-yl)pyridin-2-yl]aminocarbonyl-5-carbomethoxymethyl-isoxazoline 3-(3-amidinophenyl)-5-[2'-aminosulfonyl-[1,1']-biphenyl-4-yl]aminocarbonyl-5-(tetrazol-1-yl)methyl-isoxazoline 3-(3-amidinophenyl)-5-[5-(2'-aminosulfonylphenyl-1-yl)pyridin-2-yl]aminocarbonyl-5-(tetrazol-1-yl)methyl-isoxazoline 3-(3-amidinophenyl)-5-[5-(2'-aminosulfonylphenyl-1-yl)pyrimidin-2-yl]aminocarbonyl-5-(tetrazol-1-yl)methyl-isoxazoline 3-(3-amidinophenyl)-5-[2'-trifluoromethyl-[1,1']-biphenyl-4-yl]aminocarbonyl-5-(tetrazol-1-yl)methyl-isoxazoline 3-(3-amidinophenyl)-5-[5-(2'-trifluoromethylphenyl-1-yl)pyridin-2-yl]aminocarbonyl-5-(tetrazol-1-yl)methyl-isoxazoline 3-(3-amidinophenyl)-5-[5-(2'-trifluoromethylphenyl-1-yl)pyrimidin-2-yl]aminocarbonyl-5-(tetrazol-1-yl)methyl-isoxazoline 3-(3-amidinophenyl)-5-[5-(2'-trifluoromethyl-
sulfonylphenyl-1-yl)pyridin-2-yl]aminocarbonyl-5-
(tetrazol-1-yl)methyl-isoxazoline 3-(3-amidinophenyl)-5-[5-(2'-trifluoromethyl-
sulfonylphenyl-1-yl)pyrimidin-2-yl]aminocarbonyl-5-
(tetrazol-1-yl)methyl-isoxazoline 3-(3-amidinophenyl)-5-[2'-aminosulfonyl-3-flouro-[1,1']-
biphenyl-4-yl]aminocarbonyl-5-(tetrazol-1-yl)methyl-
isoxazoline 3-(3-amidinophenyl)-5-[2'-aminosulfonyl-3-chloro-[1,
1']-biphenyl-4-yl]aminocarbonyl-5-(tetrazol-1-yl)
methyl-isoxazoline 3-(3-amidinophenyl)-5-[2'-trifluoromethyl-3-flouro-[1,
1']-biphenyl-4-yl]aminocarbonyl-5-(tetrazol-1-yl)
methyl-isoxazoline 3-(3-amidinophenyl)-5-[2'-trifluoromethyl-3-chloro-[1,
1']-biphenyl-4-yl]aminocarbonyl-5-(tetrazol-1-yl)
methyl-isoxazoline 3-(3-amidinophenyl)-5-[5-(2'-aminosulfonylphenyl-1-yl)
pyridin-2-yl]aminocarbonyl-5-methoxymethyl-
isoxazoline 3-(3-amidinophenyl)-5-[2'-methylaminosulfonyl-[1,1']-
biphenyl-4-yl]aminocarbonyl-5-(tetrazol-1-yl)methyl-
isoxazoline 3-(3-amidinophenyl)-5-[5-(2'-methylamino-
sulfonylphenyl-1-yl)pyridin-2-yl]aminocarbonyl-5-
(tetrazol-1-yl)methyl-isoxazoline 3-(3-amidinophenyl)-5-[2'-methylsulfonyl-[1,1']-
biphenyl-4-yl]aminocarbonyl-5-(tetrazol-1-yl)methyl-
isoxazoline 3-(3-amidinophenyl)-5-[2'-methylsulfonyl-fluoro-[1,1']-
biphenyl-4-yl]aminocarbonyl-5-(tetrazol-1-yl)methyl-
isoxazoline 3-(3-amidinophenyl)-5-[2'-methylsulfonyl-chloro-[1,1']-
biphenyl-4-yl]aminocarbonyl-5-(tetrazol-1-yl)methyl-
isoxazoline 3-(3-amidinophenyl)-5-[2'-trifluoromethylsulfonyl-[1,1']-
biphenyl-4-yl]aminocarbonyl-5-(tetrazol-1-yl)methyl-
isoxazoline 3-(3-amidinophenyl)-5-[2'-aminosulfonyl-[1,1']-
biphenyl-4-yl]aminocarbonyl-5-(imidazol-1-yl)
methyl-isoxazoline 3-(3-amidinophenyl)-5-[2'-trifluoromethylsulfonyl-3-
fluoro-[1,1']-biphenyl-4-yl]aminocarbonyl-5-(tetrazol-
1-yl)methyl-isoxazoline 3-(3-amidinophenyl)-5-[2'-trifluoromethylsulfonyl-3-
chloro-[1,1']-biphenyl-4-yl]aminocarbonyl-5-(tetrazol-
1-yl)methyl-isoxazoline 3-(3-amidinophenyl)-5-[2'-aminosulfonyl-[1,1']-
biphenyl-4-yl]aminocarbonyl-5-(imidazol-1-yl)
methyl-isoxazoline 3-(3-amidinophenyl)-4-(2'-aminosulfonyl-[1,1']-
biphenyl-4-yl)aminocarbonyl-5-methoxymethyl-
isoxazoline 3-(3-amidinophenyl)-4-(2'-aminosulfonyl-[1,1']-
biphenyl-4-yl)aminocarbonyl-5-trifluoromethyl-
isoxazoline and 3-(3-amidinophenyl)-5-(2'-aminosulfonyl-[1,1']-
biphenyl-4-yl)aminocarbonyl-4-methoxymethyl-
isoxazoline.

6. Pharmaceutical composition comprising a therapeutically effective amount of a compound of any of claims 1 through 5 and a pharmaceutically acceptable carrier.

7. A method of treating a thromboembolic disorder in a mammal which comprises administering to the mammal a therapeutically effective amount of a compound of any of claims 1 through 5.

8. A compound according to claim 1, wherein the compound is of Formula V or VI:

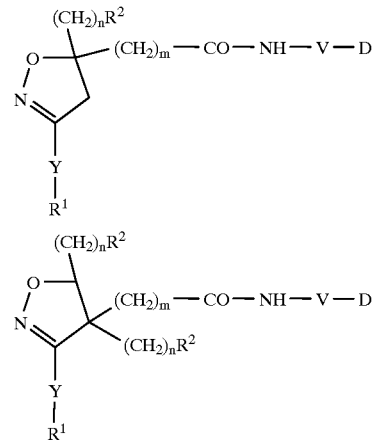

wherein

R$^1$ is (CH$_2$)$_p$NR$^5$R$^6$; and,

Y is selected from:

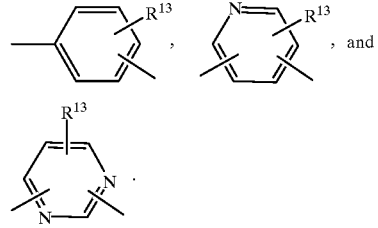

9. A compound according to claim 8, wherein:

Y is

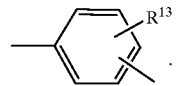

10. A compound according to claim 8, wherein:

Y is

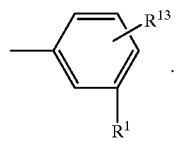

11. A compound according to claim 1, wherein the compound is of Formula V or VI:
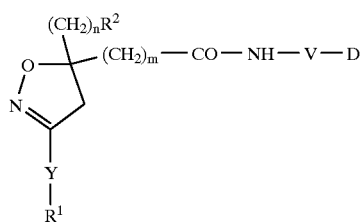
(V)
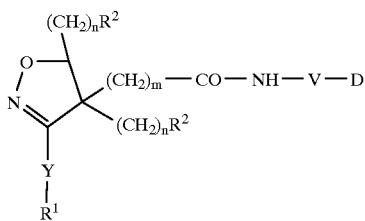
(VI)
wherein
$R^1$ is $CONR^5R^6$; and,
Y is selected from:
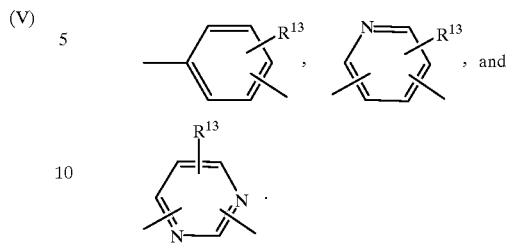
12. A compound according to claim 11, wherein:
Y is
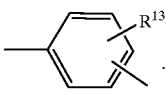.
* * * * *